US006060283A

United States Patent [19]

Okura et al.

[11] Patent Number: 6,060,283

[45] Date of Patent: May 9, 2000

[54] GENOMIC DNA ENCODING HUMAN INTERLEUKIN-18 (IL-18, INTERFERON-γ INDUCING FACTOR)

[75] Inventors: Takanori Okura; Kakuji Torigoe; Masashi Kurimoto, all of Okayama, Japan

[73] Assignee: Kabushiki Kaisha Hayashibara Seibutsu Kagaku Kenkyujo, Okayama, Japan

[21] Appl. No.: 08/884,324

[22] Filed: Jun. 27, 1997

[30] Foreign Application Priority Data

Jun. 27, 1996 [JP] Japan .................................... 8-185305

[51] Int. Cl.[7] ...................................................... C12N 15/24

[52] U.S. Cl. .................................... 435/69.52; 536/23.51; 435/325; 435/320.1; 435/69.5

[58] Field of Search ........................ 536/23.51; 435/69.5, 435/69.52, 325, 320.1

[56] References Cited

U.S. PATENT DOCUMENTS 5,166,066 11/1992 Carter ...................................... 435/369

FOREIGN PATENT DOCUMENTS 0692536 1/1996 European Pat. Off. .
0712931 5/1996 European Pat. Off. .
0861663A2 2/1998 European Pat. Off. .
8231598 2/1995 Japan .
827189 1/1996 Japan .
8193098 7/1996 Japan .

OTHER PUBLICATIONS

J. Minowada, "Leukemia Cell Lines", Cancer Review, vol. 10, pp. 1–18, 1988.

R. Hay et al., "Cell Lines and Hybridomas", ATCC, Eighth Edition, pp. 127, 129, 131, 152, 207, 339, 1994.

M.J. Kostura et al., "Identification of a Monocyte Specific Pre–Interleukin 1B Convertase Activity", Proc. Natl. Acad. Sci. USA, vol. 86, pp. 5227–5231, Jul., 1989.

T. Shimada et al., "Basic Techniques for Gene Therapy", Biomanual Up Series, 1996. Table of contents only; partial translation only.

T. Yokota et al., "The Experimental Methods for the Gene Cloning", Biomanual Series 3, 1993. Table of contents only; partial translation only.

T. Kuriki et al., "The Handbook for the Cell Engineering", Saibo–Kagaku Handbook, 1992. Table of contents only; partial translation only.

Rothe, H., et al. (1997) *J. Clin. Invest.* 99: 469–74.

Nolan, K.F., et al. (1998) *Genomics* 51: 161–63.

USHIO et al., "Cloning of the cDNA for human IFN–γ–inducing factor, expression in *Escherichia coli*, and studies on the biologic activities of the protein", *The Journal of Immunology*, vol. 156:11 pp. 4274–4279 (Jun. 1, 1996).

BALLAST et al., "Characterization and chromosomal localizationof the human interleukin–18 gene", *BLOOD*, vol. 90, No. 10 part 2 supl. 1 p. 177b (Nov. 15, 1997).

*Primary Examiner*—David L. Fitzgerald
*Attorney, Agent, or Firm*—Browdy and Neimark

[57] ABSTRACT

Disclosed is a genomic DNA encoding a polypeptide capable of inducing the production of interferon-γ by immunocompetent cells. The genomic DNA efficiently expresses the polypeptide with high biological activities of such as inducing the production of interferon-γ by immunocompetent cells, enhancing killer cells' cytotoxicity and inducing killer cells' formation, when introduced into mammalian host cells. The high biological activities of the polypeptide facilitate its uses to treat and/or prevent malignant tumors, viral diseases, bacterial infectious diseases and immune diseases without serious side effects when administered to humans.

12 Claims, 1 Drawing Sheet

GENOMIC DNA ENCODING HUMAN INTERLEUKIN-18 (IL-18, INTERFERON-γ INDUCING FACTOR)

BACKGROUND OF THE INVENTION

1. Field of the Invention

The present invention relates to a genomic DNA, more particularly, a genomic DNA encoding a polypeptide capable of inducing the production of interferon-γ (hereinafter abbreviated as "IFN-γ") by immunocompetent cells.

2. Description of the Prior Art

The present inventors successfully isolated a polypeptide capable of inducing the production of INF-γ by immunocompetent cells and cloned a cDNA encoding the polypeptide, which is disclosed in Japanese Patent Kokai No.27,189/96 and 193,098/96. Because the present polypeptide possesses the properties of enhancing killer cells' cytotoxicity and inducing killer cells' formation as well as inducing INF-γ, a useful biologically active protein, it is expected to be widely used as an agent for viral diseases, microbial diseases, tumors and/or immunopathies, etc.

It is said that a polypeptide generated by a gene expression may be partially cleaved and/or glycosylated by processing with intracellular enzymes in human cells. A polypeptide to be used in therapeutic agents should be preferably processed similarly as in human cells, whereas human cell lines generally have a disadvantage of less producing the present polypeptide, as described in Japanese Patent Application No.269,105/96. Therefore, recombinant DNA techniques should be applied to obtain the present polypeptide in a desired amount. To produce the polypeptide processed similarly as in human cells using recombinant DNA techniques, mammalian cells should be used as the hosts.

SUMMARY OF THE INVENTION

In view of foregoing, the first object of the present invention is to provide a DNA which efficiently expresses the polypeptide production when introduced into a mammalian host cell.

The second object of the present invention is to provide a transformant into which the DNA is introduced.

The third object of the present invention is to provide a process for preparing a polypeptide, using the transformant. [Means to Attain the Object]

The present inventors' energetic studies to attain the above objects succeeded in the finding that a genomic DNA encoding the present polypeptide efficiently expresses the polypeptide production when introduced into mammalian host cells. They found that the polypeptide thus obtained possessed significantly higher biological activities than that obtained by expressing a cDNA encoding the polypeptide in *Escherichia coli.*

The first object of the present invention is attained by a genomic DNA encoding a polypeptide with the amino acid sequence of SEQ ID NO:1 (where the symbol "Xaa" means "isoleucine" or "threonine") or its homologous one, which induces interferon-γ production by immunocompetent cells.

The second object of the present invention is attained by a transformant formed by introducing the genomic DNA into a mammalian host cell.

The third object of the present invention is attained by a process for preparing a polypeptide, which comprises (a) culturing the transformant in a nutrient medium, and (b) collecting the polypeptide from the resultant culture.

BRIEF EXPLANATION OF THE ACCOMPANYING DRAWINGS

FIG. 1 is a restriction map of a recombinant DNA containing a genomic DNA according to the present invention.

Explanation of the symbols are as follows: The symbol "Hin dIII" indicates a cleavage site by a restriction enzyme Hin dIII, and the symbol "HuIGIF" indicates a genomic DNA according to the present invention.

DETAILED DESCRIPTION OF THE INVENTION

Figure 1:
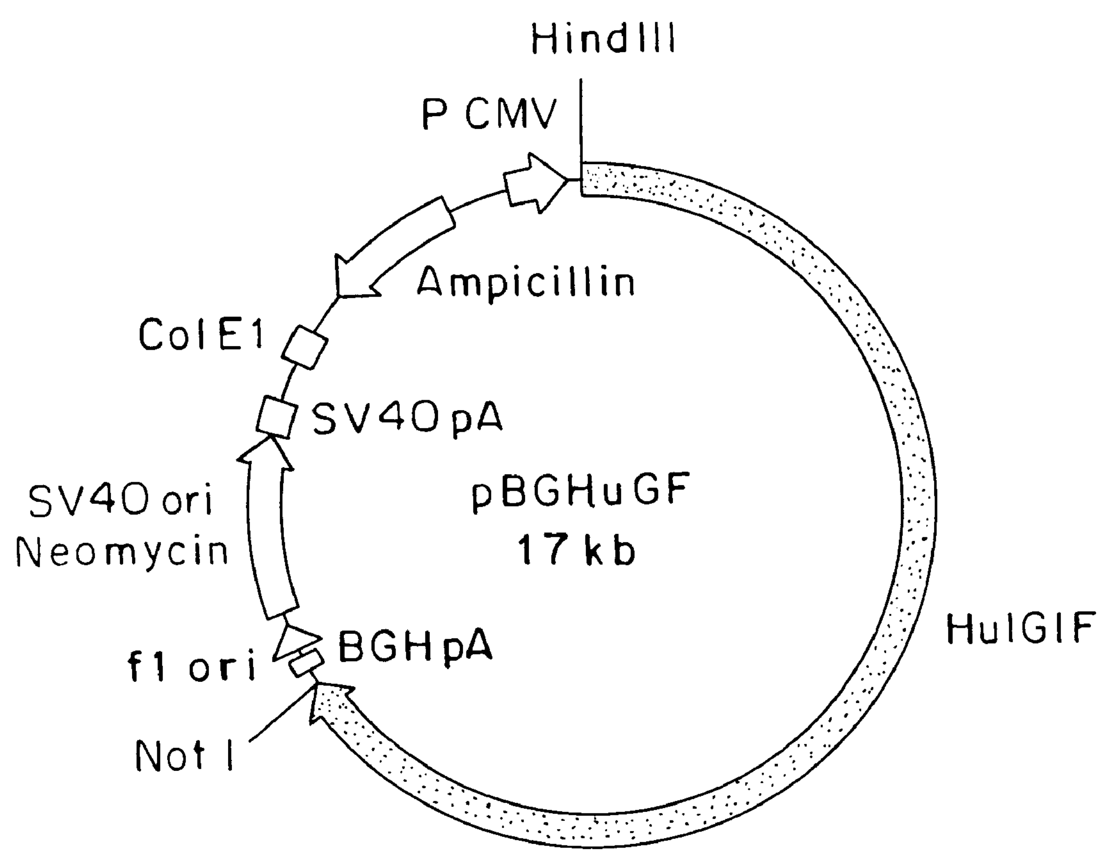

The followings are the preferred embodiments according to the present invention. This invention is made based on the identification of a genomic DNA encoding the polypeptide with the amino acid sequence of SEQ ID NO:1 or its homologous one, and the finding that the genomic DNA efficiently expresses the polypeptide with high biological activities when introduced into mammalian host cells. The genomic DNA of the present invention usually contains two or more exons, at least one of which possesses a part of or the whole of the nucleotide sequence of SEQ ID NO:2. The wording "a part" includes a nucleotide and a sequential nucleotides consisting of two or more nucleotides in SEQ ID NO:2. Examples of the exons are SEQ ID NOs:3 and 4. Human genomic DNA may contain additional exons with SEQ ID NOs:5 to 7. Since the present genomic DNA is derived from a mammalian genomic DNA, it contains introns, as a distinctive feature in mammalian genomic DNAs. The present genomic DNA usually has two or more introns such as SEQ ID NOs:8 to 12.

More particular examples of the present genomic DNA include DNAs with SEQ ID NOs:13 and 14 or complementary sequences thereunto. The DNAs with SEQ ID NOs:13 and 14 are substantially the same. The DNA with SEQ ID NO:14 contains coding regions for a leader peptide, consisting of the nucleotides 15,607th–15,685th, 17,057th–17,068th and 20,452nd–20,468th, coding regions for the present polypeptide, consisting of the nucleotides 20,469th–20,586th, 21,921st–22,054th and 26,828th–27,046th, and regions as introns, consisting of the nucleotides 15,686th–17,056th, 17,069–20,451st, 20,587th–21,920th and 22,055th–26,827th. The genomic DNA with SEQ ID NO:13 is suitable for expressing the polypeptide in mammalian host cells.

Generally in this field, when artificially expressing a DNA encoding a polypeptide in a host, one or more nucleotides in a DNA may be replaced by different ones, and appropriate promoter(s) and/or enhancer(s) may be linked to the DNA to improve the expressing efficiency or the properties of the expressed polypeptide. The present genomic DNA can be altered similarly as above. Therefore, as far as not substantially changing in the biological activities of the expressed polypeptides, the present genomic DNA should include DNAs encoding functional equivalents of the polypeptide, formed as follows: One or more nucleotides in SEQ ID NOs:3 to 14 are replaced by different ones, the untranslated regions and/or the coding region for a leader peptide in the 5'- and/or 3'-termini of SEQ ID NOs:3, 4, 5, 6, 7, 13 and 14 are deleted, and appropriate oligonucleotides are linked to either or both ends of SEQ ID NO:13.

The present genomic DNA includes general DNAs which are derived from a genome containing the nucleotide sequences as above, and it is not restricted to its sources or origins as far as it is once isolated from its original organisms. For example, the present genomic DNA can be obtained by chemically synthesizing based on SEQ ID NOs:2 to 14, or by isolating from a human genomic DNA. The isolation of the present genomic DNA from such a human genomic DNA comprises (a) isolating a genomic DNA from human cells by conventional methods, (b) screening the genomic DNA with probes or primers, which are chemically synthesized oligonucleotides with a part of or the whole of the nucleotide sequence of SEQ ID NO:2, and (c) collecting a DNA to which the probes or primers specifically hybridize. Once the present genomic DNA is obtained, it can be unlimitedly replicated by constructing a recombinant DNA with an autonomously replicable vector by conventional method and then introducing the recombinant DNA into an appropriate host such as a microorganism or an animal cell before culturing the transformant or by applying a PCR method.

The present genomic DNA is very useful in producing the polypeptide by recombinant DNA techniques since it efficiently expresses the polypeptide with high biological activities when introduced into mammalian host cells. The present invention further provides a process for preparing a polypeptide using a specific genomic DNA, comprising the steps of (a) culturing a transformant formed by introducing the present genomic DNA into mammalian host cells, and (b) collecting the polypeptide which induces INF-γ production by immunocompetent cells from the resultant culture.

The following explains the process for preparing the polypeptide according to the present invention. The present genomic DNA is usually introduced into host cells in the form of a recombinant DNA. The recombinant DNA, comprising the present genomic DNA and an autonomously replicable vector, can be relatively easily prepared by conventional recombinant DNA techniques when the genomic DNA is available. The vectors, into which the present genomic DNA can be inserted, include plasmid vectors such as pcD, pcDL-SRα, pKY4, pCDM8, pCEV4 and pME18S. The autonomously replicable vectors usually further contain appropriate nucleotide sequences for the expression of the present recombinant DNA in each host cell, which include sequences for promoters, enhancers, replication origins, transcription termination sites, splicing sequences and/or selective markers. Heat shock protein promoters or IFN-α promoters, as disclosed in Japanese Patent Kokai No.163,368/95 by the same applicant of this invention, enables to artificially regulate the present genomic DNA expression by external stimuli.

To insert the present genomic DNA into vectors, conventional methods used in this field can be arbitrarily used: Genes containing the present genomic DNA and autonomously replicable vectors are cleaved with restriction enzymes and/or ultrasonic, and the resultant DNA fragments and the resultant vector fragments are ligated. To cleave genes and vectors by restriction enzymes, which specifically act on nucleotides, more particularly, AccI, BamHI, BglII, BstXI, EcoRI, HindIII, NotI, PstI, SacI, SalI, SmaI, SpeI, XbaI, XhoI, etc., facilitate the ligation of the DNA fragments and the vector fragments. To ligate the DNA fragments and the vector fragments, they are, if necessary, first annealed, then treated with a DNA ligase in vivo or in vitro. The recombinant DNAs thus obtained can be unlimitedly replicated in hosts derived from microorganisms or animals.

Any cells conventionally used as hosts in this field can be used as the host cells: Examples of such are epithelial, interstitial and hemopoietic cells, derived from human, monkey, mouse and hamster, more particularly, 3T3 cells, C127 cells, CHO cells, CV-1 cells, COS cells, HeLa cells, MOP cells and their mutants. Cells which inherently produce the present polypeptide also can be used as the host cells: Example of such are human hemopoietic cells such as lymphoblasts, lymphocytes, monoblasts, monocytes, myeloblasts, myelocytes, granulocytes and macrophages, and human epithelial and interstitial cells derived from solid tumors such as pulmonary carcinoma, large bowel cancer and colon cancer. More particular examples of the latter hemopoietic cells are leukemia cell lines such as HBL-38 cells, HL-60 cells ATCC CCL240, K-562 cells ATCC CCL243, KG-1 cells ATCC CCL246, Mo cells ATCC CRL8066, THP-1 cells ATCC TIB202, U-937 cells ATCC CRL1593.2, described by J. Minowada et al. in "*Cancer Research*", Vol.10, pp.1–18 (1988), derived from leukemias or lymphoma including myelogenous leukemias, promyelocytic leukemias, monocytic leukemias, adult T-cell leukemias and hairy cell leukemias, and their mutants. The present polypeptide-processibility of these leukemia cell lines and their mutants is so distinguished that they can easily yield the polypeptide with higher biological activities when used as hosts.

To introduce the present DNA into the hosts, conventional methods such as DEAE-dextran method, calcium phosphate transfection method, electroporation method, lipofection method, microinjection method, and viral infection method as using retrovirus, adenovirus, herpesvirus and vaccinia virus, can be used. The polypeptide-producing clones in the transformants can be selected by applying the colony hybridization method or by observing the polypeptide production after culturing the transformants in culture media. For example, the recombinant DNA techniques using mammalian cells as hosts are detailed in "*Jikken-Igaku-Bessatsu Saibo-Kogaku Handbook* (The handbook for the cell engineering)" (1992), edited by Toshio KUROKI, Masaru TANIGUCHI and Mitsuo OSHIMURA, published by YODOSHA. CO., LTD., Tokyo, Japan, and "*Jikken-Igaku-Bessatsu Biomanual Series* 3 *Idenshi Cloning Jikken-Ho* (The experimental methods for the gene cloning)" (1993), edited by Takahi YOKOTA and Ken-ichi ARAI, published by YODOSHA CO., LTD., Tokyo, Japan.

The transformants thus obtained secrete the present polypeptide intracellularly and/or extracellularly when cultured in culture media. As the culture media, conventional ones used for mammalian cells can be used. The culture media generally comprise (a) buffers as a base, (b) inorganic ions such as sodium ion, potassium ion, calcium ion, phosphoric ion and chloric ion, (c) micronutrients, carbon sources, nitrogen sources, amino acids and vitamins, which are added depending on the metabolic ability of the cells, and (d) sera, hormones, cell growth factors and cell adhesion factors, which are added if necessary. Examples of individual media include 199 medium, DMEM medium, Ham's F12 medium, IMDM medium, MCDB 104 medium, MCDB 153 medium, MEM medium, RD medium, RITC 80-7 medium, RPMI-1630 medium, RPMI-1640 medium and WAJC 404 medium. The cultures containing the present polypeptide are obtainable by inoculating the transformants into the culture media to give a cell density of $1\times10^4$–$1\times10^7$ cells/ml, more preferably, $1\times10^5$–$1\times10^6$ cells/ml, and then subjecting to suspension- or monolayer-cultures at about 37° C. for 1–7 days, more preferably, 2–4 days, while appropriately replacing the culture media with a fresh preparation of the culture media. The cultures thus obtained usually contain the present polypeptide in a concentration of about 1–100 μg/ml, which may vary depending on the types of the transformants or the culture conditions used.

While the cultures thus obtained can be used intact as an INF-γ inducer, they are usually subjected to a step for separating the present polypeptide from the cells or the cell debris using filtration, centrifugation, etc. before use, which may follow a step for disrupting the cells with supersonication, cell-lytic enzymes and/or detergents if desired, and to a step for purifying the polypeptide. The cultures from which the cells or cell debris are removed are usually subjected to conventional methods used in this field for purifying biologically active polypeptides, such as salting-out, dialysis, filtration, concentration, separatory sedimentation, ion-exchange chromatography, gel filtration chromatography, adsorption chromatography, chromatofocusing, hydrophobic chromatography, reversed phase chromatography, affinity chromatography, gel electrophoresis and/or isoelectric focusing. The resultant purified polypeptide can be concentrated and/or lyophilized into liquids or solids depending on final uses. The monoclonal antibodies disclosed in Japanese Patent Kokai No.231,598/96 by the same applicant of this invention are extremely useful to purify the present polypeptide. Immunoaffinity chromatography using monoclonal antibodies yields the present polypeptide in a relatively high purity at the lowest costs and labors.

The polypeptide obtainable by the process according to the present invention exerts strong effects in the treatment and/or the prevention for INF-γ- and/or killer cell-susceptive diseases since it possesses the properties of enhancing killer cells' cytotoxicity and inducing killer cells' formation as well as inducing INF-γ, a useful biologically active protein, as described above. The polypeptide according to the present invention has a high activity of inducing INF-γ, and this enables a desired amount of INF-γ production with only a small amount. The polypeptide is so low toxic that it scarcely causes serious side effects even when administered in a relatively-high dose. Therefore, the polypeptide has an advantage that it can readily induce INF-γ in a desired amount without strictly controlling the dosage. The uses as agents for susceptive diseases are detailed in Japanese Patent Application No.28,722/96 by the same applicant of this invention.

The present genomic DNA is also useful for so-called "gene therapy". According to conventional gene therapy, the present DNA can be introduced into patients with INF-γ- and/or killer cell-susceptive diseases by directly injecting after the DNA is inserted into vectors derived from viruses such as retrovirus, adenovirus and adeno-associated virus or is incorporated into cationic- or membrane fusible-liposomes, or by self-transplanting lymphocytes which are collected from patients before the DNA is introduced. In adoptive immunotherapy with gene therapy, the present DNA is introduced into effector cells similarly as in conventional gene therapy. This can enhance the cytotoxicity of the effector cells to tumor cells, resulting in improvement of the adoptive immunotherapy. In tumor vaccine therapy with gene therapy, tumor cells from patients, into which the present genomic DNA is introduced similarly as in conventional gene therapy, are self-transplanted after proliferated ex vivo up to give a desired cell number. The transplanted tumor cells act as vaccines in the patients to exert a strong antitumor immunity specifically to antigens. Thus, the present genomic DNA exhibits considerable effects in gene therapy for diseases including viral diseases, microbial diseases, malignant tumors and immunopathies. The general procedures for gene therapy are detailed in "*Jikken-Igaku-Bessatsu Biomanual UP Series Idenshichiryo-no-Kisogijutsu* (Basic techniques for the gene therapy)" (1996), edited by Takashi ODAJIMA, Izumi SAITO and Keiya OZAWA, published by YODOSHA CO., LTD., Tokyo, Japan.

The following examples explain the present invention, and the techniques used therein are conventional ones used in this field: For example, the techniques are described in "*Jikken-Igaku-Bessatsu Saibo-Kogaku Handbook* (The handbook for the cell engineering)", (1992), edited by Toshio KUROKI, Masaru TANIGUCHI and Mitsuo OSHIMURA, published by YODOSHA CO., LTD., Tokyo, Japan, and "*Jikken-Igaku-Bessatsu Biomanual Series* 3 *Idenshi Clonong Jikken-Ho* (The experimental methods for the gene cloning)" (1993), edited by Takahi YOKOTA and Ken-ichi ARAI, published by YODOSHA CO., LTD., Tokyo, Japan.

EXAMPLE 1

Cloning Genomic DNA and Determination of Nucleotide Sequence

Example 1-1

Determination of Partial Nucleotide Sequence

Five ng of "PromoterFinder™ DNA PvuII LIBRARY", a human placental genomic DNA library commercialized by CLONTECH Laboratories, Inc., California, USA, 5 μl of 10×Tth PCR reaction solution, 2.2 μl of 25 mM magnesium acetate, 4 μl of 2.5 mM dNTP-mixed solution, one μl of the mixed solution of 2 unit/μl rTth DNA polymerase XL and 2.2 μg/μl Tth Start Antibody in a ratio of 4:1 by volume, 10 pmol of an oligonucleotide with the nucleotide sequence of 5'-CCATCCTAATACGACTCACTATAGGGC-3' (SEQ ID NO:16) as an adaptor primer, and 10 pmol of an oligonucleotide with the nucleotide sequence of 5'-TTCCTCTTCCCGAAGCTGTGTAGACTGC-3' (SEQ ID NO:17) as an anti-sense primer, which was chemically synthesized based on the sequence of the nucleotides 88th–115th in SEQ ID NO:2, were mixed and volumed up to 50 μl with sterilized distilled water. After incubating at 94° C. for one min, the mixture was subjected to 7 cycles of incubations at 94° C. for 25 sec and at 72° C. for 4 min, followed by 32 cycles of incubations at 94° C. for 25 sec at 67° C. for 4 min to perform PCR.

The reaction mixture was diluted by 100 folds with sterilized distilled water. One μl of the dilution, 5 μl of 10×Tth PCR reaction solution, 2.2 μl of 25 mM magnesium acetate, 4 μl of 2.5 mM dNTP-mixed solution, one μl of the mixed solution of 2 unit/μl rTth DNA polymerase XL and 2.2 μg/μl Tth Start Antibody in a ratio of 4:1 by volume, 10 pmol of an oligonucleotide with the nucleotide sequence of 5'-CTATAGGGCACGCGTGGT-3' (SEQ ID NO:18) as a nested primer, and 10 pmol of an oligonucleotide with the nucleotide sequence of 5'-TTCCTCTTCCCGAAGCTGTGTAGACTGC-3' (SEQ ID NO:19) as an anti-sense primer, which was chemically synthesized similarly as above, were mixed and volumed up to 50 μl with sterilized distilled water. After incubating at 94° C. for one min, the mixture was subjected to 5 cycles of incubations at 94° C. for 25 sec and at 72° C. for 4 min, followed by 22 cycles of incubations at 94° C. for 25 sec and at 67° C. for 4 min to perform PCR for amplifying a DNA fragment of the present genomic DNA. The genomic DNA library and reagents for PCR used above were mainly from "PromoterFinder™ DNA WALKING KITS", commercialized by CLONTECH Laboratories, Inc., California, USA.

An adequate amount of the PCR product thus obtained was mixed with 50 ng of "pT7 Blue(R)", a plasmid vector commercialized by Novagen, Inc., WI, USA, and an adequate amount of T4 DNA ligase, and 100 mM ATP was added to give a final concentration of one mM, followed by incubating at 16° C. for 18 hr to insert the DNA fragment into the plasmid vector. The obtained recombinant DNA was introduced into an *Escherichia coli* JM109 strain by the competent cell method to form a transformant, which was then inoculated into L-broth medium (pH 7.2) containing 50 μg/ml ampicillin and cultured at 37° C. for 18 hr. The cells were isolated from the resulting culture, and then subjected to the conventional alkali-SDS method to collect a recombinant DNA. The dideoxy method analysis confirmed that the recombinant DNA contained the DNA fragment with a sequence of the nucleotides 5,150th–6,709th in SEQ ID NO:14.

Example 1-2

Determination of Partial Nucleotide Sequence

PCR was performed in the same conditions as the first PCR in Example 1-1, but an oligonucleotide with the nucleotide sequence of 5'-GTAAGTTTTCACCTTCCAACTGTAGAGTCC-3' (SEQ ID NO:20), which was chemically synthesized based on the nucleotide sequence of the DNA fragment in Example 1–1, was used as an anti-sense primer.

The reaction mixture was diluted by 100 folds with sterilized distilled water. One μl of the dilution was placed into a reaction tube, and PCR was performed in the same conditions as used in the second PCR in Example 1-1 to amplify another DNA fragment of the present genomic DNA, but an oligonucleotide with the nucleotide sequence of 5'-GGGATCAAGTAGTGATCAGAAGCAGCACAC-3' (SEQ ID NO:21), which was chemically synthesized based on the nucleotide sequence of the DNA fragment in Example 1-1, was used as an anti-sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 1st-5,228th in SEQ ID NO:14.

Example 1-3

Determination of Partial Nucleotide Sequence 0.5 μg of a human placental genomic DNA, commercialized by CLONTECH Laboratories, Inc., California, USA, 5 μl of 10×PCR reaction solution, 8 μl of 2.5 mM dNTP-mixed solution, one μl of the mixed solution of 5 unit/μl "TAKARA LA Taq POLYMERASE" and 1.1 μg/μl "TaqStart ANTIBODY" in a ratio of 1:1 by volume, both of them are commercialized by Takara Syuzo Co., Tokyo, Japan, 10 pmol of an oligonucleotide with the nucleotide sequence of 5'-CCTGGCTGCCAACTCTGGCTGCTAAAGCGG-3' (SEQ ID NO:22) as a sense primer, chemically synthesized based on a sequence of the nucleotides 46th–75th in SEQ ID NO:2, and 10 pmol of an oligonucleotide with the nucleotide sequence of 5'-GTATTGTCAATAAATTTCATTGCCACAAAGTTG-3' (SEQ ID NO:23) as an anti-sense primer, chemically synthesized based on a sequence of the nucleotides 210th–242nd in SEQ ID NO:2, were mixed and volumed up to 50 μl with sterilized distilled water. After incubating at 94° C. for one min, the mixture was subjected to 5 cycles of incubations at 98° C. for 20 sec and at 68° C. for 10 min, followed by 25 cycles of incubations at 98° C. for 20 sec and 68° C. for 10 min, with adding 5 sec in times to every cycle, and finally incubated at 72° C. for 10 min to amplify further DNA fragment of the present genomic DNA. The reagents for PCR used above were mainly from "TAKARA LA PCR KIT VERSION 2", commercialized by Takara Syuzo Co., Tokyo, Japan.

The DNA fragment was inserted into the plasmid vector similarly as in Example 1–1 to obtain a recombinant DNA. The recombinant DNA was replicated in *Escherichia coli* before being collected. The analysis of the collected recombinant DNA confirmed that it contained the DNA fragment with a sequence of the nucleotides 6,640th–15,671st in SEQ ID NO:14.

Experiment 1–4

Determination of Partial Nucleotide Sequence

PCR was performed in the same conditions as the PCR in Example 1–3 to amplify further another DNA fragment of the present genomic DNA; but an oligonucleotide with the nucleotide sequence of 5 1 -AAGATGGCTGCTGAACCAGTAGAAGACAATTGC-3' (SEQ ID NO:24), chemically synthesized based on a sequence of the nucleotide 175th–207th in SEQ ID NO:2, was used as a sense primer, an oligonucleotide with the nucleotide sequence of 5'-TCCTTGGTCAATGAAGAGAACTTGGTC-3'(SEQ ID NO:25), chemically synthesized based on a sequence of nucleotides 334th–360th in the SEQ ID NO:2, was used as an anti-sense primer, and after incubating at 98° C. for 20 sec, the reaction mixture was subjected to 30 cycles of incubations at 98° C. for 20 sec and at 68° C. for 3 min, followed by incubating at 72° C. for 10 min.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 15,604th–20,543rd in SEQ ID NO:14.

Example 1-5

Determination of Partial Nucleotide Sequence

PCR was performed in the same conditions as the PCR in Example 1-4 to amplify further another DNA fragment of the present genomic DNA, but an oligonucleotide with the nucleotide sequence of 5'-CCTGGAATCAGATTACTTTGGCAAGCTTGAATC-3' (SEQ ID NO:26), chemically synthesized based on the sequence of the nucleotide 273rd–305th in SEQ ID NO:2, was used as a sense primer, and an oligonucleotide with the nucleotide sequence of 5'-GGAAATAATTTTGTTCTCACAGGAGAGAGTTG-3' (SEQ ID NO:27), chemically synthesized based on the sequence of nucleotides 500th–531st in the SEQ ID NO:2, was used as an anti-sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 20,456th–22,048th in SEQ ID NO:14.

Example 1-6

Determination of Partial Nucleotide Sequence

PCR was performed in the same conditions as the PCR in Example 1–4 to amplify further another DNA fragment of the present genomic DNA, but an oligonucleotide with the nucleotide sequence of 5'-GCCAGCCTAGAGGTATGGCTGTAACTATCTC-3' (SEQ ID NO:28), chemically synthesized based on the sequence of the nucleotide 449th–479th in SEQ ID NO:2, was used as a sense primer, and an oligonucleotide with the nucleotide sequence of 5'-GGCATGAAATTTTAATAGCTAGTCTTCGTTTTG-3' (SEQ ID NO:29), chemically synthesized based on the sequence of nucleotides 745th–777th in the SEQ ID NO:2, was used as an anti-sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 21,996th–27,067th in SEQ ID NO:14.

Example 1-7

Determination of Partial Nucleotide Sequence

PCR was performed in the same conditions as the first PCR in Example 1-2 to amplify further another DNA fragment in the present genomic DNA, but an oligonucleotide with the nucleotide sequence of 5'-GTGACATCATATTCTTTCAGAGAAGTGTCC-3' (SEQ ID NO:30), chemically synthesized based on the sequence of the nucleotide 575th–604th in SEQ ID NO:2, was used as a sense primer.

The reaction mixture was diluted by 100 folds with sterilized distilled water. One μl of the dilution was placed into a reaction tube, and PCR was performed in the same conditions as the second PCR in Example 1-2 to amplify further another DNA fragment of the present genomic DNA, but an oligonucleotide with the sequence of 5'-GCAATTTGAATCTTCATCATACGAAGGATAC-3' (SEQ ID NO:31), chemically synthesized based on a sequence of the nucleotides 624th–654th in SEQ ID NO:2, was used as a sense primer.

The DNA fragment was inserted into the plasmid vector similarly as in Example 1-1 to obtain a recombinant DNA. The recombinant DNA was replicated in *Escherichia coli* before being collected. The analysis of the collected recombinant DNA confirmed that it contained the DNA fragment with a sequence of the nucleotides 26,914th–28,994th in SEQ ID NO:14.

Example 1-8

Determination of Complete Nucleotide Sequence

Comparing the nucleotide sequence of SEQ ID NO:2, which was proved to encode the present polypeptide, as disclosed in Japanese Patent Kokai No.193,098/96 by the same applicant of this invention, with the partial nucleotide sequences identified in Examples 1-1 to 1-7, it was proved that the present genomic DNA contained the nucleotide sequence of SEQ ID NO:14. SEQ ID NO:14, consisting of 28,994 base pairs (bp), was extremely longer than the SEQ ID NO:2, consisting of only 471 bp. This suggested that SEQ ID NO:14 contained introns, a characteristic of eukaryotic cells.

It was examined where partial nucleotide sequences of SEQ ID NO:2, i.e., exons, and the donor and acceptor sites in introns, respectively consisting of the nucleotides of GT and AG, located in SEQ ID NO:14. Consequently, it was proved that SEQ ID NO:14 contained at least 5 introns, which located in the order of SEQ ID NOs:10, 11, 12, 8 and 9 in the direction from the 5'- to the 3'-termini. Therefore, the sequences between the neighboring introns must be exons, which were thought to be located in the order of SEQ ID NOs:5, 6, 3, 4 and 7 in the direction from the 5'- to the 3'-termini. It was also proved that SEQ ID NO:7 contained the 3'-untranslated region other than the exons. The features of the sequence elucidated as this are arranged in SEQ ID NO:14.

As disclosed in a patent application by the same applicant of this invention, the present polypeptide is produced as a polypeptide with N-terminal amino acid of tyrosine other than methionine in human cells, which is observed in SEQ ID NO:1. This suggests that the present genomic DNA contains a leader peptide region in the upstream of the 5'-terminus of the present polypeptide-encoding region. A sequence consisting of 36 amino acids encoded by the upstream of the nucleotides 20,469th–20,471st. which is the nucleotides of TAC, are described as a leader peptide in SEQ ID NO:14.

EXAMPLE 2

Preparation of Recombinant DNA pBGHuGF for Expression 0.06 ng of the DNA fragment in Example 1-4 in a concentration of 3 ng/50 μl, 0.02 ng of the DNA fragment, obtained by the methods in Example 1-5, 5 μl of 10×LA PCR reaction solution, 8 μl of 2.5 mM dNTP-mixed solution, one μl of the mixed solution of 5 unit/μl TAKARA LA Taq polymerase and 1.1 μg/μl TaqStart Antibody in a ratio of 1:1 by volume, 10 pmol of an oligonucleotide with the sequence of 5'-TCCGAAGCTTAAGATGGCTGCTGAACCAGTA-3' (SEQ ID NO:32) as a sense primer, chemically synthesized based on the nucleotide sequence of the DNA fragment in Example 1-4, and 10 pmol of an oligonucleotide with the nucleotide sequence of 5'-GGAAATAATTTTGTTCTCACAGGAGAGAGTTG-3' (SEQ ID NO:33) as an anti-sense primer, chemically synthesized based on the nucleotide sequence of the DNA fragment in Example 1-5, were mixed and volumed up to 50 μl with sterilized distilled water. After incubating at 94° C. for one min, the mixture was subjected to 5 cycles of incubations at 98° C. for 20 sec and at 72° C. for 7 min, followed by 25 cycles of incubations at 98° C. for 20 sec and 68° C. for 7 min to perform PCR. The reaction mixture was cleaved by restriction enzymes HindIII and SphI to obtain a DNA fragment of about 5,900 bp, with cleavage sites by HindIII and SphI in its both termini.

PCR was performed in the same condition as above, but 0.02 ng of the DNA fragment in Example 1-5, 0.06 ng of the DNA fragment obtained in Example 1-6, an oligonucleotide with the nucleotide sequence of 5'-ATGTAGCGGCCGCGGCATGAAATTTTAATAGCTAGTC-3' (SEQ ID NO:34) as an anti-sense primer, chemically synthesized based on the nucleotide sequence of the DNA fragment in Example 1-6, and an oligonucleotide with the sequence of 5'-CCTGGAATCAGATTACTTTGGCAAGCTTGAATC-3' (SEQ ID NO:35) as a sense primer, chemically synthesized based on the DNA fragment in Example 1-6, were used. The reaction mixture was cleaved by restriction enzymes NotI and SphI to obtain a DNA fragment of about 5,600 bp, with cleavage sites by NotI and SphI in its both termini.

A plasmid vector "pRc/CMV", containing a cytomegalovirus promoter, commercialized by Invitrogen Corporation, San Diego, USA, was cleaved by restriction enzymes HindIII and NotI to obtain a vector fragment of about 5,500 bp. The vector fragment was mixed with the above two DNA fragments of about 5,900 bp and 5,600 bp, and reacted with T4 DNA ligase to insert the two DNA fragments into the plasmid vector. An *Escherichia coli* JM109 strain was transformed with the obtained recombinant DNA, and the transformant with the plasmid vector was selected by the colony hybridization method. The selected recombinant DNA was named as "pBGHuGF". As shown in FIG. 1, the present genomic DNA, with the nucleotide sequence of SEQ ID NO:13, was ligated in the downstream of the cleavage site by the restriction enzyme HindIII in the recombinant DNA.

EXAMPLE 3

Preparation of Transformant Using CHO Cell as Host

CHO-K1 cells ATCC CCL61 were inoculated into Ham's F12 medium (pH 7.2) containing 10 v/v % bovine fetal serum and proliferated by conventional manner. The proliferated cells were collected and washed with phosphate-buffered saline (hereinafter abbreviated as "PBS") followed by suspending in PBS to give a cell density of $1\times10^7$ cells/ml.

10 $\mu$g of the recombinant DNA pBGHuGF in Example 2 and 0.8 ml of the above cell suspension were placed in a cuvette and ice-chilled for 10 min. The cuvette was installed in "GENE PULSER", an electroporation device commercialized by Bio-Rad Laboratories Inc., Brussels, Belgium, and then pulsed once with an electric discharge. After pulsing, the cuvette was immediately took out and ice-chilled for 10 min. The cell suspension from the cuvette was inoculated into Ham's F12 medium (pH 7.2) containing 10 v/v % bovine fetal serum and cultured under an ambient condition of 5 v/v % $CO_2$ at 37° C. for 3 days. To the culture medium was added G-418 to give a final concentration of 400 $\mu$g/ml, and the culturing was continued further 3 weeks under the same conditions. From about 100 colonies formed, 48 colonies were selected, and a portion of each was inoculated into a well of culturing plates with Ham's F12 medium (pH 7.2) containing 400 $\mu$g/ml G-418 and 10 v/v % bovine fetal serum and cultured similarly as above. Thereafter, to each well of the culturing plates was added 10 mM Tris-HCl buffer (pH 8.5) containing 5.1 mM magnesium chloride, 0.5 w/v % sodium deoxycholate, 1 w/v % NONIDET P-40, 10 $\mu$g/ml aprotinin and 0.1 w/v % SDS to lyse the cells.

50 $\mu$l aliquot of the cell lysates was mixed with one ml of glycerol and incubated at 37° C. for one hour, before the polypeptides in the cell lysates were separated by the SDS-polyacrylamide gel electrophoresis. The separated polypeptides were transferred to a nitrocellulose membrane in usual manner, and the membrane was soaked in the culture supernatant of the hybridoma H-1, disclosed in Japanese Patent Kokai No.231,598/96 by the same applicant of this invention, followed by washing with 50 mM Tris-HCl buffer containing 0.05 v/v % TWEEN 20 to remove an excessive mount of the monoclonal antibody. Thereafter, the nitrocellulose membrane was soaked in PBS containing rabbit-derived anti-mouse immunoglobulin antibody for one hr, which was labeled with horseradish peroxidase, followed by washing 50 mM Tris-HCl buffer (pH 7.5) containing 0.05 v/v % TWEEN 20 and soaking in 50 mM Tris-HCl buffer (pH 7.5) containing 0.005 v/v % hydrogen peroxide and 0.3 mg/ml diaminobenzidine to develop colorations. The clone, which highly produced the polypeptide, was selected based on the color development and named "BGHuGF".

EXAMPLE 4

Production of Polypeptide by Transformant and its Physicochemical Properties

The transformant BGHuGF in Experiment 3 was inoculated into Ham's F12 medium (pH 7.2) containing 400 $\mu$g/ml G-418 and 10 v/v % bovine fetal serum, and cultured under an ambient condition of 5 v/v % $CO_2$ at 37° C. for one week. The proliferated cells were collected, washed with PBS, and then washing with 10-fold volumes of ice-chilled 20 mM Hepes buffer (pH 7.4), containing 10 mM potassium chloride and 0.1 mM ethylendiaminetetraacetate bisodium salt, according to the method described in "*Proceedings of The National Academy of The Sciences of The USA*", vol. 86, pp. 5,227–5,231 (1989), by M. J. Kostura et al. The cells thus obtained were allowed to stand in 3-fold volumes of a fresh preparation of the same buffer under an ice-chilling condition for 20 min and freezed at −80° C., succeeded by thawing to disrupt the cells. The resulting cells were centrifuged to collect the supernatant.

In parallel, THP-1 cells ATCC TIB 202, derived from a human acute monocytic leukemia, was similarly cultured and disrupted. Supernatant, obtained by centrifuging the resulting cells, was mixed with the supernatant obtained from the transformant BGHuGF and incubated at 37° C. for 3 hr to react. The reaction mixture was applied to a column with "DEAE-SEPHAROSE", a gel for ion-exchange chromatography, commercialized by Pharmacia LKB Biotechnology AB, Upsalla, Sweden, equilibrated with 10 mM phosphate buffer (pH 6.6) before use. After washing the column with 10 mM phosphate buffer (pH 6.6), 10 mM phosphate buffer (pH 6.6) with a stepwise gradient of NaCl increasing from 0 M to 0.5 M was fed to the column, and fractions eluted by about 0.2 M NaCl were collected. The fractions were dialyzed against 10 mM phosphate buffer (pH 6.8) before applied to a column with "DEAE 5PW", a gel for ion-exchange chromatography, commercialized by TOSOH Corporation, Tokyo, Japan. To the column was fed 10 mM phosphate buffer (pH 6.8) with a linear gradient of NaCl increasing from 0 M to 0.5 M, and fractions eluted by about 0.2–0.3 M NaCl were collected.

While the obtained fractions were pooled and dialyzed against PBS, a gel for immunoaffinity chromatography with the monoclonal antibody were prepared according to the method disclosed in Japanese Patent Kokai No.231,598/96 by the same applicant of this invention. After the gel were charged into a plastic column and washed with PBS, the above dialyzed solution was applied to the column. To the column was fed 100 mM glycine-HCl buffer (pH 2.5), and the eluted fractions, which contained a polypeptide capable of inducing the production of INF-γ by immunocompetent cells, were collected. After the collected fractions were dialyzed against sterilized distilled water and concentrated with a membrane filtration, the resultant was lyophilized to obtain a purified solid polypeptide in a yield of about 15 mg/l-culture.

EXAMPLE FOR REFERENCE

Expression in *Escherichia coli*

As disclosed in Japanese Patent Kokai No.193,098/96, a transformant pKHuGF which was obtained by introducing a cDNA with the nucleotide sequence of SEQ ID NO:2 into *Escherichia coli* as a host, was inoculated into L-broth medium containing 50 $\mu$g/ml ampicillin and cultured at 37° C. for 18 hr under shaking conditions. The cells were collected by centrifuging the resulting culture, and then suspended in a mixture solution (pH 7.2) of 139 mM NaCl, 7 mM $NaH_2PO_4$ and 3 mM $Na_2HPO_4$, followed by supersonicating to disrupt the cells. After the cell disruptants were centrifuged, the supernatant was subjected to purifying steps similarly as in Example 4-1 to obtain a purified solid polypeptide in a yield of about 5 mg/l-culture.

Comparing the yields of the polypeptides in Example for Reference and in Example 4-1 shows that the use of a transformant, which is formed by introducing a genomic DNA encoding the present polypeptide into a mammalian cell as a host, strongly elevates the yield of the polypeptide per culture.

Example 4-2

Physicochemical Property of Polypeptide

Example 4-2(a)

Biological Activity

Blood were collected from a healthy donor by using a syringe containing heparin, and then diluted with 2-fold volume of serum-free RPMI-1640 medium (pH 7.4). The blood was overlaid on ficoll, commercialized by Pharmacia LKB Biotechnology AB, Upsalla, Sweden, and centrifuged to obtain lymphocytes, which were then washed with RPMI-1640 medium containing 10 v/v % bovine fetal serum before being suspended in a fresh preparation of the same medium to give a cell density of $5\times10^6$ cells/ml. 0.15 ml aliquots of the cell suspension was distributed into wells of micro plates with 96 wells.

To the wells with the cells were distributed 0.05 ml aliquots of solutions of the polypeptide in Example 4-1, diluted with RPMI-1640 medium (pH 7.4) containing 10 v/v % bovine fetal serum to give desired concentrations. 0.05 ml aliquots of fresh preparations of the same medium with 2.5 μg/ml concanavalin A were further added to the wells, before culturing in a 5 v/v % $CO_2$ incubator at 37° C. for 24 hr. After the cultivation, 0.1 ml of the culture supernatant was collected from each well and examined on IFN-γ by usual enzyme immunoassay. In parallel, a systems as a control using the polypeptide in Reference for that in Example 4-1 or using no polypeptide was treated similarly as above. The results were in Table 1. INF-γ in Table 1 were expressed with international units (IU), calculated based on the INF-γ standard, Gg23-901-530, obtained from the International Institute of Health, USA.

TABLE 1

| Sample of polypeptide | IFN-γ production (IU/ml) |
|---|---|
| Example 4-2(a) | $3.4 \times 10^5$ |
| Example for Reference | $1.7 \times 10^5$ |

Table 1 indicates that the lymphocytes as immunocompetent cells produce IFN-γ by the action of the present polypeptide.

It is more remarkable that the polypeptide in Example 4-1 could induce INF-γ production more than that in Example for Reference. Considering this and the difference in the yields of the polypeptides, described in Example for Reference, it can be presumed: Even if DNAs could be substantially equivalent in encoding the same amino acid sequence, not only the expressing efficiencies of the DNAs may differ, but the products expressed by them may significantly differ in their biological activities as a result of post-translational modifications by intracellular enzymes, depending on types of the DNAs and their hosts; (a) one type is used a transformant formed by introducing a DNA, which is a cDNA, into a microorganisms as a host, and (b) other type is used a transformant formed by introducing the present genomic DNA into a mammalian cell as a host.

Example 4-2(b)

Molecular Weight

SDS-polyacrylamide gel electrophoresis of the polypeptide in Example 4-1 in the presence of 2 w/v % dithiothreitol as a reducing agent, according to the method reported by U. K. Laemli et al., in "Nature", Vol. 227, pp. 680–685 (1970), exhibited a main band of a protein capable of inducing INF-γ in a position corresponding to a molecular weight of about 18,000–19,500 daltons. The molecular weight makers used in the analysis were bovine serum albumin (67,000 daltons), ovalbumin (45,000 daltons), carbonic anhydrase (30,000 daltons), soy bean trypsin inhibitor (20,100 daltons) and α-lactoalbumin (14,000 daltons).

Example 4-2(c)

N-Terminal Amino Acid Sequence

Conventional analysis using "MODEL 473A", a protein sequencer commercialized by Perkin-Elmer Corp., Norwalk, USA, revealed that the polypeptide in Example 4-1 had the amino acid sequence of SEQ ID NO:15 in the N-terminal region.

Judging collectively from this result as well as the information that SDS-polyacrylamide gel electrophresis exhibited a main band in a position corresponding to a molecular weight of about 18,000–19,500 daltons, and that the molecular weight calculated from the amino acid sequence of SEQ ID NO:1 was 18,199 daltons, it can be concluded that the polypeptide in Example 4-1 has the amino acid sequence of SEQ ID NO:6.

As is described above, the present invention is made based on the identification of a genomic DNA encoding the polypeptide which induces the production of INF-γ by immunocompetent cells. The present genomic DNA efficiently express the present polypeptide when introduced into mammalian host cells. The polypeptide features higher biological activities than that obtained by the cDNA expression in *Escherichia coli.* Therefore, the present genomic DNA is useful for the recombinant DNA techniques to prepare the polypeptide capable of inducing INF-γ production by immunocompetent cells. The present genomic DNA is useful to gene therapy for diseases including viral diseases, bacterial-infectious diseases, malignant tumors and immunopathies.

Thus, the present invention is a significant invention which has a remarkable effect and gives a great contribution to this field.

While there has been described what is at present considered to be the preferred embodiments of the present invention, it will be understood the various modifications may be made therein, and it is intended to cover in the appended claims all such modifications as fall within the true spirits and scope of the invention.

We claim:

1. An isolated DNA molecule comprising a nucleotide sequence encoding the amino acid sequence shown in SEQ ID NO:1, where Xaa is isoleucine or threonine, wherein said nucleotide sequence consists of the sequence of a fragment of human genomic DNA.

2. An isolated DNA molecule according to claim 1, wherein said nucleotide sequence comprises an exon having the sequence shown in SEQ ID NO:3, 4, 5, 6, or 7.

3. An isolated DNA molecule according to claim 1, wherein said nucleotide sequence comprises an intron having the sequence shown in SEQ ID NO:8, 9, 10, 11, or 12.

4. The isolated DNA molecule according to claim 1, wherein said nucleotide sequence is the sequence shown in SEQ ID NO:13 or 14.

5. A process for preparing a polypeptide of SEQ ID NO:1, comprising the steps of:

artificially expressing the polypeptide of SEQ ID NO:1, where Xaa represents isoleucine or threonine, from the isolated DNA molecule according to claim 1; and recovering the expressed polypeptide to prepare the polypeptide of SEQ ID NO:1.

6. An autonomously replicable vector into which the isolated DNA molecule according to claim 1 is inserted.

7. A mammalian host cell transformed with the isolated DNA molecule according to claim 1, wherein said transformed host cell is capable of expressing a polypeptide of SEQ ID NO:1, where Xaa represents isoleucine or threonine, in culture.

8. A transformed mammalian host cell according to claim 7, which is selected from the group consisting of an epithelial cell, an interstitial cell and a hemopoietic cell.

9. A process for preparing a polypeptide of SEQ ID NO:1, comprising the steps of:

culturing the transformed mammalian host cell of claim 7 in a nutrient culture medium to express the polypeptide of SEQ ID NO:1, where Xaa represents isoleucine or threonine; and recovering the expressed polypeptide from the culture medium to prepare the polypeptide of SEQ ID NO:1.

10. The process according to claim 9, wherein the polypeptide of SEQ ID NO:1 is recovered by immunoaffinity chromatography with a monoclonal antibody against the polypeptide of SEQ ID NO:1.

11. The process according to claim 9, wherein the polypeptide is recovered by one or more purification techniques selected from the group consisting of salting out, dialysis, filtration, concentrating a solution, separatory sedimentation, ion-exchange chromatography, gel filtration chromatography, adsorption chromatography, isoelectric point chromatography, hydrophobic chromatography, reversed phase chromatography, affinity chromatography, gel electrophoresis, and isolectric focusing.

12. An isolated subgenomic DNA molecule comprising the nucleotide sequence shown in SEQ ID NO:8, 9, 10, 11, or 12.

* * * * *

```
                         SEQUENCE LISTING

(1) GENERAL INFORMATION:

   (iii) NUMBER OF SEQUENCES: 35

(2) INFORMATION FOR SEQ ID NO: 1:
```

-continued (i) SEQUENCE CHARACTERISTICS:
(A) LENGTH: 157 amino acids
(B) TYPE: amino acid
(D) TOPOLOGY: linear (ii) MOLECULE TYPE: peptide (xi) SEQUENCE DESCRIPTION: SEQ ID NO: 1:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Xaa Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

(2) INFORMATION FOR SEQ ID NO: 2:

(i) SEQUENCE CHARACTERISTICS:
(A) LENGTH: 1120 base pairs
(B) TYPE: nucleic acid
(C) STRANDEDNESS: double
(D) TOPOLOGY: linear (ii) MOLECULE TYPE: cDNA to mRNA (iii) HYPOTHETICAL: No (iv) ANTI-SENSE: No (vi) ORIGINAL SOURCE:
(A) ORGANISM: human
(F) TISSUE TYPE: liver (iX) FEATURE:
(A) NAME/KEY: 5'UTR
(B) LOCATION: 1..177
(C) IDENTIFICATION METHOD: E
(A) NAME/KEY: leader peptide
(B) LOCATION: 178..285
(C) IDENTIFICATION METHOD: S
(A) NAME/KEY: mat peptide
(B) LOCATION: 286..756
(C) IDENTIFICATION METHOD: S
(A) NAME/KEY: 3'UTR
(B) LOCATION: 757..1120
(C) IDENTIFICATION METHOD: E (xi) SEQUENCE DESCRIPTION: SEQ ID NO:2:

```
GCCTGGACAG TCAGCAAGGA ATTGTCTCCC AGTGCATTTT GCCCTCCTGG CTGCCAACTC     60

TGGCTGCTAA AGCGGCTGCC ACCTGCTGCA GTCTACACAG CTTCGGGAAG AGGAAAGGAA    120
```

-continued

```
CCTCAGACCT TCCAGATCGC TTCCTCTCGC AACAAACTAT TTGTCGCAGG AATAAAG       177

ATG GCT GCT GAA CCA GTA GAA GAC AAT TGC ATC AAC TTT GTG GCA ATG      225
Met Ala Ala Glu Pro Val Glu Asp Asn Cys Ile Asn Phe Val Ala Met
    -35                 -30                 -25

AAA TTT ATT GAC AAT ACG CTT TAC TTT ATA GCT GAA GAT GAT GAA AAC      273
Lys Phe Ile Asp Asn Thr Leu Tyr Phe Ile Ala Glu Asp Asp Glu Asn
-20                 -15                 -10                 -5

CTG GAA TCA GAT TAC TTT GGC AAG CTT GAA TCT AAA TTA TCA GTC ATA      321
Leu Glu Ser Asp Tyr Phe Gly Lys Leu Glu Ser Lys Leu Ser Val Ile
                1               5                   10

AGA AAT TTG AAT GAC CAA GTT CTC TTC ATT GAC CAA GGA AAT CGG CCT      369
Arg Asn Leu Asn Asp Gln Val Leu Phe Ile Asp Gln Gly Asn Arg Pro
        15                  20                  25

CTA TTT GAA GAT ATG ACT GAT TCT GAC TGT AGA GAT AAT GCA CCC CGG      417
Leu Phe Glu Asp Met Thr Asp Ser Asp Cys Arg Asp Asn Ala Pro Arg
    30                  35                  40

ACC ATA TTT ATT ATA AGT ATG TAT AAA GAT AGC CAG CCT AGA GGT ATG      465
Thr Ile Phe Ile Ile Ser Met Tyr Lys Asp Ser Gln Pro Arg Gly Met
45                  50                  55                  60

GCT GTA ACT ATC TCT GTG AAG TGT GAG AAA ATT TCA AYT CTC TCC TGT      513
Ala Val Thr Ile Ser Val Lys Cys Glu Lys Ile Ser Xaa Leu Ser Cys
                65                  70                  75

GAG AAC AAA ATT ATT TCC TTT AAG GAA ATG AAT CCT CCT GAT AAC ATC      561
Glu Asn Lys Ile Ile Ser Phe Lys Glu Met Asn Pro Pro Asp Asn Ile
            80                  85                  90

AAG GAT ACA AAA AGT GAC ATC ATA TTC TTT CAG AGA AGT GTC CCA GGA      609
Lys Asp Thr Lys Ser Asp Ile Ile Phe Phe Gln Arg Ser Val Pro Gly
        95                  100                 105

CAT GAT AAT AAG ATG CAA TTT GAA TCT TCA TCA TAC GAA GGA TAC TTT      657
His Asp Asn Lys Met Gln Phe Glu Ser Ser Ser Tyr Glu Gly Tyr Phe
    110                 115                 120

CTA GCT TGT GAA AAA GAG AGA GAC CTT TTT AAA CTC ATT TTG AAA AAA      705
Leu Ala Cys Glu Lys Glu Arg Asp Leu Phe Lys Leu Ile Leu Lys Lys
125                 130                 135                 140

GAG GAT GAA TTG GGG GAT AGA TCT ATA ATG TTC ACT GTT CAA AAC GAA      753
Glu Asp Glu Leu Gly Asp Arg Ser Ile Met Phe Thr Val Gln Asn Glu
                145                 150                 155

GAC TAGCTATTAA AATTTCATGC CGGGCGCAGT GGCTCACGCC TGTAATCCCA          806
Asp

GCCCTTTGGG AGGCTGAGGC GGGCAGATCA CCAGAGGTCA GGTGTTCAAG ACCAGCCTGA    866

CCAACATGGT GAAACCTCAT CTCTACTAAA AATACTAAAA ATTAGCTGAG TGTAGTGACG    926

CATGCCCTCA ATCCCAGCTA CTCAAGAGGC TGAGGCAGGA GAATCACTTG CACTCCGGAG    986

GTAGAGGTTG TGGTGAGCCG AGATTGCACC ATTGCGCTCT AGCCTGGGCA ACAACAGCAA   1046

AACTCCATCT CAAAAAATAA AATAAATAAA TAAACAAATA AAAAATTCAT AATGTGAAAA   1106

AAAAAAAAAA AAAA                                                     1120
```

(2) INFORMATION FOR SEQ ID NO: 3:

(i) SEQUENCE CHARACTERISTICS:
- (A) LENGTH: 135 base pairs
- (B) TYPE: nucleic acid
- (C) STRANDEDNESS: double
- (D) TOPOLOGY: linear (ii) MOLECULE TYPE: Genomic DNA -continued (vi) ORIGINAL SOURCE:
(A) ORGANISM: human
(F) TISSUE TYPE: placenta (iX) FEATURE:
(A) NAME/KEY: exon
(B) LOCATION: 1..135
(C) IDENTIFICATION METHOD: S (xi) SEQUENCE DESCRIPTION: SEQ ID NO: 3:

```
 AA AAC CTG GAA TCA GAT TAC TTT GGC AAG CTT GAA TCT AAA TTA TCA       47
Glu Asn Leu Glu Ser Asp Tyr Phe Gly Lys Leu Glu Ser Lys Leu Ser
     -5                   1               5                  10

GTC ATA AGA AAT TTG AAT GAC CAA GTT CTC TTC ATT GAC CAA GGA AAT       95
Val Ile Arg Asn Leu Asn Asp Gln Val Leu Phe Ile Asp Gln Gly Asn
                15                  20                  25

CGG CCT CTA TTT GAA GAT ATG ACT GAT TCT GAC TGT AGA G                135
Arg Pro Leu Phe Glu Asp Met Thr Asp Ser Asp Cys Arg Asp
            30                  35                  40
```

(2) INFORMATION FOR SEQ ID NO: 4:

(i) SEQUENCE CHARACTERISTICS:
(A) LENGTH: 134 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: exon
(B) LOCATION: 1..134
(C) IDENTIFICATION METHOD: S (xi) SEQUENCE DESCRIPTION: SEQ ID NO: 4:

```
 AT AAT GCA CCC CGG ACC ATA TTT ATT ATA AGT ATG TAT AAA GAT AGC       47
Asp Asn Ala Pro Arg Thr Ile Phe Ile Ile Ser Met Tyr Lys Asp Ser
40                  45                  50                  55

CAG CCT AGA GGT ATG GCT GTA ACT ATC TCT GTG AAG TGT GAG AAA ATT       95
Gln Pro Arg Gly Met Ala Val Thr Ile Ser Val Lys Cys Glu Lys Ile
                60                  65                  70

TCA ACT CTC TCC TGT GAG AAC AAA ATT ATT TCC TTT AAG                  134
Ser Thr Leu Ser Cys Glu Asn Lys Ile Ile Ser Phe Lys
            80                  85
```

(2) INFORMATION FOR SEQ ID NO: 5:

(i) SEQUENCE CHARACTERISTICS:
(A) LENGTH: 87 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: exon
(B) LOCATION: 1..87
(C) IDENTIFICATION METHOD: S (xi) SEQUENCE DESCRIPTION: SEQ ID NO: 5:

-continued

```
GAATAAAG ATG GCT GCT GAA CCA GTA GAA GAC AAT TGC ATC AAC TTT GTG       50
         Met Ala Ala Glu Pro Val Glu Asp Asn Cys Ile Asn Phe Val
             -35                 -30                 -25

GCA ATG AAA TTT ATT GAC AAT ACG CTT TAC TTT ATA G                      87
Ala Met Lys Phe Ile Asp Asn Thr Leu Tyr Phe Ile Ala
        -20                 -15                 -10
```

(2) INFORMATION FOR SEQ ID NO:6:

(i) SEQUENCE CHARACTERISTICS:
(A) LENGTH: 12 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: exon
(B) LOCATION: 1..87
(C) IDENTIFICATION METHOD: S (xi) SEQUENCE DESCRIPTION: SEQ ID NO: 6:

```
 CT GAA GAT GAT G                                                      12
Ala Glu Asp Asp Glu
-10
```

(2) INFORMATION FOR SEQ ID NO: 7:

(i) SEQUENCE CHARACTERISTICS:
(A) LENGTH: 2167 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: exon + 3'UTR
(B) LOCATION: 1..2167
(C) IDENTIFICATION METHOD: E (xi) SEQUENCE DESCRIPTION: SEQ ID NO: 7:

```
GAA ATG AAT CCT CCT GAT AAC ATC AAG GAT ACA AAA AGT GAC ATC ATA        48
Glu Met Asn Pro Pro Asp Asn Ile Lys Asp Thr Lys Ser Asp Ile Ile
85                  90                  95                  100

TTC TTT CAG AGA AGT GTC CCA GGA CAT GAT AAT AAG ATG CAA TTT GAA        96
Phe Phe Gln Arg Ser Val Pro Gly His Asp Asn Lys Met Gln Phe Glu
                105                 110                 115

TCT TCA TCA TAC GAA GGA TAC TTT CTA GCT TGT GAA AAA GAG AGA GAC       144
Ser Ser Ser Tyr Glu Gly Tyr Phe Leu Ala Cys Glu Lys Glu Arg Asp
            120                 125                 130

CTT TTT AAA CTC ATT TTG AAA AAA GAG GAT GAA TTG GGG GAT AGA TCT       192
Leu Phe Lys Leu Ile Leu Lys Lys Glu Asp Glu Leu Gly Asp Arg Ser
        135                 140                 145

ATA ATG TTC ACT GTT CAA AAC GAA GAC TAGCTAT TAAAATTTCA TGCCGGGCGC     246
Ile Met Phe Thr Val Gln Asn Glu Asp
    150                 155

AGTGGCTCAC GCCTGTAATC CCAGCCCTTT GGGAGGCTGA GGCGGGCAGA TCACCAGAGG     306
```

-continued

```
TCAGGTGTTC AAGACCAGCC TGACCAACAT GGTGAAACCT CATCTCTACT AAAAATACAA    366

AAAATTAGCT GAGTGTAGTG ACCCATGCCC TCAATCCCAG CTACTCAAGA GGCTGAGGCA    426

GGAGAATCAC TTGCACTCCG GAGGTGGAGG TTGTGGTGAG CCGAGATTGC ACCATTGCGC    486

TCTAGCCTGG GCAACAACAG CAAAACTCCA TCTCAAAAAA TAAAATAAAT AAATAAACAA    546

ATAAAAAATT CATAATGTGA ACTGTCTGAA TTTTTATGTT TAGAAAGATT ATGAGATTAT    606

TAGTCTATAA TTGTAATGGT GAAATAAAAT AAATACCAGT CTTGAAAAAC ATCATTAAGA    666

AATGAATGAA CTTTCACAAA AGCAAACAAA CAGACTTTCC CTTATTTAAG TGAATAAAAT    726

AAAATAAAAT AAAATAATGT TTAAAAAATT CATAGTTTGA AAACATTCTA CATTGTTAAT    786

TGGCATATTA ATTATACTTA ATATAATTAT TTTTAAATCT TTTGGGTTAT TAGTCCTAAT    846

GACAAAAGAT ATTGATATTT GAACTTTCTA ATTTTTAAGA ATATCGTTAA ACCATCAATA    906

TTTTTATAAG GAGGCCACTT CACTTGACAA ATTTCTGAAT TTCCTCCAAA GTCAGTATAT    966

TTTTAAAATT CAGTTTGATC CTGAATCCAG CAATATATAA AAGGGATTAT ATACTCTGGC   1026

CAACTGACAT TCATCCTAGG AATGCAAAGA TGGTTTAATA TCCTAAAATC AATTAACATA   1086

ACATACTATA TTAATAAAGT ATCAAAACAG TATTCTCATC TTTTTTTCTT TTTTCACAAT   1146

TCCTTGGTTA CACTATCATC TCAATAGATG CAGAAAAAGC ATTTGACAAA ATCCAATTCA   1206

TAATAAAAAT TCTCAAACTT GAAAGAGAAC ATCATAAAGG CATCTATGAA AAACCTACAG   1266

CTAATATCAT ACTTAACGAT GAAAAACTGA ATTATTTTAC CCTAAGATCA AGAATAATGC   1326

AAGCATGTCA GCTCTTGCAA CTTCTATTCA ACATTGTACT GGAGGTTCTA GCCAGAGCAA   1386

CCATACAATA AATAAAAATA AAAGGCACCC AGATTAGAAA GGAAGTCTTT ATTTGCAGAC   1446

AACATGGTTC TTTATGCAGA AAACCGTCAG GAATACACAC ACATGTTAGA ACTAATAAGT   1506

TCAGCAAGGT TGCAGGTTGC AATATCAATA TGCAAAAATA CATTGAAGGC TGGGCTCAGT   1566

GGAGATGGCA TGTACCTTTC GTCCCAGCTA CTTGGGAGGC TGAGGTAGGA GGATCACTTG   1626

AGGTGAGGAG TTTGAGGCTA TAGTGCAATG TGATCTTGCC TGTGAATAGC CACTGCACTC   1686

GAGCCTAGGC AACAAAGTGA GACCCCGTCT CCAAAAAAAA AAATGGTATA TTGGTATTTC   1746

TGTATATGAA CAATGAATGA TCTGAAAACA AGAAAATTCC ATTCACGATG GTATTAAAAA   1806

AATAAAATAC AAATAAATTT AGCAAAATAA TTATAAAACT TGTACATCGA AAATTTCAAA   1866

GCACTCTGAG GGAAATTAAA GATGATCTAA ATAATTGGAG AGACACTCTA TGATCACTGA   1926

TTGGAAAATT CATTCAATAT TGTTAAGATA ACAATTGTCC CCAAATTGAT GCATGCATTC   1986

AATTTAGTCT TCATCAAAAT TCCAGCAGGG TTTTTGCAGA AATTGACAAG CTGTACCCAA   2046

AATGTATATG GAAATGAAAA GACCCAGAAG AGCAAATAAT TTTTTAAAAA CAAAGTTGGA   2106

AAACTTTTAC TTCCTAATTT TAAAACTTAC TATAAACCTA AAGTTATCAA GACCATTTAG   2166

T                                                                   2167
```

(2) INFORMATION FOR SEQ ID NO: 8:

(i) SEQUENCE CHARACTERISTICS:
(A) LENGTH: 1334 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta -continued (iX) FEATURE:
(A) NAME/KEY: intron
(B) LOCATION: 1..1334
(C) IDENTIFICATION METHOD: E (xi) SEQUENCE DESCRIPTION: SEQ ID NO: 8:

```
GTATTTTTTT TAATTCGCAA ACATAGAAAT GACTAGCTAC TTCTTCCCAT TCTGTTTTAC     60

TGCTTACATT GTTCCGTGCT AGTCCCAATC CTCAGATGAA AAGTCACAGG AGTGACAATA    120

ATTTCACTTA CAGGAAACTT TATAAGGCAT CCACGTTTTT TAGTTGGGGT AAAAAATTGG    180

ATACAATAAG ACATTGCTAG GGGTCATGCC TCTCTGAGCC TGCCTTTGAA TCACCAATCC    240

CTTTATTGTG ATTGCATTAA CTGTTTAAAA CCTCTATAGT TGGATGCTTA ATCCCTGCTT    300

GTTACAGCTG AAAATGCTGA TAGTTTACCA GGTGTGGTGG CATCTATCTG TAATCCTAGC    360

TACTTGGGAG GCTCAAGCAG GAGGATTGCT TGAGGCCAGG ACTTTGAGGC TGTAGTACAC    420

TGTGATCGTA CCTGTGAATA GCCACTGCAC TCCAGCCTGG GTGATATACA GACCTTGTCT    480

CTAAAATTAA AAAAAAAAAA AAAAAAAACC TTAGGAAAGG AAATTGATCA AGTCTACTGT    540

GCCTTCCAAA ACATGAATTC CAAATATCAA AGTTAGGCTG AGTTGAAGCA GTGAATGTGC    600

ATTCTTTAAA AATACTGAAT ACTTACCTTA ACATATATTT TAAATATTTT ATTTAGCATT    660

TAAAAGTTAA AAACAATCTT TTAGAATTCA TATCTTTAAA ATACTCAAAA AAGTTGCAGC    720

GTGTGTGTTG TAATACACAT TAAACTGTGG GGTTGTTTGT TTGTTTGAGA TGCAGTTTCA    780

CTCTGTCACC CAGGCTGAAG TGCAGTGCAG TGCAGTGGTG TGATCTCGGC TCACTACAAC    840

CTCCACCTCC CACGTTCAAG CGATTCTCAT GCCTCAGTCT CCCGAGTAGG TGGGATTACA    900

GGCATGCACC ACTTACACCC GGCTAATTTT TGTATTTTTA GTAGAGCTGG GGTTTCACCA    960

TGTTGGCCAG GCTGGTCTCA AACCCCTAAC CTCAAGTGAT CTGCCTGCCT CAGCCTCCCA   1020

AACAAACAAA CAACCCCACA GTTTAATATG TGTTACAACA CACATGCTGC AACTTTTATG   1080

AGTATTTTAA TGATATAGAT TATAAAAGGT TGTTTTTAAC TTTTAAATGC TGGGATTACA   1140

GGCATGAGCC ACTGTGCCAG GCCTGAACTG TGTTTTTAAA AATGTCTGAC CAGCTGTACA   1200

TAGTCTCCTG CAGACTGGCC AAGTCTCAAA GTGGGAACAG GTGTATTAAG GACTATCCTT   1260

TGGTTAAATT TCCGCAAATG TTCCTGTGCA AGAATTCTTC TAACTAGAGT TCTCATTTAT   1320

TATATTTATT TCAG                                                      1334
```

(2) INFORMATION FOR SEQ ID NO: 9:

(i) SEQUENCE CHARACTERISTICS:
(A) LENGTH: 4773 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: intron
(B) LOCATION: 1..4773
(C) IDENTIFICATION METHOD: E (xi) SEQUENCE DESCRIPTION: SEQ ID NO: 9:

```
GTAAGACTGA GCCTTACTTT GTTTTCAATC ATGTTAATAT AATCAATATA ATTAGAAATA     60

TAACATTATT TCTAATGTTA ATATAAGTAA TGTAATTAGA AAACTCAAAT ATCCTCAGAC    120
```

-continued

```
CAACCTTTTG TCTAGAACAG AAATAACAAG AAGCAGAGAA CCATTAAAGT GAATACTTAC    180
TAAAAATTAT CAAACTCTTT ACCTATTGTG ATAATGATGG TTTTTCTGAG CCTGTCACAG    240
GGGAAGAGGA GATACAACAC TTGTTTTATG ACCTGCATCT CCTGAACAAT CAGTCTTTAT    300
ACAAATAATA ATGTAGAATA CATATGTGAG TTATACATTT AAGAATAACA TGTGACTTTC    360
CAGAATGAGT TCTGCTATGA AGAATGAAGC TAATTATCCT TCTATATTTC TACACCTTTG    420
TAAATTATGA TAATATTTTA ATCCCTAGTT GTTTTGTTGC TGATCCTTAG CCTAAGTCTT    480
AGACACAAGC TTCAGCTTCC AGTTGATGTA TGTTATTTTT AATGTTAATC TAATTGAATA    540
AAAGTTATGA GATCAGCTGT AAAAGTAATG CTATAATTAT CTTCAAGCCA GGTATAAAGT    600
ATTTCTGGCC TCTACTTTTT CTCTATTATT CTCCATTATT ATTCTCTATT ATTTTTCTCT    660
ATTTCCTCCA TTATTGTTAG ATAAACCACA ATTAACTATA GCTACAGACT GAGCCAGTAA    720
GAGTAGCCAG GGATGCTTAC AAATTGGCAA TGCTTCAGAG GAGAATTCCA TGTCATGAAG    780
ACTCTTTTTG AGTGGAGATT TGCCAATAAA TATCCGCTTT CATGCCCACC CAGTCCCCAC    840
TGAAAGACAG TTAGGATATG ACCTTAGTGA AGGTACCAAG GGGCAACTTG GTAGGGAGAA    900
AAAAGCCACT CTAAAATATA ATCCAAGTAA GAACAGTGCA TATGCAACAG ATACAGCCCC    960
CAGACAAATC CCTCAGCTAT CTCCCTCCAA CCAGAGTGCC ACCCCTTCAG GTGACAATTT   1020
GGAGTCCCCA TTCTAGACCT GACAGGCAGC TTAGTTATCA AAATAGCATA AGAGGCCTGG   1080
GATGGAAGGG TAGGGTGGAA AGGGTTAAGC ATGCTGTTAC TGAACAACAT AATTAGAAGG   1140
GAAGGAGATG GCCAAGCTCA AGCTATGTGG GATAGAGGAA AACTCAGCTG CAGAGGCAGA   1200
TTCAGAAACT GGGATAAGTC CGAACCTACA GGTGGATTCT TGTTGAGGGA GACTGGTGAA   1260
AATGTTAAGA AGATGGAAAT AATGCTTGGC ACTTAGTAGG AACTGGGCAA ATCCATATTT   1320
GGGGGAGCCT GAAGTTTATT CAATTTTGAT GGCCCTTTTA AATAAAAAGA ATGTGGCTGG   1380
GCGTGGTGGC TCACACCTGT AATCCCAGCA CTTTGGGAGG CCGAGGGGGG CGGATCACCT   1440
GAAGTCAGGA GTTCAAGACC AGCCTGACCA ACATGGAGAA ACCCCATCTC TACTAAAAAT   1500
ACAAAATTAG CTGGGCGTGG TGGCATATGC CTGTAATCCC AGCTACTCGG GAGGCTGAGG   1560
CAGGAGAATC TTTTGAACCC GGGAGGCAGA GGTTGCGATG AGCCTAGATC GTGCCATTGC   1620
ACTCCAGCCT GGGCAACAAG AGCAAAACTC GGTCTCAAAA AAAAAAAAAA AAAAGTGAAA   1680
TTAACCAAAG GCATTAGCTT AATAATTTAA TACTGTTTTT AAGTAGGGCG GGGGGTGGCT   1740
GGAAGAGATC TGTGTAAATG AGGGAATCTG ACATTTAAGC TTCATCAGCA TCATAGCAAA   1800
TCTGCTTCTG GAAGGAACTC AATAAATATT AGTTGGAGGG GGGGAGAGAG TGAGGGGTGG   1860
ACTAGGACCA GTTTTAGCCC TTGTCTTTAA TCCCTTTTCC TGCCACTAAT AAGGATCTTA   1920
GCAGTGGTTA TAAAAGTGGC CTAGGTTCTA GATAATAAGA TACAACAGGC CAGGCACAGT   1980
GGCTCATGCC TATAATCCCA GCACTTTGGG AGGGCAAGGC GAGTGTCTCA CTTGAGATCA   2040
GGAGTTCAAG ACCAGCCTGG CCAGCATGGC GATACTCTGT CTCTACTAAA AAAAATACAA   2100
AAATTAGCCA GGCATGGTGG CATGCACCTG TAATCCCAGC TACTCGTGAG CCTGAGGCAG   2160
AAGAATCGCT TGAAACCAGG AGGTGTAGGC TGCAGTGAGC TGAGATCGCA CCACTGCACT   2220
CCAGCCTGGG CGACAGAATG AGACTTTGTC TCAAAAAAAG AAAAAGATAC AACAGGCTAC   2280
CCTTATGTGC TCACCTTTCA CTGTTGATTA CTAGCTATAA AGTCCTATAA AGTTCTTTGG   2340
TCAAGAACCT TGACAACACT AAGAGGGATT TGCTTTGAGA GGTTACTGTC AGAGTCTGTT   2400
TCATATATAT ACATATACAT GTATATATGT ATCTATATCC AGGCTTGGCC AGGGTTCCCT   2460
```

-continued

```
CAGACTTTCC AGTGCACTTG GGAGATGTTA GGTCAATATC AACTTTCCCT GGATTCAGAT   2520

TCAACCCCTT CTGATGTAAA AAAAAAAAAA AAAAAGAAAG AAATCCCTTT CCCCTTGGAG   2580

CACTCAAGTT TCACCAGGTG GGGCTTTCCA AGTTGGGGGT TCTCCAAGGT CATTGGGATT   2640

GCTTTCACAT CCATTTGCTA TGTACCTTCC CTATGATGGC TGGGAGTGGT CAACATCAAA   2700

ACTAGGAAAG CTACTGCCCA AGGATGTCCT TACCTCTATT CTGAAATGTG CAATAAGTGT   2760

GATTAAAGAG ATTGCCTGTT CTACCTATCC ACACTCTCGC TTTCAACTGT AACTTTCTTT   2820

TTTTCTTTTT TTCTTTTTTT CTTTTTTTTT GAAACGGAGT CTCGCTCTGT CGCCCAGGCT   2880

AGAGTGCAGT GGCACGATCT CAGCTCACTG CAAGCTCTGC CTCCCGGGTT CACGCCATTC   2940

TCCTGCCTCA CCCTCCCAAG CAGCTGGGAC TACAGGCGCC TGCCACCATG CCCAGCTAAT   3000

TTTTTGTATT TTTAGTAGAG ACGGGGTTTC ACCGTGTTAG CCAGGATGGT CTCGATCTCC   3060

TGAACTTGTG ATCCGCCCGC CTCAGCCTCC CAAAGTGCTG GGATTACAGG CGTGAGCCAT   3120

CGCACCCGGC TCAACTGTAA CTTTCTATAC TGGTTCATCT TCCCCTGTAA TGTTACTAGA   3180

GCTTTTGAAG TTTTGGCTAT GGATTATTTC TCATTTATAC ATTAGATTTC AGATTAGTTC   3240

CAAATTGATG CCCACAGCTT AGGGTCTCTT CCTAAATTGT ATATTGTAGA CAGCTGCAGA   3300

AGTGGGTGCC AATAGGGGAA CTAGTTTATA CTTTCATCAA CTTAGGACCC ACACTTGTTG   3360

ATAAAGAACA AAGGTCAAGA GTTATGACTA CTGATTCCAC AACTGATTGA GAAGTTGGAG   3420

ATAACCCCGT GACCTCTGCC ATCCAGAGTC TTTCAGGCAT CTTTGAAGGA TGAAGAAATG   3480

CTATTTTAAT TTTGGAGGTT TCTCTATCAG TGCTTAGGAT CATGGGAATC TGTGCTGCCA   3540

TGAGGCCAAA ATTAAGTCCA AAACATCTAC TGGTTCCAGG ATTAACATGG AAGAACCTTA   3600

GGTGGTGCCC ACATGTTCTG ATCCATCCTG CAAAATAGAC ATGCTGCACT AACAGGAAAA   3660

GTGCAGGCAG CACTACCAGT TGGATAACCT GCAAGATTAT AGTTTCAAGT AATCTAACCA   3720

TTTCTCACAA GGCCCTATTC TGTGACTGAA ACATACAAGA ATCTGCATTT GGCCTTCTAA   3780

GGCAGGGCCC AGCCAAGGAG ACCATATTCA GGACAGAAAT TCAAGACTAC TATGGAACTG   3840

GAGTGCTTGG CAGGGAAGAC AGAGTCAAGG ACTGCCAACT GAGCCAATAC AGCAGGCTTA   3900

CACAGGAACC CAGGGCCTAG CCCTACAACA ATTATTGGGT CTATTCACTG TAAGTTTTAA   3960

TTTCAGGCTC CACTGAAAGA GTAAGCTAAG ATTCCTGGCA CTTTCTGTCT CTCTCACAGT   4020

TGGCTCAGAA ATGAGAACTG GTCAGGCCAG GCATGGTGGC TTACACCTGG AATCCCAGCA   4080

CTTTGGGAGG CCGAAGTGGG AGGGTCACTT GAGGCCAGGA GTTCAGGACC AGCTTAGGCA   4140

ACAAAGTGAG ATACCCCCTG ACCCCTTCTC TACAAAAATA AATTTTAAAA ATTAGCCAAA   4200

TGTGGTGGTG TATACTTACA GTCCCAGCTA CTCAGGAGGC TGAGGCAGGG GGATTGCTTG   4260

AGCCCAGGAA TTCAAGGCTG CAGTGAGCTA TGATTTCACC ACTGCACTTC TGGCTGGGCA   4320

ACAGAGCGAG ACCCTGTCTC AAAGCAAAAA GAAAAAGAAA CTAGAACTAG CCTAAGTTTG   4380

TGGGAGGAGG TCATCATCGT CTTTAGCCGT GAATGGTTAT TATAGAGGAC AGAAATTGAC   4440

ATTAGCCCAA AAAGCTTGTG GTCTTTGCTG GAACTCTACT TAATCTTGAG CAAATGTGGA   4500

CACCACTCAA TGGGAGAGGA GAGAAGTAAG CTGTTTGATG TATAGGGGAA AACTAGAGGC   4560

CTGGAACTGA ATATGCATCC CATGACAGGG AGAATAGGAG ATTCGGAGTT AAGAAGGAGA   4620

GGAGGTCAGT ACTGCTGTTC AGAGATTTTT TTTATGTAAC TCTTGAGAAG CAAAACTACT   4680

TTTGTTCTGT TTGGTAATAT ACTTCAAAAC AAACTTCATA TATTCAAATT GTTCATGTCC   4740

TGAAATAATT AGGTAATGTT TTTTTCTCTA TAG                                4773
```

-continued (2) INFORMATION FOR SEQ ID NO: 10:

(i) SEQUENCE CHARACTERISTICS:
(A) LENGTH: 8835 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: intron
(B) LOCATION: 1..8835
(C) IDENTIFICATION METHOD: E (xi) SEQUENCE DESCRIPTION: SEQ ID NO: 10:

```
GTAAGAAATA TCATTCCTCT TTATTTGGAA AGTCAGCCAT GGCAATTAGA GGTAAATAAG     60

CTAGAAAGCA ATTGAGAGGA ATATAAACCA TCTAGCATCA CTACGATGAG CAGTCAGTAT    120

CAACATAAGA AATATAAGCA AAGTCAGAGT AGAATTTTTT TCTTTTATCA GATATGGGAG    180

AGTATCACTT TAGAGGAGAG GTTCTCAAAC TTTTTGCTCT CATGTTCCCT TTACACTAAG    240

CACATCACAT GTTAGCATAA GTAACATTTT TAATTAAAAA TAACTATGTA CTTTTTTAAC    300

AACAAAAAAA AGCATAAAGA GTGACACTTT TTTATTTTTA CAAGTGTTTT AACTGGTTTA    360

ATAGAAGCCA TATAGATCTG CTGGATTCTC ATCTGCTTTG CATTCAGACT ACTGCAATAT    420

TGCACAGAAT GCAGCCTCTG GTAAACTCTG TTGTACACTC ATGAGAGAAT GGGTGAAAAA    480

GACAAATTAC GTCTTAGAAT TATTAGAAAT AGCTTTCACT TTAGGAACTC CCTGAGAATT    540

GCTGCTTTAG AGTGGTAAGA TAAATAAGCT TCTCTTTAAA CGGAATCTCA AGACAGAATC    600

AGTTACATTA AAAGCAAACA AAAAATTTGC CCATGGTTAG TCATCTTGTG AAATCTGCCA    660

CACCTTTGGA CTGGGCTACA ATTGGATAAT ATAGCATTCC CCGAGATAAT TTTCTCTCAC    720

AATTAAGGAA AGGGCTGAAT AAATATCTCT GTTTGAAGTT GAATAACAAA AATTAGGACC    780

CCCTAAATTT TAGGGCTCCT GAAATTCGTC TTTTTGCCTA TATTCAGCTA CTTTACGTTC    840

TATTAAATCT TCTTTCAGGC CAGGTGCACT AGCTCATGCC TAGAATCTCA GGCAGGCCTG    900

AGCCCAGGAA TTTGAGACCA GCCAGGGCAA CACAGTCTCT ACAAAAAAAT AAAAAATTAC    960

CTGGGTGTGT TGGTGCATGC CTGTAGAACT ACTCAGGATG CTGAGGACTG CTTGAGCCCA   1020

GGATAGCCAA ATCTGTGGTG AGTTCAGCCA CTAAACAGAG CGAGACTTTC TCAAAAAAAC   1080

AAACAAAAAA ACAAACAAAC TTCCTTCAAA ATAACTTTTT ATCTGCAATG TTTTCCTATT   1140

GCCTGTGAGA TTAAATTTAC TCTTTTACCT GATTTCCAAA GCCCTCCATA ATCTAATCCG   1200

ACTTTACCTT GTGTTCACTG CAAAATAGCA GGACTGTTCC ACTACAATCC AAAAATCACA   1260

GGTTGGGTGC AGTGGCTCAC TCCTGTAATC CCAACACTTT GGAAGGCCAA GGCAGGTGGA   1320

TTGCTTCAGC TCAGGAGTTC AAGACCAGCC TGGGCAACAT GGCAAAAACC CTGTCTCTCC   1380

AAAACATACA AAAATTAGCC AGATGTGGTA GTATGTGCCT GTAGTCCCAA CTACTCAAAA   1440

GGCTAAGGCA AGAGGATCAC TTGAGCCCAG GAGGTCAAGG CTACAGTGAG CCATGTTTAC   1500

TGTGTCACTG CACTCCAGCC TGGGTGATAG AGCAAGACCA TGTCTCAAAA AAAAAAAAAA   1560

GAAAAGAAAA GAAAAAAACA TCGCTCTATT CAGTTCACCC CCACCACAAC ATTGTTTTGA   1620

TTATCACATA AATGCTGGTC CATTGCCTTC TCTATCTATT CAAATCTTTA AGCATTCTTT   1680

GAGATTCAAC TCAATTCTCC TTTTCAAACT AGGCCATTTA AACTACATCA GTTCCATTTT   1740
```

-continued

```
GATTTTCTTG CTTTGAGTCT ACAGACTCAA AAACAAAAAC TTAAAAACTT ATTTTTTAAG   1800
TTTTCTGCTA CTCTCACTTC TTCAACACTC ACATACACGC ATTCATAATA AGATGGCAGA   1860
ATGTTCAAGG ATAAAATGAT TTATAGAACT GAAAAGTTAG GTTTTGATCT TGTTGCTGTC   1920
AAGATGACTA CCTACCTGAT CTCAGGTAAT TAATTATGTA GCATGCTCCC TCATTTCATC   1980
CCATACCTAT TCAACAGGAT TGGAATTCCA CAGCAAGGAT AAACATAATC ATAGTTGCTT   2040
TTCAAGTTCA AGGCATTTTA ACTTTTAATC TAGTAGTATG TTTGTTGTTG TTGTTGTTGT   2100
TTGAGATGGA GCCCTGCTGT GTCACCCAGG CTGGAGTGCA GTGGCACGAA CTCGGCTCAC   2160
TGCAACCTCT GCCTCATGGG TTCAATCAGT TATTCTGCCT CAGTGTCCCA AGTAGCTGGG   2220
ACTACAAGGC ACATGCCACC ATGCCTGGCT AATTTTTGTA TTTTTAGTAG AAACAGGGCT   2280
TCACCATGTT GGCCAGGCTG GTCTCGAACT CCTGACCTCA AGTGATCCAG CCGCCTCGGC   2340
CTCCCAAAGT GCTGGGATTA CAGGCATAAG CCACCGTGCC CAGCCTAATA GTATGTTTTT   2400
AAACTCTTAG TGGCTTAACA ATGCTGGTTG TATAATAAAT ATGCCATAAA TATTTACTGT   2460
CTTAGAATTA TGAAGAAGTG GTTACTAGGC CGTTTGCCAC ATATCAATGG TTCTCTCCTT   2520
ACAGCTTTAA TTAGAGTCTA GAATTGCAGG TTGGTAGAGC TGGAACAGAC CTTAAAGATT   2580
GACTAGCCAA CTTCCTTGTC CAAATGAGGG AACTGAGACC CTTAAAATTA AGTGACTTGC   2640
CCCAGACAAA ACTGGAACTC ATGTGTCCTA ATTTCCATCA TGAAATTCTA CCATTCACTA   2700
GCCTCTGGCT AGTTGTCAAA GTATTGCATA ACTAAATTTT TATGTCTGTT TTAAAGAACA   2760
AATTGTCACT GCTTACTCCT GGGAGGGTCT TTCTGAGGTG GTTTATAACT CTTAAAAAAA   2820
AAAAAGTCAG TAGTCTGAGA ATTTTAGACG AAATAGTCAA AGCATTTTTA TCCAATGGAT   2880
CTATAATTTT CATAGATTAG AGTTAAATCA AAGAAACACG GATGAGAAAG GAAGAGGAAA   2940
ATTGAGGAGA GGAGGAATGG GGATGAGAAC ACACTACTTG TAATCAGTCA TAGATGTACT   3000
GAGAACTAAC AAGAAGAATT GTAAGAAAAT AAGAATGAAG AATTCAAAAT CAACACATGA   3060
AATAAAAAGA AACTACTAGG GAAAAATGGA GAAGACATTA GAAAAATTAT TCTATTTTTA   3120
AAATTCTGTT TTCAGGCTTC CCTCCTGTTC TTCCTCCTTC TCATTGGTTT TCAGGTGGAG   3180
GGAAAGTTTA AGATGGAAAA AATATATATA TTCTACACAT CCCTTTCTAC GCTGTTGTCA   3240
TGGCAACAAG GTTTATCATA GCAAACTTTT ATTCATACAA CATTTATTGA GTTCTTACTG   3300
TGTGGTAAGC TCTTTCCAGG TGTTGAAAAT TCAGGGGAAA AAGACAACT CATTGTCTTA   3360
AAACTCAGAT GAAAGCTGAA CAGACCTATT TTTAATCAAA GTAATCTCAA TTTAGGGTAG   3420
TAAGAGCTAT TTAAGAAGCA TGAACAGGTG TGAAGGAGGT AGGACTCTGA GGAGAGAATA   3480
GTTAGCTAGG AATGAAAGAG CAGAGAAGTT TTCCTAGAGG AACTATTAAA GCTGGGAGTT   3540
ACGGGATGAA AGATGAGGCA GGGTTTGCAG GCAAAAAAAA AAAAAAGGCA GGGGAAGGGG   3600
AAGTTCTGGC CTGGCAGAGA GAATAACTGT GGCAACAATG GAGGAGAGTC TGGAAGCAAG   3660
AAAACCAAGT AGAAGAGTAT TAAAATAGAA GATGCCAGGG GTAATGAGGG CTTGATTTAA   3720
AACAGTGCTG TTGGAGATGG AGAGGAGATA CCAAATTCTG GAGACATTTC TGAGTTAGAA   3780
CCTACAGTAT TTATCAGACA AGGGAAAGAT TAGACAAAGG AGTTAAGAAT GACTCCCAGG   3840
TTTCAGTTTG GGGCAGGTAA CTAGGACATG TTTTGAAAAG TAATGTATTG GATCTCTTAC   3900
CATTGGAACT ATGTATGTGG AGCCAAATTA AAATTTGTAC ATGTATATAA CTCTCCCCCC   3960
ACCACCAGTA ACTACTTCCC TAACTCTCTA CTTTGTAGCC AGACTTCCTA AAAGAATAGT   4020
TTGTAGTCAC TGTCTTTACT TTTCCCCTCC CATTCTGTCC TAGATATTTG TCCACCTACC   4080
```

-continued

```
ATCTGCTGCC TCCACTTTAC CCAAACTGTT CTACGGTTGC CCAAAACTTC CTAATTGCCA   4140
AATTCAATGA ACAAGTTTAA GCTTATATGT AAATTAGGAG CTCTACAGTT TGATTTCGAG   4200
CAGCCCCTCC TGAAACCCTT TCTCTTTCGA CTTCTGTGAC ACATCTCAGA TTTACAAAAC   4260
TGAACTAATT ATTTTACACT TGAGCTGTAT TTTCGTTCTT CTTTCTTGAT GAATGAGGTA   4320
ACCACTCAAC AAATTGCCCA AGCCAAAAAC TACGAAGTCA TCCTCAGTTC CTCCTTCTTC   4380
TGTTTGACCC ACAACAGATC AGCTGAGAAA TCCCGCTGTT TAGTATCTCT TGAATTCATT   4440
ACCTTAATTT ATAGCCTCAT CAACTCTTAA TTGTTAAAAT TACTTCAGTA GTTGTTGTCT   4500
GACCTCTGTC CAATCTTGTT CAATCAGGTC CATTCTTTTG TTCTTGGTGG TGGTGGTGGT   4560
GTTGACAGAG TTTCGCTTTT GCTGCCCAGG CTGAAGTGCA GTGGAGCACT TCACTGCAAC   4620
CACAGCCTCC TGGGTTTAAG CAGTTCACCC TCCCGAGTAG CTGGGACTAC AGGTATGTGC   4680
CACCACACCC AGCTAATTTT GTGTTTTCAG TAGAGACAGG GTTTCACCAT GTTGGTCAGG   4740
CTGGTCTCAA ACTCCTGACC TCAAGCAATC CACCCACCTC AGCCTCCCAA AGTGCTGGGA   4800
TTACAGGCAT GAGCCACTGC ACACGGACCA GATCCATTGT TTATGTTGCT TCTAGAGTGA   4860
GTTTTTAAAA CACAAATTTG ACCATATCTT TCTCCAATTT AAGTCAGTAT TTTTTTTTTC   4920
AGGAAAAAAC AGTTCAAACT CTTTAGTCTG CTTACACAAG GCCTTTGTAG TCTGACTCTT   4980
CTTTCCAAGC TTTCATCAAA GTATACTGCA AGTTACATTT TATGTGAATT GAATTAGGCA   5040
ACGGTATAAA AATTATAGTT TATATGGGCA AAATGGAAAT AATGTTAACT CTTCCAAATA   5100
GTTTATCTAG AATGACATAA TTTCAAAGCT GTCAGGTCAA ATGAGTTATA AACTGTTAAC   5160
ACTATTGCCA CATGCAAGTG TCTCTTATAC TTGGTAGAAT TATCTGCTTC CATGTCATTA   5220
TTATGTAAAT TAGACTTTAA ATAACTCAGA AGTTCTTCAG ACATACAGGT TATTATTGTG   5280
CTTTTTAAAC ATAATTTTAA ATAATTTTAT ATATGATAAT GTTATCCAAG TGCTAAGGGA   5340
TGTATTGTTA CTGCTGTGCA AAAAAAAAAA AAAAAAAAAC TCCAAATAAA TATGTTGAAA   5400
CCAAGTTTAT ATGCAAGAAA ACAATATTAA AAAGGCCAAA GTACCACCAT AATAGGCTGT   5460
GTGGAGACGG CAGGCTACAA AACACTAGTA ATAATGCTGA GAAAGTTGAA AAAAGAAAGA   5520
AAGCAACAAT ATGCTTTGGT TGTTGTAGGT TTATGTACTC CAAGAATATC TCCTCTCAAA   5580
CTTTTACGTT TTTTCCAAAG AAAAGTTAAC TTTGGCTGGG CGCAGTGGCT CTTGCCTGTA   5640
GTCCCAGCCT TGGGAGGCCC AAGGCGGGCA GATCACCTGA GGTCAGGAGT TTGAGACCAG   5700
CCTGACCAAA AATGGAGAAA CCCGCCCCCC TCACTACTAA AAGAATACAA AATTAGGCCG   5760
GGCACAGTGG CTTACCCCTG TGATCCCAGC ACTTTGGGAG GCCGAAGCAG GAAGATCACC   5820
TGAGGTCAGG AGTTCGAGAC CAGCCATGGA GAAACCCGTC TCTACTAAAA ATACAAAATT   5880
AGCCGGGCGT GGTGGTGCAT GACTGTAATC CCAGCTACTC AGGAGGCTAA GGCAGAGAAT   5940
CACTTGAACC CAGGCAGTGG AGGTTGCAGT GAGCCGAGAT CGTGCCATTG CACTCCAGCC   6000
TGGGCAACAA GAGCGAAACT CTGTATCCAA AAAACAAAAG AAAAGAAAAG GTAACCTTGA   6060
ACTATGTGAG ATCTTTAGAA ATGCATTCTT TCTGTAAAAT GTGACTACAT TTGCCTTATT   6120
TATGGTAAAA ATGTTGAGGC CTCAAACAAC CCATATTTTC TCGGTCTCCC CGCTGCCTAG   6180
CCTTTGTTCA CATTGCTTCT TCTTGGTGGA AGCTCTTCCT CTGGCCTTGA AAATGCCTGC   6240
TTCTCTTTCA AGGTAGCACA GTCATCACTT TCTGTGGTAA CCTTCTCCAG CACCATCAAA   6300
CAGAAAGAAT GAATCTCTTG TAAATTCAGC TCTTACGTCA TTCATTACAT TATTTTGTAA   6360
CTCTTTATAG ATTCTTCTCT CCCACTAGAC TCTGAGTCAC TGGAGAGTAG GAGCCAACTC   6420
```

-continued

```
TCATTCATGT GTGGTTTGGT CAGCTACTGG CCACATTCCT GATGCATAGT TAATGCTCAA   6480
ACCTTAACTG GTGAATCAGC TCAAATATTG TCCTTCTCTA AATCCATTCA CTCATTGACT   6540
AACTATGTAC TCAAAATAGT AAACACCAGT AATTTAATCC AATTCCTGCC CATACTGCTT   6600
GGTACATTTC AGGTGAATTA GTTTGATAAA TATGTGTGTA TTACATAATA TTAAAGTATG   6660
TACAGAAGAT CATGCTAATC ATAATTCACA ACTGATAACT AATCAAACAT AAATGCTCTC   6720
AGGTTAACAA ATGTCTGCCT TCTCAGTTAA TGCAGTCATT AACAAACACC TTCTGATGCT   6780
GATAATAGGG CCTTGTTCAG CAATGAAGCC ATAAAGGTGA ATAAAGAACA TGCCCTCGTG   6840
GAGCTCACAG CCTAGTCATT ATTGTTCTGA TTTTTAATAT TAATGTTGGT TTGGGTTTTG   6900
GTGAAAAATG TTTAGACTTA TCTTAGTGAT CTTTTCATCC TTTGCTATAT TATTTTTCTC   6960
TAAGAGTCTT CCTTATCCCC TCCTTTAAAA AACTAGGTGA TAATTCTAAA TTGTAAATTT   7020
AAATATTATA AATAGCTTAT AAAATTTAAT ATTTATAATA TTTAAATGTT TGATAAATAT   7080
TTAAATTTTA TAATATTTAA ATGTTTATTT AAATTCATTT GTACATCAGT TTTTATTTTA   7140
TTTAAATGTG TTGGCCAGGC ATGGTGGCTG ACACCTATAA TCCCAGAACT TTGAGAGGCC   7200
AAGTCAGGCA AACCATTTGA GCTCAGGAGT TTGAGACCAC CCTGGGCAAC GTGGTGAAAC   7260
CCTGTCTCTA CCAAACATAT GAAAACTTAT CTGGGTGTGG TGGCACGCAT CTGTGGTCCC   7320
AGATGGGAGT CCCAGGCTAA GATGGGAGAA TCGCTTGAAC CCAGGTGAGA GGGGTGGGGT   7380
GGATGTTGCA GTGAGCTGAG ATCGTGCCAC TGCACTCCAA CCTGGGTGAC AGAGTGAGAC   7440
TCCATCTCAA AAAAAAAAAA TGTTATCTAA ATAAGATAAA TTTAATAACT GTTCGCACTT   7500
AGATGAGCAT AAGGAACTAA ACCTAGATAA AACTATCAAA TAAGGCCTGG GTACAGTGAC   7560
TCATGCCTGT AATCTCAAGC ACTTTGGGAG GCCAAAATTA TACAAAGTTA GTTGTATAAC   7620
ACCAACTAAC AACTATTTTG GGGTTAGCTT AATTCAGATT AATTTTTTTT AAACTGAGTT   7680
TTAAATTCCT GCTTACTCTA CCATACATGC TAGGCCTCAT ATTATGCTAG AAAAATTTTG   7740
AGCACAGATT TATGAATACT CTCCTGCATA CCATTTAATT TTTAAACAAA TTTTAATGCA   7800
GTATATATGT GCCTTTTTAC CAACACATTA AATAATAAGA TCTACTGTGA GGACTAAATT   7860
TCTGTAATTT CAAAGTAGTA ATGAGTTTAA ACCATGTCTC AAGATCTCTG CAATAACTGT   7920
AGCACAACAG AAAATAGGTA TTTCTATTAA TGACAGAGTC ACAAGTACTA CTAATAATAC   7980
TGTGGTTTGT TTCCTGCAAC TAATCATGGG AGGAATGCTA AATTTCAGAG GTTGGTGAAA   8040
ATACATGTGT ATTTTTTTCC CCATCCAAGT TCACAGATTT CTCACACTGA GAACTCCTAT   8100
TCCATAACAA AATTCTGGAA GCCTGCACAC CGTATTGGAA GAAGGGCAGA AAGGAAAAGC   8160
AAATGGAAGG ATTTAAATTT TTTTCAAATC CTGTATCCCT TGATTTTACA GCAAGATTGT   8220
ATTTATGTAT TACTTGTGTT AAAAATATAG TATAATCGAG ACTCCAGATC AAAAATCACC   8280
GCAGCTCAGG GAGAAAGAGG GCCACCAAAT GCCAGAGCCC TTCAGCCTTC TCCCACCCTG   8340
CCTGTACCCT CAGATGGAAG CACTTTTTTA TCATTGTTTC ACCTTTAGCA TTTTGACAAT   8400
GAAGTCACAA ACCTTCAGCC TCTCACCCAT AGGAACCCAC TGGTTGTAAG AGAAGGATGA   8460
AGCCAGTCCT TCCTAAAGGG CACGATTAGA TGTGTTTATG GCATCCTCAG GTGAAACTAT   8520
ATTTATATTG ACAATATATT TATATTTCTC AAGGAATACT AGAATAATGA TTCAGTTCAG   8580
TACTAGGCCA TTTATCTACC CTTTATAATA TTGTTTAATG AGAAAATGCT TTCTATCTTC   8640
CAAATATCTG ATGATTTGTA AGAGAACACT TAAACATGGG TATTCATAAG CTGAAACTTC   8700
TGGCATTTAT TGAATGTCAA GATTGTTCAT CAGTATACTA GGTGATTAAC TGACCACTGA   8760
```

-continued

ACTTGAAGGT AGTATAAAGT AGTAGTAAAA GGTACAATCA TTGTCTCTTA ACAGATGGCT 8820

CTTTGCTTTC ATTAG 8835

(2) INFORMATION FOR SEQ ID NO:11:

(i) SEQUENCE CHARACTERISTICS:
(A) LENGTH: 1371 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: intron
(B) LOCATION: 1..1371
(C) IDENTIFICATION METHOD: E (xi) SEQUENCE DESCRIPTION: SEQ ID NO: 11:

GTAAGGCTAA TGCCATAGAA CAAATACCAG GTTCAGATAA ATCTATTCAA TTAGAAAAGA 60

TGTTGTGAGG TGAACTATTA AGTGACTCTT TGTGTCACCA AATTTCACTG TAATATTAAT 120

GGCTCTTAAA AAAATAGTGG ACCTCTAGAA ATTAACCACA ACATGTCCAA GGTCTCAGCA 180

CCTTGTCACA CCACGTGTCC TGGCACTTTA ATCAGCAGTA GCTCACTCTC CAGTTGGCAG 240

TAAGTGCACA TCATGAAAAT CCCAGTTTTC ATGGGAAAAT CCCAGTTTTC ATTGGATTTC 300

CATGGGAAAA ATCCCAGTAC AAAACTGGGT GCATTCAGGA AATACAATTT CCCAAAGCAA 360

ATTGGCAAAT TATGTAAGAG ATTCTCTAAA TTTAGAGTTC CGTGAATTAC ACCATTTTAT 420

GTAAATATGT TTGACAAGTA AAAATTGATT CTTTTTTTTT TTTTCTGTTG CCCAGGCTGG 480

AGTGCAGTGG CACAATCTCT GCTCACTGCA ACCTCCACCT CCTGGGTTCA AGCAATTCTC 540

CTGCCTCAGC CTTCTGAGTA GCTGGGACTA CAGGTGCATC CCGCCATGCC TGGCTAATTT 600

TTGGGTATTT TTACTAGAGA CAGGGTTTTG GCATGTTGTC CAGGCTGGTC TTGGACTCCT 660

GATCTCAGAT GATCCTCCTG GCTCGGGCTC CCAAAGTGCT GGGATTACAG GCATGAACCA 720

CCACACATGG CCTAAAAATT GATTCTTATG ATTAATCTCC TGTGAACAAT TTGGCTTCAT 780

TTGAAAGTTT GCCTTCATTT GAAACCTTCA TTTAAAAGCC TGAGCAACAA AGTGAGACCC 840

CATCTCTACA AAAAACTGCA AAATATCCTG TGGACACCTC CTACCTTCTG TGGAGGCTGA 900

AGCAGGAGGA TCACTTGAGC CTAGGAATTT GAGCCTGCAG TGAGCTATGA TCCCACCCCT 960

ACACTCCAGC CTGCATGACA GTAGACCCTG ACACACACAC ACAAAAAAAA ACCTTCATAA 1020

AAAATTATTA GTTGACTTTT CTTAGGTGAC TTTCCGTTTA AGCAATAAAT TTAAAAGTAA 1080

AATCTCTAAT TTTAGAAAAT TTATTTTTAG TTACATATTG AAATTTTTAA ACCCTAGGTT 1140

TAAGTTTTAT GTCTAAATTA CCTGAGAACA CACTAAGTCT GATAAGCTTC ATTTTATGGG 1200

CCTTTTGGAT GATTATATAA TATTCTGATG AAAGCCAAGA CAGACCCTTA AACCATAAAA 1260

ATAGGAGTTC GAGAAAGAGG AGTAGCAAAA GTAAAAGCTA GAATGAGATT GAATTCTGAG 1320

TCGAAATACA AAATTTTACA TATTCTGTTT CTCTCTTTTT CCCCCTCTTA G 1371

(2) INFORMATION FOR SEQ ID NO: 12:

(i) SEQUENCE CHARACTERISTICS:
(A) LENGTH: 3383 base pairs
(B) TYPE: nucleic acid -continued (C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: intron
(B) LOCATION: 1..3383
(C) IDENTIFICATION METHOD: E (xi) SEQUENCE DESCRIPTION: SEQ ID NO: 12:

```
GTAAAGTAGA AATGAATTTA TTTTTCTTTG CAAACTAAGT ATCTGCTTGA GACACATCTA     60
TCTCACCATT GTCAGCTGAG GAAAAAAAAA AATGGTTCTC ATGCTACCAA TCTGCCTTCA    120
AAGAAATGTG GACTCAGTAG CACAGCTTTG GAATGAAGAT GATCATAAGA GATACAAAGA    180
AGAACCTCTA GCAAAAGATG CTTCTCTATG CCTTAAAAAA TTCTCCAGCT CTTAGAATCT    240
ACAAAATAGA CTTTGCCTGT TTCATTGGTC CTAAGATTAG CATGAAGCCA TGGATTCTGT    300
TGTAGGGGGA GCGTTGCATA GGAAAAAGGG ATTGAAGCAT TAGAATTGTC CAAAATCAGT    360
AACACCTCCT CTCAGAAATG CTTTGGGAAG AAGCCTGGAA GGTTCCGGGT TGGTGGTGGG    420
GTGGGGCAGA AAATTCTGGA AGTAGAGGAG ATAGGAATGG GTGGGGCAAG AAGACCACAT    480
TCAGAGGCCA AAAGCTGAAA GAAACCATGG CATTTATGAT GAATTCAGGG TAATTCAGAA    540
TGGAAGTAGA GTAGGAGTAG GAGACTGGTG AGAGGAGCTA GAGTGATAAA CAGGGTGTAG    600
AGCAAGACGT TCTCTCACCC CAAGATGTGA AATTTGGACT TTATCTTGGA GATAATAGGG    660
TTAATTAAGC ACAATATGTA TTAGCTAGGG TAAAGATTAG TTTGTTGTAA CAAAGACATC    720
CAAAGATACA GTAGCTGAAT AAGATAGAGA ATTTTTCTCT CAAAGAAAGT CTAAGTAGGC    780
AGCTCAGAAG TAGTATGGCT GGAAGCAACC TGATGATATT GGGACCCCCA ACCTTCTTCA    840
GTCTTGTACC CATCATCCCC TAGTTGTTGA TCTCACTCAC ATAGTTGAAA ATCATCATAC    900
TTCCTGGGTT CATATCCCAG TTATCAAGAA AGGGTCAAGA GAAGTCAGGC TCATTCCTTT    960
CAAAGACTCT AATTGGAAGT TAAACACATC AATCCCCCTC ATATTCCATT GACTAGAATT   1020
TAATCACATG GCCACACCAA GTGCAAGGAA ATCTGGAAAA TATAATCTTT ATTCCAGGTA   1080
GCCATATGAC TCTTTAAAAT TCAGAAATAA TATATTTTTA AAATATCATT CTGGCTTTGG   1140
TATAAAGAAT TGATGGTGTG GGGTGAGGAG GCCAAAATTA AGGGTTGAGA GCCTATTATT   1200
TTAGTTATTA CAAGAAATGA TGGTGTCATG AATTAAGGTA GACATAGGGG AGTGCTGATG   1260
AGGAGCTGTG AATGGATTTT AGAAACACTT GAGAGAATCA ATAGGACATG ATTTAGGGTT   1320
GGATTTGGAA AGGAGAAGAA AGTAGAAAAG ATGATGCCTA CATTTTTCAC TTAGGCAATT   1380
TGTACCATTC AGTGAAATAG GGAACACAGG AGGAAGAGCA GGTTTTGGTG TATACAAAGA   1440
GGAGGATGGA TGACGCATTT CGTTTTGGAT CTGAGATGTC TGTGGAACGT CCTAGTGGAG   1500
ATGTCCACAA ACTCTTCTAC ATGTGGTTCT GAGTTCAGGA CACAGATTTG GGCTGGAGAT   1560
AGAGATATTG TAGGCTTATA CATAGAAATG GCATTTGAAT CTATAGAGAT AAAAAGACAC   1620
ATCAGAGGAA ATGTGTAAAG TGAGAGAGGA AAAGCCAAGT ACTGTGCTGG GGGGAATACC   1680
TACATTTAAA GGATGCAGTA GAAAGAAGCT AATAAACAAC AGAGAGCAGA CTAACCAAAA   1740
GGGGAGAAGA AAAACCAAGA GAATTCCACC GACTCCCAGG AGAGCATTTC AAGATTGAGG   1800
GGATAGGTGT TGTGTTGAAT TTTGCAGCCT TGAGAATCAA GGGCCAGAAC ACAGCTTTTA   1860
```

-continued

```
GATTTAGCAA CAAGGAGTTT GGTGATCTCA GTGAAAGCAG CTTGATGGTG AAATGGAGGC   1920

AGAGGCAGAT TGCAATGAGT GAAACAGTGA ATGGGAAGTG AAGAAATGAT ACAGATAATT   1980

CTTGCTAAAA GCTTGGCTGT TAAAAGGAGG AGAGAAACAA GACTAGCTGC AAAGTGAGAT   2040

TGGGTTGATG GAGCAGTTTT AAATCTCAAA ATAAAGAGCT TTGTGCTTTT TTGATTATGA   2100

AAATAATGTG TTAATTGTAA CTAATTGAGG CAATGAAAAA AGATAATAAT ATGAAAGATA   2160

AAAATATAAA AACCACCCAG AAATAATGAT AGCTACCATT TTGATACAAT ATTTCTACAC   2220

TCCTTTCTAT GTATATATAC AGACACAGAA ATGCTTATAT TTTTATTAAA AGGGATTGTA   2280

CTATACCTAA GCTGCTTTTT CTAGTTAGTG ATATATATGG ACATCTCTCC ATGGCAACGA   2340

GTAATTGCAG TTATATTAAG TTCATGATAT TTCACAATAA GGGCATATCT TTGCCCTTTT   2400

TATTTAATCA ATTCTTAATT GGTGAATGTT TGTTTCCAGT TTGTTGTTGT TATTAACAAT   2460

GTTCCCATAA GCATTCCTGT ACACCAATGT TCACACATTT GTCTGATTTT TTCTTCAGGA   2520

TAAAACCCAG GAGGTAGAAT TGCTGGGTTG ATAGAAGAGA AAGGATGATT GCCAAATTAA   2580

AGCTTCAGTA GAGGGTACAT GCCGAGCACA AATGGGATCA GCCCTAGATA CCAGAAATGG   2640

CACTTTCTCA TTTCCCCTTG GGACAAAAGG GAGAGAGGCA ATAACTGTGC TGCCAGAGTT   2700

AAATTTGTAC GTGGAGTAGC AGGAAATCAT TTGCTGAAAA TGAAAACAGA GATGATGTTG   2760

TAGAGGTCCT GAAGAGAGCA AAGAAAATTT GAAATTGCGG CTATCAGCTA TGGAAGAGAG   2820

TGCTGAACTG GAAAACAAAA GAAGTATTGA CAATTGGTAT GCTTGTAATG GCACCGATTT   2880

GAACGCTTGT GCCATTGTTC ACCAGCAGCA CTCAGCAGCC AAGTTTGGAG TTTTGTAGCA   2940

GAAAGACAAA TAAGTTAGGG ATTTAATATC CTGGCCAAAT GGTAGACAAA ATGAACTCTG   3000

AGATCCAGCT GCACAGGGAA GGAAGGGAAG ACGGGAAGAG GTTAGATAGG AAATACAAGA   3060

GTCAGGAGAC TGGAAGATGT TGTGATATTT AAGAACACAT AGAGTTGGAG TAAAAGTGTA   3120

AGAAAACTAG AAGGGTAAGA GACCGGTCAG AAAGTAGGCT ATTTGAAGTT AACACTTCAG   3180

AGGCAGAGTA GTTCTGAATG GTAACAAGAA ATTGAGTGTG CCTTTGAGAG TAGGTTAAAA   3240

AACAATAGGC AACTTTATTG TAGCTACTTC TGGAACAGAA GATTGTCATT AATAGTTTTA   3300

GAAAACTAAA ATATATAGCA TACTTATTTG TCAATTAACA AAGAAACTAT GTATTTTTAA   3360

ATGAGATTTA ATGTTTATTG TAG                                           3383
```

(2) INFORMATION FOR SEQ ID NO: 13:

(i) SEQUENCE CHARACTERISTICS:
(A) LENGTH: 11464 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: 5'UTR
(B) LOCATION: 1..3
(C) IDENTIFICATION METHOD: E
(A) NAME/KEY: leader peptide
(B) LOCATION: 4..82
(C) IDENTIFICATION METHOD: S
(A) NAME/KEY: intron
(B) LOCATION: 83..1453
(C) IDENTIFICATION METHOD: E
(A) NAME/KEY: leader peptide
(B) LOCATION: 1454..1465

(C) IDENTIFICATION METHOD: S
(A) NAME/KEY: intron
(B) LOCATION: 1466..4848
(C) IDENTIFICATION METHOD: E
(A) NAME/KEY: leader peptide
(B) LOCATION: 4849..4865
(C) IDENTIFICATION METHOD: S
(A) NAME/KEY: mat peptide
(B) LOCATION: 4866..4983
(C) IDENTIFICATION METHOD: S
(A) NAME/KEY: intron
(B) LOCATION: 4984..6317
(C) IDENTIFICATION METHOD: E
(A) NAME/KEY: mat peptide
(B) LOCATION: 6318..6451
(C) IDENTIFICATION METHOD: S
(A) NAME/KEY: intron
(B) LOCATION: 6452..11224
(C) IDENTIFICATION METHOD: E
(A) NAME/KEY: mat peptide
(B) LOCATION: 11225..11443
(C) IDENTIFICATION METHOD: S
(A) NAME/KEY: 3'UTR
(B) LOCATION: 11444..11464
(C) IDENTIFICATION METHOD: E (xi) SEQUENCE DESCRIPTION: SEQ ID NO: 13:

```
AAG ATG GCT GCT GAA CCA GTA GAA GAC AAT TGC ATC AAC TTT GTG GCA       48
    Met Ala Ala Glu Pro Val Glu Asp Asn Cys Ile Asn Phe Val Ala
        -35                 -30                 -25

ATG AAA TTT ATT GAC AAT ACG CTT TAC TTT ATA G   GTAAGG CTAATGCCAT     98
Met Lys Phe Ile Asp Asn Thr Leu Tyr Phe Ile Ala
    -20                 -15                 -10

AGAACAAATA CCAGGTTCAG ATAAATCTAT TCAATTAGAA AAGATGTTGT GAGGTGAACT    158

ATTAAGTGAC TCTTTGTGTC ACCAAATTTC ACTGTAATAT TAATGGCTCT TAAAAAAATA    218

GTGGACCTCT AGAAATTAAC CACAACATGT CCAAGGTCTC AGCACCTTGT CACACCACGT    278

GTCCTGGCAC TTTAATCAGC AGTAGCTCAC TCTCCAGTTG GCAGTAAGTG CACATCATGA    338

AAATCCCAGT TTTCATGGGA AAATCCCAGT TTTCATTGGA TTTCCATGGG AAAAATCCCA    398

GTACAAAACT GGGTGCATTC AGGAAATACA ATTTCCCAAA GCAAATTGGC AAATTATGTA    458

AGAGATTCTC TAAATTTAGA GTTCCGTGAA TTACACCATT TTATGTAAAT ATGTTTGACA    518

AGTAAAAATT GATTCTTTTT TTTTTTTTCT GTTGCCCAGG CTGGAGTGCA GTGGCACAAT    578

CTCTGCTCAC TGCAACCTCC ACCTCCTGGG TTCAAGCAAT TCTCCTGCCT CAGCCTTCTG    638

AGTAGCTGGG ACTACAGGTG CATCCCGCCA TGCCTGGCTA ATTTTTGGGT ATTTTTACTA    698

GAGACAGGGT TTTGGCATGT TGTCCAGGCT GGTCTTGGAC TCCTGATCTC AGATGATCCT    758

CCTGGCTCGG GCTCCCAAAG TGCTGGGATT ACAGGCATGA ACCACCACAC ATGGCCTAAA    818

AATTGATTCT TATGATTAAT CTCCTGTGAA CAATTTGGCT TCATTTGAAA GTTTGCCTTC    878

ATTTGAAACC TTCATTTAAA AGCCTGAGCA ACAAAGTGAG ACCCCATCTC TACAAAAAAC    938

TGCAAAATAT CCTGTGGACA CCTCCTACCT TCTGTGGAGG CTGAAGCAGG AGGATCACTT    998

GAGCCTAGGA ATTTGAGCCT GCAGTGAGCT ATGATCCCAC CCCTACACTC CAGCCTGCAT   1058

GACAGTAGAC CCTGACACAC ACACACAAAA AAAAACCTTC ATAAAAAATT ATTAGTTGAC   1118

TTTTCTTAGG TGACTTTCCG TTTAAGCAAT AAATTTAAAA GTAAAATCTC TAATTTTAGA   1178

AAATTTATTT TTAGTTACAT ATTGAAATTT TTAAACCCTA GGTTTAAGTT TTATGTCTAA   1238

ATTACCTGAG AACACACTAA GTCTGATAAG CTTCATTTTA TGGGCCTTTT GGATGATTAT   1298

ATAATATTCT GATGAAAGCC AAGACAGACC CTTAAACCAT AAAAATAGGA GTTCGAGAAA   1358
```

-continued

```
GAGGAGTAGC AAAAGTAAAA GCTAGAATGA GATTGAATTC TGAGTCGAAA TACAAAATTT   1418

TACATATTCT GTTTCTCTCT TTTTCCCCCT CTTAG   CT GAA GAT GAT G   GTAAA   1470
                                        Ala Glu Asp Asp Glu
                                        -10

GTAGAAATGA ATTTATTTTT CTTTGCAAAC TAAGTATCTG CTTGAGACAC ATCTATCTCA   1530

CCATTGTCAG CTGAGGAAAA AAAAAAATGG TTCTCATGCT ACCAATCTGC CTTCAAAGAA   1590

ATGTGGACTC AGTAGCACAG CTTTGGAATG AAGATGATCA TAAGAGATAC AAAGAAGAAC   1650

CTCTAGCAAA AGATGCTTCT CTATGCCTTA AAAAATTCTC CAGCTCTTAG AATCTACAAA   1710

ATAGACTTTG CCTGTTTCAT TGGTCCTAAG ATTAGCATGA AGCCATGGAT TCTGTTGTAG   1770

GGGGAGCGTT GCATAGGAAA AAGGGATTGA AGCATTAGAA TTGTCCAAAA TCAGTAACAC   1830

CTCCTCTCAG AAATGCTTTG GGAAGAAGCC TGGAAGGTTC CGGGTTGGTG GTGGGGTGGG   1890

GCAGAAAATT CTGGAAGTAG AGGAGATAGG AATGGGTGGG GCAAGAAGAC CACATTCAGA   1950

GGCCAAAAGC TGAAAGAAAC CATGGCATTT ATGATGAATT CAGGGTAATT CAGAATGGAA   2010

GTAGAGTAGG AGTAGGAGAC TGGTGAGAGG AGCTAGAGTG ATAAACAGGG TGTAGAGCAA   2070

GACGTTCTCT CACCCCAAGA TGTGAAATTT GGACTTTATC TTGGAGATAA TAGGGTTAAT   2130

TAAGCACAAT ATGTATTAGC TAGGGTAAAG ATTAGTTTGT TGTAACAAAG ACATCCAAAG   2190

ATACAGTAGC TGAATAAGAT AGAGAATTTT TCTCTCAAAG AAAGTCTAAG TAGGCAGCTC   2250

AGAAGTAGTA TGGCTGGAAG CAACCTGATG ATATTGGGAC CCCCAACCTT CTTCAGTCTT   2310

GTACCCATCA TCCCCTAGTT GTTGATCTCA CTCACATAGT TGAAAATCAT CATACTTCCT   2370

GGGTTCATAT CCCAGTTATC AAGAAAGGGT CAAGAGAAGT CAGGCTCATT CCTTTCAAAG   2430

ACTCTAATTG GAAGTTAAAC ACATCAATCC CCCTCATATT CCATTGACTA GAATTTAATC   2490

ACATGGCCAC ACCAAGTGCA AGGAAATCTG GAAAATATAA TCTTTATTCC AGGTAGCCAT   2550

ATGACTCTTT AAAATTCAGA AATAATATAT TTTTAAAATA TCATTCTGGC TTTGGTATAA   2610

AGAATTGATG GTGTGGGGTG AGGAGGCCAA AATTAAGGGT TGAGAGCCTA TTATTTTAGT   2670

TATTACAAGA AATGATGGTG TCATGAATTA AGGTAGACAT AGGGGAGTGC TGATGAGGAG   2730

CTGTGAATGG ATTTTAGAAA CACTTGAGAG AATCAATAGG ACATGATTTA GGGTTGGATT   2790

TGGAAAGGAG AAGAAAGTAG AAAAGATGAT GCCTACATTT TTCACTTAGG CAATTTGTAC   2850

CATTCAGTGA AATAGGGAAC ACAGGAGGAA GAGCAGGTTT TGGTGTATAC AAAGAGGAGG   2910

ATGGATGACG CATTTCGTTT TGGATCTGAG ATGTCTGTGG AACGTCCTAG TGGAGATGTC   2970

CACAAACTCT TCTACATGTG GTTCTGAGTT CAGGACACAG ATTTGGGCTG GAGATAGAGA   3030

TATTGTAGGC TTATACATAG AAATGGCATT TGAATCTATA GAGATAAAAA GACACATCAG   3090

AGGAAATGTG TAAAGTGAGA GAGGAAAAGC CAAGTACTGT GCTGGGGGGA ATACCTACAT   3150

TTAAAGGATG CAGTAGAAAG AAGCTAATAA ACAACAGAGA GCAGACTAAC CAAAAGGGGA   3210

GAAGAAAAAC CAAGAGAATT CCACCGACTC CCAGGAGAGC ATTTCAAGAT TGAGGGGATA   3270

GGTGTTGTGT TGAATTTTGC AGCCTTGAGA ATCAAGGGCC AGAACACAGC TTTTAGATTT   3330

AGCAACAAGG AGTTTGGTGA TCTCAGTGAA AGCAGCTTGA TGGTGAAATG GAGGCAGAGG   3390

CAGATTGCAA TGAGTGAAAC AGTGAATGGG AAGTGAAGAA ATGATACAGA TAATTCTTGC   3450

TAAAAGCTTG GCTGTTAAAA GGAGGAGAGA AACAAGACTA GCTGCAAAGT GAGATTGGGT   3510

TGATGGAGCA GTTTTAAATC TCAAAATAAA GAGCTTTGTG CTTTTTTGAT TATGAAAATA   3570

ATGTGTTAAT TGTAACTAAT TGAGGCAATG AAAAAAGATA ATAATATGAA AGATAAAAAT   3630
```

-continued

```
ATAAAAACCA CCCAGAAATA ATGATAGCTA CCATTTTGAT ACAATATTTC TACACTCCTT   3690

TCTATGTATA TATACAGACA CAGAAATGCT TATATTTTTA TTAAAAGGGA TTGTACTATA   3750

CCTAAGCTGC TTTTTCTAGT TAGTGATATA TATGGACATC TCTCCATGGC AACGAGTAAT   3810

TGCAGTTATA TTAAGTTCAT GATATTTCAC AATAAGGGCA TATCTTTGCC CTTTTTATTT   3870

AATCAATTCT TAATTGGTGA ATGTTTGTTT CCAGTTTGTT GTTGTTATTA ACAATGTTCC   3930

CATAAGCATT CCTGTACACC AATGTTCACA CATTTGTCTG ATTTTTTCTT CAGGATAAAA   3990

CCCAGGAGGT AGAATTGCTG GGTTGATAGA AGAGAAAGGA TGATTGCCAA ATTAAAGCTT   4050

CAGTAGAGGG TACATGCCGA GCACAAATGG GATCAGCCCT AGATACCAGA AATGGCACTT   4110

TCTCATTTCC CCTTGGGACA AAAGGGAGAG AGGCAATAAC TGTGCTGCCA GAGTTAAATT   4170

TGTACGTGGA GTAGCAGGAA ATCATTTGCT GAAAATGAAA ACAGAGATGA TGTTGTAGAG   4230

GTCCTGAAGA GAGCAAAGAA AATTTGAAAT TGCGGCTATC AGCTATGGAA GAGAGTGCTG   4290

AACTGGAAAA CAAAAGAAGT ATTGACAATT GGTATGCTTG TAATGGCACC GATTTGAACG   4350

CTTGTGCCAT TGTTCACCAG CAGCACTCAG CAGCCAAGTT TGGAGTTTTG TAGCAGAAAG   4410

ACAAATAAGT TAGGGATTTA ATATCCTGGC CAAATGGTAG ACAAAATGAA CTCTGAGATC   4470

CAGCTGCACA GGGAAGGAAG GGAAGACGGG AAGAGGTTAG ATAGGAAATA CAAGAGTCAG   4530

GAGACTGGAA GATGTTGTGA TATTTAAGAA CACATAGAGT TGGAGTAAAA GTGTAAGAAA   4590

ACTAGAAGGG TAAGAGACCG GTCAGAAAGT AGGCTATTTG AAGTTAACAC TTCAGAGGCA   4650

GAGTAGTTCT GAATGGTAAC AAGAAATTGA GTGTGCCTTT GAGAGTAGGT TAAAAAACAA   4710

TAGGCAACTT TATTGTAGCT ACTTCTGGAA CAGAAGATTG TCATTAATAG TTTTAGAAAA   4770

CTAAAATATA TAGCATACTT ATTTGTCAAT TAACAAAGAA ACTATGTATT TTTAAATGAG   4830

ATTTAATGTT TATTGTAG  AA AAC CTG GAA TCA GAT TAC TTT GGC AAG CTT     4880
                    Glu Asn Leu Glu Ser Asp Tyr Phe Gly Lys Leu
                         -5                  1               5

GAA TCT AAA TTA TCA GTC ATA AGA AAT TTG AAT GAC CAA GTT CTC TTC     4928
Glu Ser Lys Leu Ser Val Ile Arg Asn Leu Asn Asp Gln Val Leu Phe
                10                  15                  20

ATT GAC CAA GGA AAT CGG CCT CTA TTT GAA GAT ATG ACT GAT TCT GAC     4976
Ile Asp Gln Gly Asn Arg Pro Leu Phe Glu Asp Met Thr Asp Ser Asp
            25                  30                  35

TGT AGA G   GTATTTTTT TTAATTCGCA AACATAGAAA TGACTAGCTA CTTCTTCCCA   5032
Cys Arg Asp
        40

TTCTGTTTTA CTGCTTACAT TGTTCCGTGC TAGTCCCAAT CCTCAGATGA AAAGTCACAG   5092

GAGTGACAAT AATTTCACTT ACAGGAAACT TTATAAGGCA TCCACGTTTT TTAGTTGGGG   5152

TAAAAAATTG GATACAATAA GACATTGCTA GGGGTCATGC CTCTCTGAGC CTGCCTTTGA   5212

ATCACCAATC CCTTTATTGT GATTGCATTA ACTGTTTAAA ACCTCTATAG TTGGATGCTT   5272

AATCCCTGCT TGTTACAGCT GAAAATGCTG ATAGTTTACC AGGTGTGGTG GCATCTATCT   5332

GTAATCCTAG CTACTTGGGA GGCTCAAGCA GGAGGATTGC TTGAGGCCAG GACTTTGAGG   5392

CTGTAGTACA CTGTGATCGT ACCTGTGAAT AGCCACTGCA CTCCAGCCTG GGTGATATAC   5452

AGACCTTGTC TCTAAAATTA AAAAAAAAAA AAAAAAAAAC CTTAGGAAAG GAAATTGATC   5512

AAGTCTACTG TGCCTTCCAA AACATGAATT CCAAATATCA AAGTTAGGCT GAGTTGAAGC   5572

AGTGAATGTG CATTCTTTAA AAATACTGAA TACTTACCTT AACATATATT TTAAATATTT   5632

TATTTAGCAT TTAAAAGTTA AAAACAATCT TTTAGAATTC ATATCTTTAA AATACTCAAA   5692
```

-continued

```
AAAGTTGCAG CGTGTGTGTT GTAATACACA TTAAACTGTG GGGTTGTTTG TTTGTTTGAG   5752

ATGCAGTTTC ACTCTGTCAC CCAGGCTGAA GTGCAGTGCA GTGCAGTGGT GTGATCTCGG   5812

CTCACTACAA CCTCCACCTC CCACGTTCAA GCGATTCTCA TGCCTCAGTC TCCCGAGTAG   5872

GTGGGATTAC AGGCATGCAC CACTTACACC CGGCTAATTT TTGTATTTTT AGTAGAGCTG   5932

GGGTTTCACC ATGTTGGCCA GGCTGGTCTC AAACCCCTAA CCTCAAGTGA TCTGCCTGCC   5992

TCAGCCTCCC AAACAAACAA ACAACCCCAC AGTTTAATAT GTGTTACAAC ACACATGCTG   6052

CAACTTTTAT GAGTATTTTA ATGATATAGA TTATAAAAGG TTGTTTTTAA CTTTTAAATG   6112

CTGGGATTAC AGGCATGAGC CACTGTGCCA GGCCTGAACT GTGTTTTTAA AAATGTCTGA   6172

CCAGCTGTAC ATAGTCTCCT GCAGACTGGC CAAGTCTCAA AGTGGGAACA GGTGTATTAA   6232

GGACTATCCT TGGTTAAAT TTCCGCAAAT GTTCCTGTGC AAGAATTCTT CTAACTAGAG   6292

TTCTCATTTA TTATATTTAT TTCAG  AT AAT GCA CCC CGG ACC ATA TTT ATT     6343
                             Asp Asn Ala Pro Arg Thr Ile Phe Ile
                             40                  45

ATA AGT ATG TAT AAA GAT AGC CAG CCT AGA GGT ATG GCT GTA ACT ATC     6391
Ile Ser Met Tyr Lys Asp Ser Gln Pro Arg Gly Met Ala Val Thr Ile
    50                  55                  60

TCT GTG AAG TGT GAG AAA ATT TCA ACT CTC TCC TGT GAG AAC AAA ATT     6439
Ser Val Lys Cys Glu Lys Ile Ser Thr Leu Ser Cys Glu Asn Lys Ile
65                  70                  75                  80

ATT TCC TTT AAG GTAAG ACTGAGCCTT ACTTTGTTTT CAATCATGTT AATATAATCA   6496
Ile Ser Phe Lys

ATATAATTAG AAATATAACA TTATTTCTAA TGTTAATATA AGTAATGTAA TTAGAAAACT   6556

CAAATATCCT CAGACCAACC TTTTGTCTAG AACAGAAATA ACAAGAAGCA GAGAACCATT   6616

AAAGTGAATA CTTACTAAAA ATTATCAAAC TCTTTACCTA TTGTGATAAT GATGGTTTTT   6676

CTGAGCCTGT CACAGGGGAA GAGGAGATAC AACACTTGTT TTATGACCTG CATCTCCTGA   6736

ACAATCAGTC TTTATACAAA TAATAATGTA GAATACATAT GTGAGTTATA CATTTAAGAA   6796

TAACATGTGA CTTTCCAGAA TGAGTTCTGC TATGAAGAAT GAAGCTAATT ATCCTTCTAT   6856

ATTTCTACAC CTTTGTAAAT TATGATAATA TTTTAATCCC TAGTTGTTTT GTTGCTGATC   6916

CTTAGCCTAA GTCTTAGACA CAAGCTTCAG CTTCCAGTTG ATGTATGTTA TTTTTAATGT   6976

TAATCTAATT GAATAAAAGT TATGAGATCA GCTGTAAAAG TAATGCTATA ATTATCTTCA   7036

AGCCAGGTAT AAAGTATTTC TGGCCTCTAC TTTTTCTCTA TTATTCTCCA TTATTATTCT   7096

CTATTATTTT TCTCTATTTC CTCCATTATT GTTAGATAAA CCACAATTAA CTATAGCTAC   7156

AGACTGAGCC AGTAAGAGTA GCCAGGGATG CTTACAAATT GGCAATGCTT CAGAGGAGAA   7216

TTCCATGTCA TGAAGACTCT TTTTGAGTGG AGATTTGCCA ATAAATATCC GCTTTCATGC   7276

CCACCCAGTC CCCACTGAAA GACAGTTAGG ATATGACCTT AGTGAAGGTA CCAAGGGGCA   7336

ACTTGGTAGG GAGAAAAAAG CCACTCTAAA ATATAATCCA AGTAAGAACA GTGCATATGC   7396

AACAGATACA GCCCCCAGAC AAATCCCTCA GCTATCTCCC TCCAACCAGA GTGCCACCCC   7456

TTCAGGTGAC AATTTGGAGT CCCCATTCTA GACCTGACAG GCAGCTTAGT TATCAAAATA   7516

GCATAAGAGG CCTGGGATGG AAGGGTAGGG TGGAAAGGGT TAAGCATGCT GTTACTGAAC   7576

AACATAATTA GAAGGGAAGG AGATGGCCAA GCTCAAGCTA TGTGGGATAG AGGAAAACTC   7636

AGCTGCAGAG GCAGATTCAG AAACTGGGAT AAGTCCGAAC CTACAGGTGG ATTCTTGTTG   7696

AGGGAGACTG GTGAAAATGT TAAGAAGATG GAAATAATGC TTGGCACTTA GTAGGAACTG   7756

GGCAAATCCA TATTTGGGGG AGCCTGAAGT TTATTCAATT TTGATGGCCC TTTTAAATAA   7816
```

-continued

```
AAAGAATGTG GCTGGGCGTG GTGGCTCACA CCTGTAATCC CAGCACTTTG GGAGGCCGAG   7876
GGGGGCGGAT CACCTGAAGT CAGGAGTTCA AGACCAGCCT GACCAACATG GAGAAACCCC   7936
ATCTCTACTA AAAATACAAA ATTAGCTGGG CGTGGTGGCA TATGCCTGTA ATCCCAGCTA   7996
CTCGGGAGGC TGAGGCAGGA GAATCTTTTG AACCCGGGAG GCAGAGGTTG CGATGAGCCT   8056
AGATCGTGCC ATTGCACTCC AGCCTGGGCA ACAAGAGCAA AACTCGGTCT CAAAAAAAAA   8116
AAAAAAAAAG TGAAATTAAC CAAAGGCATT AGCTTAATAA TTTAATACTG TTTTTAAGTA   8176
GGGCGGGGGG TGGCTGGAAG AGATCTGTGT AAATGAGGGA ATCTGACATT TAAGCTTCAT   8236
CAGCATCATA GCAAATCTGC TTCTGGAAGG AACTCAATAA ATATTAGTTG GAGGGGGGGA   8296
GAGAGTGAGG GGTGGACTAG GACCAGTTTT AGCCCTTGTC TTTAATCCCT TTTCCTGCCA   8356
CTAATAAGGA TCTTAGCAGT GGTTATAAAA GTGGCCTAGG TTCTAGATAA TAAGATACAA   8416
CAGGCCAGGC ACAGTGGCTC ATGCCTATAA TCCCAGCACT TTGGGAGGGC AAGGCGAGTG   8476
TCTCACTTGA GATCAGGAGT TCAAGACCAG CCTGGCCAGC ATGGCGATAC TCTGTCTCTA   8536
CTAAAAAAAA TACAAAAATT AGCCAGGCAT GGTGGCATGC ACCTGTAATC CCAGCTACTC   8596
GTGAGCCTGA GGCAGAAGAA TCGCTTGAAA CCAGGAGGTG TAGGCTGCAG TGAGCTGAGA   8656
TCGCACCACT GCACTCCAGC CTGGGCGACA GAATGAGACT TTGTCTCAAA AAAAGAAAAA   8716
GATACAACAG GCTACCCTTA TGTGCTCACC TTTCACTGTT GATTACTAGC TATAAAGTCC   8776
TATAAAGTTC TTTGGTCAAG AACCTTGACA ACACTAAGAG GGATTTGCTT TGAGAGGTTA   8836
CTGTCAGAGT CTGTTTCATA TATATACATA TACATGTATA TATGTATCTA TATCCAGGCT   8896
TGGCCAGGGT TCCCTCAGAC TTTCCAGTGC ACTTGGGAGA TGTTAGGTCA ATATCAACTT   8956
TCCCTGGATT CAGATTCAAC CCCTTCTGAT GTAAAAAAAA AAAAAAAAAA GAAAGAAATC   9016
CCTTTCCCCT TGGAGCACTC AAGTTTCACC AGGTGGGGCT TTCCAAGTTG GGGGTTCTCC   9076
AAGGTCATTG GGATTGCTTT CACATCCATT TGCTATGTAC CTTCCCTATG ATGGCTGGGA   9136
GTGGTCAACA TCAAAACTAG GAAAGCTACT GCCCAAGGAT GTCCTTACCT CTATTCTGAA   9196
ATGTGCAATA AGTGTGATTA AAGAGATTGC CTGTTCTACC TATCCACACT CTCGCTTTCA   9256
ACTGTAACTT TCTTTTTTTC TTTTTTTCTT TTTTTCTTTT TTTTTGAAAC GGAGTCTCGC   9316
TCTGTCGCCC AGGCTAGAGT GCAGTGGCAC GATCTCAGCT CACTGCAAGC TCTGCCTCCC   9376
GGGTTCACGC CATTCTCCTG CCTCACCCTC CCAAGCAGCT GGGACTACAG GCGCCTGCCA   9436
CCATGCCCAG CTAATTTTTT GTATTTTTAG TAGAGACGGG GTTTCACCGT GTTAGCCAGG   9496
ATGGTCTCGA TCTCCTGAAC TTGTGATCCG CCCGCCTCAG CCTCCCAAAG TGCTGGGATT   9556
ACAGGCGTGA GCCATCGCAC CCGGCTCAAC TGTAACTTTC TATACTGGTT CATCTTCCCC   9616
TGTAATGTTA CTAGAGCTTT TGAAGTTTTG GCTATGGATT ATTTCTCATT TATACATTAG   9676
ATTTCAGATT AGTTCCAAAT TGATGCCCAC AGCTTAGGGT CTCTTCCTAA ATTGTATATT   9736
GTAGACAGCT GCAGAAGTGG GTGCCAATAG GGGAACTAGT TTATACTTTC ATCAACTTAG   9796
GACCCACACT TGTTGATAAA GAACAAAGGT CAAGAGTTAT GACTACTGAT TCCACAACTG   9856
ATTGAGAAGT TGGAGATAAC CCCGTGACCT CTGCCATCCA GAGTCTTTCA GGCATCTTTG   9916
AAGGATGAAG AAATGCTATT TTAATTTTGG AGGTTTCTCT ATCAGTGCTT AGGATCATGG   9976
GAATCTGTGC TGCCATGAGG CCAAAATTAA GTCCAAAACA TCTACTGGTT CCAGGATTAA  10036
CATGGAAGAA CCTTAGGTGG TGCCCACATG TTCTGATCCA TCCTGCAAAA TAGACATGCT  10096
GCACTAACAG GAAAAGTGCA GGCAGCACTA CCAGTTGGAT AACCTGCAAG ATTATAGTTT  10156
```

-continued

```
CAAGTAATCT AACCATTTCT CACAAGGCCC TATTCTGTGA CTGAAACATA CAAGAATCTG  10216

CATTTGGCCT TCTAAGGCAG GGCCCAGCCA AGGAGACCAT ATTCAGGACA GAAATTCAAG  10276

ACTACTATGG AACTGGAGTG CTTGGCAGGG AAGACAGAGT CAAGGACTGC CAACTGAGCC  10336

AATACAGCAG GCTTACACAG GAACCCAGGG CCTAGCCCTA CAACAATTAT TGGGTCTATT  10396

CACTGTAAGT TTTAATTTCA GGCTCCACTG AAAGAGTAAG CTAAGATTCC TGGCACTTTC  10456

TGTCTCTCTC ACAGTTGGCT CAGAAATGAG AACTGGTCAG GCCAGGCATG GTGGCTTACA  10516

CCTGGAATCC CAGCACTTTG GGAGGCCGAA GTGGGAGGGT CACTTGAGGC CAGGAGTTCA  10576

GGACCAGCTT AGGCAACAAA GTGAGATACC CCCTGACCCC TTCTCTACAA AAATAAATTT  10636

TAAAAATTAG CCAAATGTGG TGGTGTATAC TTACAGTCCC AGCTACTCAG GAGGCTGAGG  10696

CAGGGGGATT GCTTGAGCCC AGGAATTCAA GGCTGCAGTG AGCTATGATT TCACCACTGC  10756

ACTTCTGGCT GGGCAACAGA GCGAGACCCT GTCTCAAAGC AAAAAGAAAA AGAAACTAGA  10816

ACTAGCCTAA GTTTGTGGGA GGAGGTCATC ATCGTCTTTA GCCGTGAATG GTTATTATAG  10876

AGGACAGAAA TTGACATTAG CCCAAAAAGC TTGTGGTCTT TGCTGGAACT CTACTTAATC  10936

TTGAGCAAAT GTGGACACCA CTCAATGGGA GAGGAGAGAA GTAAGCTGTT TGATGTATAG  10996

GGGAAAACTA GAGGCCTGGA ACTGAATATG CATCCCATGA CAGGGAGAAT AGGAGATTCG  11056

GAGTTAAGAA GGAGAGGAGG TCAGTACTGC TGTTCAGAGA TTTTTTTTAT GTAACTCTTG  11116

AGAAGCAAAA CTACTTTTGT TCTGTTTGGT AATATACTTC AAAACAAACT TCATATATTC  11176

AAATTGTTCA TGTCCTGAAA TAATTAGGTA ATGTTTTTTT CTCTATAG GAA ATG AAT  11233
                                                     Glu Met Asn
                                                     85

CCT CCT GAT AAC ATC AAG GAT ACA AAA AGT GAC ATC ATA TTC TTT CAG    11281
Pro Pro Asp Asn Ile Lys Asp Thr Lys Ser Asp Ile Ile Phe Phe Glu
        90                  95                  100

AGA AGT GTC CCA GGA CAT GAT AAT AAG ATG CAA TTT GAA TCT TCA TCA    11329
Arg Ser Val Pro Gly His Asp Asn Lys Met Gln Phe Glu Ser Ser Ser
    105                 110                 115

TAC GAA GGA TAC TTT CTA GCT TGT GAA AAA GAG AGA GAC CTT TTT AAA    11377
Tyr Glu Gly Tyr Phe Leu Ala Cys Glu Lys Glu Arg Asp Leu Phe Lys
120                 125                 130                 135

CTC ATT TTG AAA AAA GAG GAT GAA TTG GGG GAT AGA TCT ATA ATG TTC    11425
Leu Ile Leu Lys Lys Glu Asp Glu Leu Gly Asp Arg Ser Ile Met Phe
                140                 145                 150

ACT GTT CAA AAC GAA GAC TAGCTATTAA AATTTCATGC C                    11464
Thr Val Gln Asn Glu Asp
            155
```

(2) INFORMATION FOR SEQ ID NO:14:

(i) SEQUENCE CHARACTERISTICS:
(A) LENGTH: 28994 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: human
(F) TISSUE TYPE: placenta (iX) FEATURE:
(A) NAME/KEY: 5'UTR
(B) LOCATION: 1..15606
(C) IDENTIFICATION METHOD: E
(A) NAME/KEY: leader peptide
(B) LOCATION: 15607..15685

(C) IDENTIFICATION METHOD: S
(A) NAME/KEY: intron
(B) LOCATION: 15686..17056
(C) IDENTIFICATION METHOD: E
(A) NAME/KEY: leader peptide
(B) LOCATION: 17057..17068
(C) IDENTIFICATION METHOD: S
(A) NAME/KEY: intron
(B) LOCATION: 17069..20451
(C) IDENTIFICATION METHOD: E
(A) NAME/KEY: leader peptide
(B) LOCATION: 20452..20468
(C) IDENTIFICATION METHOD: S
(A) NAME/KEY: mat peptide
(B) LOCATION: 20469..20586
(C) IDENTIFICATION METHOD: S
(A) NAME/KEY: intron
(B) LOCATION: 20587..21920
(C) IDENTIFICATION METHOD: E
(A) NAME/KEY: mat peptide
(B) LOCATION: 21921..22054
(C) IDENTIFICATION METHOD: S
(A) NAME/KEY: intron
(B) LOCATION: 22055..26827
(C) IDENTIFICATION METHOD: E
(A) NAME/KEY: mat peptide
(B) LOCATION: 26828..27046
(C) IDENTIFICATION METHOD: S
(A) NAME/KEY: 3'UTR
(B) LOCATION: 27047..28994
(C) IDENTIFICATION METHOD: E (xi) SEQUENCE DESCRIPTION: SEQ ID NO: 14:

```
ACTTGCCTTA AAAGCTTTGC ATAGGTAGAC AACATTAGAT TAATTTCCTT GCTCACATCT     60

GTTCAAGAAA AATCATTTAA GTTATAAAAT ATAACAAACC TTCTGCATTA TAAGACTGAT    120

GTTTAGAAAT ATAAACATTT TATACATCAC CATTTAAATC TTTCTCCAAG GCTTCATCTT    180

TATAAAATAG TCCGGAAATT TCAGAGAAAG ATGAATCTGA TTTTCCAAGA GAGGACAGCT    240

GTGGACTATC TGGCACTGGA GACTAAATAA AGAAAGCAGG TACAGTCAAT AAGATCTTCA    300

GGACATATAC ATTTTGTTTA TTAAGAAAAA GCAAATAAAA CATTTTTCAG AAAAAGGCAA    360

ACATGCTAGA AAGCATATGA CTTAGTCATT TGAGTTTTTA TTATTAAGGA AATTTACAGG    420

CCCAAGAAAC ACCTTGCTCA ATATATTAAA TTTTATTTTG GTTTTCAACT AGACTTTGCT    480

TTTCATTTGT TTGTTTTTGT GACAAGTTCT CGCTCTGTCA CCTAGGCCAA AGTGTAGTGA    540

CACAATCTTA GCTCACTGTA GCCTCCTAGA TTCAAGTGAT CCTCCTGTCT CAGACTCCTG    600

AGTAGCTAGG ACTACAGGAA CATTCCACCA TGCCCAGCTA ATTTTGTTTT GTTTTGTTTT    660

GTTTTCAGAG ACAATGTATT GCAGCGTTGC CCAGGCTGAT CTGAAACTCT TAGCCTCAAA    720

CGATACTCCT GCCTCAGCCT CCCAAAGCAC TAGGATTACA GACATGAGCC AATGCGCCCA    780

GCCTTAAATT AGACTTTAAA TGTGGTTTTA AACTCCTGTT GAAAAAGCGT CTGGTATCTT    840

GAACCAGTAG ATGTTTTCAT AGCAATGAAG CTAAACTGTA ATTTAGACAG TAGCCAAATG    900

CTTGTGAAAT TTTGCTAAAT AATATAATCT TCAAGGGAGC AAATCATGTC CCAAATGCAA    960

AAGATCAACT GGTGGGGGCA GTAGTAAAAG ACAGGATACT GTGCTCTTTA AAAGGTCAGT   1020

AACTATAGTA CCTAGTTATC TTACTTATCA CAGCAAAATA ATTACATAAA ATCCTATGGA   1080

TCATAAAGGC ACAGACTCAC TTCTGTCTCT AGATCTCAAG CTACCAAAAA GAAATCTCCC   1140

AATAGTTTCT TGGAGGCCTA TACTTAGTGA AAAAGCAGCT GGAATCAACA TAGTTCCTCC   1200

TATGTTGTAG GACAATCCTA GCTCTGGGCA TACGAATACA TTAAATCCCA CTTATCTATA   1260

GAGCTTTCTT AAAGGGAAGA AATTTGAGTA GTATGTAAAA CAGAATAAAA GATTAAGGCT   1320
```

-continued

```
CCATAGGCAT ACAGCTTACC TCCAATTCTC TTGGCCTCTT GCAATTTCTA TTATCAGGCT   1380
TTACAAGGTG ATTTGCCATC ATATTCCGAA GGCACCAGCT ACAAAGCTTA GAACAATGCC   1440
AGATTTAGGT ACAAACTCCA TGCTACAAGC TCTCTGGAAT CCTTCCCTGT TTCCCACTCC   1500
TACTGCTGAT GTTAATTTAG ACTGTCATTA TCTGTCACTT TCCTAAACTC AATTTCTCCC   1560
TCCTCTAAAT CATTCTATCA ACTGCTATTT GGGTAATCTT TCAAAACTTT GATTACTGCA   1620
TTCCTTTAAC TCAAAAACTT TCATTGTTCC AGAATAAGTT GAAATTCCAT GATATGGCCT   1680
TCAAGGTCCT GTATTATCTG GTGCAAGCCT ACTAGTCCCA TCATTTTCAA CTACTCCTCT   1740
CTATGTACTT AGCCAAATGA GTCTCTCTGG CAATTCTGCC TTGTTTCAGG ACTGGCTCAG   1800
TTAAGATTCT TTTATCTTCG GCCGGGCGCG CTGGCTCACG GCTGTAATCC CAGCACTTTG   1860
GGAAGCTGAG GCAGGAAGAT CACCTGAGGT CGGGAGTTCG AGACCAGCCT GGCCAGCATG   1920
GTGAAACCCT GTGTCTACTA AAAATCCAAA CATTAGCCAG GCGTGGTGGC AGGCGCCTGT   1980
AATCCCAGCT ACTTGGGAAG CTGAGGTGAG AGAATCGCTT GAACCCAGGA GAGGGAGGTT   2040
GCAGTGAGCC GAGATTGTGC CATTGCACTC CAGCCTGGGC AACAGAGCGA GACTCCACCT   2100
CAAAAAAAAA AAGGATTCTT CTATCTTCAC AAAATCTTAA TGTTTAAACA GGTCTTACAG   2160
TTCATCTAAT TCAATCTCAT TTTTTACAAG TGAGAAAACA GGGACAGTGA CGGTGGATCA   2220
AGTGACACCA GTAAGACTGA GCTAAATTAG AACCGAGATC TCACTCGAGT CTGAGGTTAT   2280
TCCCACTGTC CAACCTTACT TTAAAGTAGC TTCAAATTTT ACTTTTACTT TTCCATAAAT   2340
TCGGAAGGGA TTTTCCCTAG GAGTCCAAAT GTTGAAACCT GGAAGGGTAT AGTCTCTGTG   2400
TCTTTGAGAT GAGGGGAGCC CTGTCCATAT TCAAGTTATC AATTGACTTT GTTGTTTTTG   2460
AGAAACGATG CTGATTTGGG TAACTTTAAC ACATCTGTTT GATTAGTCCT ATAAAATATG   2520
CATATATAGA AGACAGAAAG AGCAACAACA AATTTGAAAG ATGCTTGTTA AGTAAATTCT   2580
GTATCGTACG TGTCCATTCC TGCCAGTACC TTTATAGTAT GTAAGTTTAC GTGCTGTAAT   2640
AGTATTAATA GTATCTAGAA AATACTACAC ATGCACAGCA GTGCTAACTT TGCCTTGGGA   2700
GTTGGAAAAT ACTTCAGAGA AGCCAACAGG CAGATTTTTC TCTCTTCCCT TCCCCTTCTA   2760
ATTTTCCCTT TCCCCTTCAC CCCCTTCTCT TCTCTCCCCA AGTAACACTG TGCACCTATG   2820
TCAAACGAAA ACTTATAATC AAGTAACTGT TTCTGCAAAA ATAAGTTCGT TTTCCTGTCA   2880
TGGCTCAAGG CCTCAGCAGA TCCAGGCCTG GTGGACGGGC TGGTCTTCGT CGTGTGCCAA   2940
ACACTGACCA CTGCCCTGGC TCTGCCATCT TAGGCTTAGT GACCTGGCTG TTACTAAGCA   3000
CTGTCCCCTC TGCCCCATGC AGCTGTCTCC TTCTAGTCTT CTCCCTCTTC TCAACGCGAT   3060
CCTAGCCCCT CAGGCCATTT CACCTCCATT TTCCCTCACT TCCCGCCGCC CCTCCGCACT   3120
TCCTCCCTAC TGTTGTTTCC GCCCCACTAG AGCCCCTCAG AGAAAGTTTC CATCCTCGCA   3180
CCCTTCCTTG TGTCACAGCC CGTCACATTC TCACAGGCGC CCATCCCTCC AGCCCCACCC   3240
CAAGGCCAAT GTACTTCGCG GTATGGGGAC CTTCCTCGTC AGCGAACGCG AGGGAGTGAA   3300
GACCCTGGGC GCGGGGTGCT CGGACTTCGG GGGTGGAGGT GGGAAGCGCG CCGCACTCCC   3360
AGCAGCCCCT GCACGAGTCA CGTGACAGCT CTCCCACCAC CACCCCCCCC AACTTCCCCA   3420
CCGTAGCCTC CCAGAGCCAG GCCCCACGGA AAGGCAGCTT TTTCCCGGTT TTCTCCCGCT   3480
CTTTCCCCTC CACTTGGAAT ACTCGTGAAA CAAAAATCTC TCCCTGCCAC CCTGTGTGTG   3540
TTTGAACCAG GAAAAAATCT GAAACTGGTC AAGAAAGAAC AAGGAAGACT TGCCAAAGCA   3600
AGGCCGGTGT GTGTCCCAGC AGCTTAGAAT CTCAGCAAAG GAACACAAAA TAGCACATCC   3660
```

-continued

```
ACGGCCTCTT TTCGAGTAAA ATTTACTTGG TTTGTTTGCA GGAAGGGTTT AAAACTGCGT   3720
TTGCAGATGC TCTGTTTGCA GGAAGGCTTT AATCACGTGT TCCCCTGGCC CACAAGCAAG   3780
GCTTTTAGAT CCAGAGCCTC AGTTACTGCC CCCTCTTCCT CTTTGGTGCA ACCAAACGTT   3840
CAGAATCACG CCTTCTTAGA AAATTCTTAC CCCGGGTGTG TCAATAAGTT AAGTCTAATT   3900
GGCAACAGCT ATCAAAAAGT GTTGCATAAC ACACATGGCT CACATAATTG TAGCTTTGCC   3960
TCATCGGGTG TTTTAATGCG GAGGCTTTGA CCTGCAATTT CAAAGATATA CATTCCAAGC   4020
TTACGCCCAG TTAGTGGATG TGGAAGAAAA AAAAAAGCAA ATTACCTCAT AACACAAAGG   4080
TCAATAACAC ACATCCATAA GCTCCAGGTA CAAAATCTTA CATCTTAGAG AACTATATTT   4140
AACATTTACA TACATTACTA AGGTTTTTTT TTTCCTTTTG CTTGATTAAA TGTTAGTTAT   4200
CATTAAGTCT TGGAATTATT CTGTGTGTGT ATATTTATTT GCTGTTTGTG AAGAAGCCGG   4260
TTGTTTTAAA TAAGTTCCTA GAAAATAAGC GCTCAATGTG TTTAATCTGA GTTGCTAATA   4320
TTGTGAAATA TAGGCCACAT AATACTAGCC TAGATAACTA TGGCGAAGTA AGGAGTCTCA   4380
AACACTGTCC CAGAACAATA GCAATCTGTG TTGAATTTTT ACCCTCTGTG GTAAAATGAA   4440
GGGAAAAGGA ATGAAGTTTT AGTTTGCCTT AATTTTTATC TTTATTGTTT CAGACTCTTC   4500
AGCAGTATAA AGTTTTCATC AAGTCAAATA TATTCACTTT AAAGTGACTG TGCTTTATTC   4560
TGATACCATG TCCTTCCTAA TTTGGGGGGC CAGGTGAGAT AAGTTTTATG AAATAAAAAG   4620
ATTAAAAATT CTTACATTTT TAGTGTCCTT CCTTGGTAAA ATGTAGAGTT GTCCACTGTG   4680
TTTATCTCCT CCTCCTTATT ATCATGGTTG CTGTTATTAT TTTTAATGGT TCATTAAACC   4740
CAAGGGTCTG GGAAATACTC ATGGAATTCA TCTCACAGCC TTCACACTGT ATGATATTTA   4800
AACAGGTGGT TGTCCATCTG ATTCTTAAAA TATTTCCAAG AAAAATGATT CCACCTAATG   4860
CATAAATGCT TTCATCAGAT TAAGAGAACA CCATGGACAT TTTATTTTAT TTTATTTTTT   4920
AAATATTAAC TTCCATTGCA TAAGCTAAAT GGGTAGGAAT AAGTGAGATG ATATTGTTAT   4980
CTAGAGCTTT AAAATATTCA AAGGGCTGTC ATCATTATCT CATTTAATCT TTGAAAACAA   5040
CTCTATGAAG TACAAAGGAC ACTGAGACAT TTGTTGCTCT ATATCAAAGA AAAAAGTGTT   5100
TGTCCCAAAA CTTCAAAATG TGTAAATTAC ACATTCTGCA TCTTTACAGC TGGAGAAAAT   5160
TCACTGGCAA TGGAATATTT AAAATTAGAG CTTGCTTAGT GTGCTGCTTC TGATCACTAC   5220
TTGATCCCAC TTCGTGCTTT CATGTTAATT GGCCCAATTG GACTCTACAG TTGGAAGGTG   5280
AAAACTTACT ATTTCAACTT GAGTCACGTA TGTATTCTTA TCATATACTT CTTAAAGGTA   5340
CTATTTTTTT TCTTCTGATA GTCACCACAC CAAGCACTTC CAGCCACCCT GCCACAGACT   5400
TCCTTTGTAA TCACTGTTGA AGGACATGAT GTTTTTATGA CTTCCCGAAA TGAAAACCCT   5460
ATCTTGTTTT TAAAACAAAC AAACCAACAA AAAGTAGTGT TTATGTAAGC ATTTTGTTCC   5520
CTGACTCTAG GAACCCCTCT GTTTTTATAT CAACTCTGTA CTGGCAAAAC ACAAAAACAA   5580
AATGCCACCT TGCTAATTCC CTTCCTAGCA AAGTAATACA GTTTAGCACA TGTTCAAGAA   5640
AAAAATGGCT AAGAAATTTT GTTTCCACTA ATTATTTTCA AGACTGTGAT ATTTACACTC   5700
TGCTCTTCAA ACGTTACATT TTATAAGACT ATTTTTTAAC ATGTTGAACA TAAGCCCTAA   5760
ATATATGTAT CCTTAAATTG TATTTCAAAT ATTTTAGGTC AGTCTTTGCT ATCATTCCAG   5820
GAATAGAAAG TTTTAACACT GGAAACTGCA AGTAAATATT TGCCCTCTTA CCTGAATTTT   5880
GGTAGCCCTC TCCCCAAGCT TACTTTCTGT TGCAGAAAGT GTAAAAATTA TTACATAAAA   5940
TTCTAATGAT GGTATCCGTG TGGCTTGCAT CTGATACAGC AGATAAAGAA GTTTTATGAA   6000
```

-continued

```
AATGGACTCC TGTTCCACTG AAAAGTAAAT CTTAATGGCC TGTATCAACT ATCCTTTGAC   6060
ACCATATTGA GCTTGGGAGG AAGGGGAAGT CCTGAATGAG GTTATAAAGT AAAAGAAAAT   6120
ATTTGCAAAA TGTTCCTTTT TTTAAAATGT TACATTTTAG AAATATTTTA AGTGTTGTAA   6180
CATTGTAGGA ATTACCCCAA TAGGACTGAT TATTCCGCAT TGTAAAATAA GAAAAAGTTT   6240
TGTGCTGAAG TGTGACCAGG AAGTCTGAAA ATGAAGAGAG ACAGATGACA AAAGAAGATG   6300
CTTCTAATGG ACTAAGGAGG TGCTTTCTTA AAGTCAGAAA GAGATACTCA GAAAGAGGTA   6360
CAGGTTTTGG AAGGCACAGA GCCCCAACTT TTACGGAAGA AAAGATTTCA TGAAAATAGT   6420
GATATTACAT TAAAAGAAGT ACTCGTATCC TCTGCCACTT TATTTCGACT TCCATTGCCC   6480
TAGGAAAGAG CCTGTTTGAA GGCGGGCCCA AGGAGTGCCG ACAGCAGTCT CCTCCCTCCA   6540
CCTTCTTCCT CATTCTCTCC CCAGCTTGCT GAGCCCTTTG CTCCCCTGGC GACTGCCTGG   6600
ACAGTCAGCA AGGAATTGTC TCCCAGTGCA TTTTGCCCTC CTGGCTGCCA ACTCTGGCTG   6660
CTAAAGCGGC TGCCACCTGC TGCAGTCTAC ACAGCTTCGG GAAGAGGAAA GGAACCTCAG   6720
ACCTTCCAGA TCGCTTCCTC TCGCAACAAA CTATTTGTCG CAGGTAAGAA ATATCATTCC   6780
TCTTTATTTG GAAAGTCAGC CATGGCAATT AGAGGTAAAT AAGCTAGAAA GCAATTGAGA   6840
GGAATATAAA CCATCTAGCA TCACTACGAT GAGCAGTCAG TATCAACATA AGAAATATAA   6900
GCAAAGTCAG AGTAGAATTT TTTTCTTTTA TCAGATATGG GAGAGTATCA CTTTAGAGGA   6960
GAGGTTCTCA AACTTTTTGC TCTCATGTTC CCTTTACACT AAGCACATCA CATGTTAGCA   7020
TAAGTAACAT TTTTAATTAA AAATAACTAT GTACTTTTTT AACAACAAAA AAAAGCATAA   7080
AGAGTGACAC TTTTTTATTT TTACAAGTGT TTTAACTGGT TTAATAGAAG CCATATAGAT   7140
CTGCTGGATT CTCATCTGCT TTGCATTCAG ACTACTGCAA TATTGCACAG AATGCAGCCT   7200
CTGGTAAACT CTGTTGTACA CTCATGAGAG AATGGGTGAA AAAGACAAAT TACGTCTTAG   7260
AATTATTAGA AATAGCTTTC ACTTTAGGAA CTCCCTGAGA ATTGCTGCTT TAGAGTGGTA   7320
AGATAAATAA GCTTCTCTTT AAACGGAATC TCAAGACAGA ATCAGTTACA TTAAAAGCAA   7380
ACAAAAAATT TGCCCATGGT TAGTCATCTT GTGAAATCTG CCACACCTTT GGACTGGGCT   7440
ACAATTGGAT AATATAGCAT TCCCCGAGAT AATTTTCTCT CACAATTAAG GAAAGGGCTG   7500
AATAAATATC TCTGTTTGAA GTTGAATAAC AAAAATTAGG ACCCCCTAAA TTTTAGGGCT   7560
CCTGAAATTC GTCTTTTTGC CTATATTCAG CTACTTTACG TTCTATTAAA TCTTCTTTCA   7620
GGCCAGGTGC ACTAGCTCAT GCCTAGAATC TCAGGCAGGC CTGAGCCCAG GAATTTGAGA   7680
CCAGCCAGGG CAACACAGTC TCTACAAAAA AATAAAAAAT TACCTGGGTG TGTTGGTGCA   7740
TGCCTGTAGA ACTACTCAGG ATGCTGAGGA CTGCTTGAGC CCAGGATAGC CAAATCTGTG   7800
GTGAGTTCAG CCACTAAACA GAGCGAGACT TTCTCAAAAA AACAAACAAA AAAACAAACA   7860
AACTTCCTTC AAAATAACTT TTTATCTGCA ATGTTTTCCT ATTGCCTGTG AGATTAAATT   7920
TACTCTTTTA CCTGATTTCC AAAGCCCTCC ATAATCTAAT CCGACTTTAC CTTGTGTTCA   7980
CTGCAAAATA GCAGGACTGT TCCACTACAA TCCAAAAATC ACAGGTTGGG TGCAGTGGCT   8040
CACTCCTGTA ATCCCAACAC TTTGGAAGGC CAAGGCAGGT GGATTGCTTC AGCTCAGGAG   8100
TTCAAGACCA GCCTGGGCAA CATGGCAAAA ACCCTGTCTC TCCAAAACAT ACAAAAATTA   8160
GCCAGATGTG GTAGTATGTG CCTGTAGTCC CAACTACTCA AAAGGCTAAG GCAAGAGGAT   8220
CACTTGAGCC CAGGAGGTCA AGGCTACAGT GAGCCATGTT TACTGTGTCA CTGCACTCCA   8280
GCCTGGGTGA TAGAGCAAGA CCATGTCTCA AAAAAAAAAA AAAGAAAAGA AAAGAAAAAA   8340
```

-continued

```
ACATCGCTCT ATTCAGTTCA CCCCCACCAC AACATTGTTT TGATTATCAC ATAAATGCTG   8400
GTCCATTGCC TTCTCTATCT ATTCAAATCT TTAAGCATTC TTTGAGATTC AACTCAATTC   8460
TCCTTTTCAA ACTAGGCCAT TTAAACTACA TCAGTTCCAT TTTGATTTTC TTGCTTTGAG   8520
TCTACAGACT CAAAAACAAA AACTTAAAAA CTTATTTTTT AAGTTTTCTG CTACTCTCAC   8580
TTCTTCAACA CTCACATACA CGCATTCATA ATAAGATGGC AGAATGTTCA AGGATAAAAT   8640
GATTTATAGA ACTGAAAAGT TAGGTTTTGA TCTTGTTGCT GTCAAGATGA CTACCTACCT   8700
GATCTCAGGT AATTAATTAT GTAGCATGCT CCCTCATTTC ATCCCATACC TATTCAACAG   8760
GATTGGAATT CCACAGCAAG GATAAACATA ATCATAGTTG CTTTTCAAGT TCAAGGCATT   8820
TTAACTTTTA ATCTAGTAGT ATGTTTGTTG TTGTTGTTGT TGTTTGAGAT GGAGCCCTGC   8880
TGTGTCACCC AGGCTGGAGT GCAGTGGCAC GAACTCGGCT CACTGCAACC TCTGCCTCAT   8940
GGGTTCAATC AGTTATTCTG CCTCAGTGTC CCAAGTAGCT GGGACTACAA GGCACATGCC   9000
ACCATGCCTG GCTAATTTTT GTATTTTTAG TAGAAACAGG GCTTCACCAT GTTGGCCAGG   9060
CTGGTCTCGA ACTCCTGACC TCAAGTGATC CAGCCGCCTC GGCCTCCCAA AGTGCTGGGA   9120
TTACAGGCAT AAGCCACCGT GCCCAGCCTA ATAGTATGTT TTTAAACTCT TAGTGGCTTA   9180
ACAATGCTGG TTGTATAATA AATATGCCAT AAATATTTAC TGTCTTAGAA TTATGAAGAA   9240
GTGGTTACTA GGCCGTTTGC CACATATCAA TGGTTCTCTC CTTACAGCTT TAATTAGAGT   9300
CTAGAATTGC AGGTTGGTAG AGCTGGAACA GACCTTAAAG ATTGACTAGC CAACTTCCTT   9360
GTCCAAATGA GGGAACTGAG ACCCTTAAAA TTAAGTGACT TGCCCCAGAC AAAACTGGAA   9420
CTCATGTGTC CTAATTTCCA TCATGAAATT CTACCATTCA CTAGCCTCTG GCTAGTTGTC   9480
AAAGTATTGC ATAACTAAAT TTTTATGTCT GTTTTAAAGA ACAAATTGTC ACTGCTTACT   9540
CCTGGGAGGG TCTTTCTGAG GTGGTTTATA ACTCTTAAAA AAAAAAAAGT CAGTAGTCTG   9600
AGAATTTTAG ACGAAATAGT CAAAGCATTT TTATCCAATG GATCTATAAT TTTCATAGAT   9660
TAGAGTTAAA TCAAAGAAAC ACGGATGAGA AAGGAAGAGG AAAATTGAGG AGAGGAGGAA   9720
TGGGGATGAG AACACACTAC TTGTAATCAG TCATAGATGT ACTGAGAACT AACAAGAAGA   9780
ATTGTAAGAA AATAAGAATG AAGAATTCAA AATCAACACA TGAAATAAAA AGAAACTACT   9840
AGGGAAAAAT GGAGAAGACA TTAGAAAAAT TATTCTATTT TTAAAATTCT GTTTTCAGGC   9900
TTCCCTCCTG TTCTTCCTCC TTCTCATTGG TTTTCAGGTG GAGGGAAAGT TTAAGATGGA   9960
AAAAATATAT ATATTCTACA CATCCCTTTC TACGCTGTTG TCATGGCAAC AAGGTTTATC  10020
ATAGCAAACT TTTATTCATA CAACATTTAT TGAGTTCTTA CTGTGTGGTA AGCTCTTTCC  10080
AGGTGTTGAA AATTCAGGGG AAAAAAGACA ACTCATTGTC TTAAAACTCA GATGAAAGCT  10140
GAACAGACCT ATTTTTAATC AAAGTAATCT CAATTTAGGG TAGTAAGAGC TATTTAAGAA  10200
GCATGAACAG GTGTGAAGGA GGTAGGACTC TGAGGAGAGA ATAGTTAGCT AGGAATGAAA  10260
GAGCAGAGAA GTTTTCCTAG AGGAACTATT AAAGCTGGGA GTTACGGGAT GAAAGATGAG  10320
GCAGGGTTTG CAGGCAAAAA AAAAAAAAAG GCAGGGGAAG GGGAAGTTCT GGCCTGGCAG  10380
AGAGAATAAC TGTGGCAACA ATGGAGGAGA GTCTGGAAGC AAGAAAACCA AGTAGAAGAG  10440
TATTAAAATA GAAGATGCCA GGGGTAATGA GGGCTTGATT TAAAACAGTG CTGTTGGAGA  10500
TGGAGAGGAG ATACCAAATT CTGGAGACAT TTCTGAGTTA GAACCTACAG TATTTATCAG  10560
ACAAGGGAAA GATTAGACAA AGGAGTTAAG AATGACTCCC AGGTTTCAGT TTGGGGCAGG  10620
TAACTAGGAC ATGTTTTGAA AAGTAATGTA TTGGATCTCT TACCATTGGA ACTATGTATG  10680
```

-continued

```
TGGAGCCAAA TTAAAATTTG TACATGTATA TAACTCTCCC CCCACCACCA GTAACTACTT  10740
CCCTAACTCT CTACTTTGTA GCCAGACTTC CTAAAAGAAT AGTTTGTAGT CACTGTCTTT  10800
ACTTTTCCCC TCCCATTCTG TCCTAGATAT TTGTCCACCT ACCATCTGCT GCCTCCACTT  10860
TACCCAAACT GTTCTACGGT TGCCCAAAAC TTCCTAATTG CCAAATTCAA TGAACAAGTT  10920
TAAGCTTATA TGTAAATTAG GAGCTCTACA GTTTGATTTC GAGCAGCCCC TCCTGAAACC  10980
CTTTCTCTTT CGACTTCTGT GACACATCTC AGATTTACAA AACTGAACTA ATTATTTTAC  11040
ACTTGAGCTG TATTTTCGTT CTTCTTTCTT GATGAATGAG GTAACCACTC AACAAATTGC  11100
CCAAGCCAAA AACTACGAAG TCATCCTCAG TTCCTCCTTC TTCTGTTTGA CCCACAACAG  11160
ATCAGCTGAG AAATCCCGCT GTTTAGTATC TCTTGAATTC ATTACCTTAA TTTATAGCCT  11220
CATCAACTCT TAATTGTTAA AATTACTTCA GTAGTTGTTG TCTGACCTCT GTCCAATCTT  11280
GTTCAATCAG GTCCATTCTT TTGTTCTTGG TGGTGGTGGT GGTGTTGACA GAGTTTCGCT  11340
TTTGCTGCCC AGGCTGAAGT GCAGTGGAGC ACTTCACTGC AACCACAGCC TCCTGGGTTT  11400
AAGCAGTTCA CCCTCCCGAG TAGCTGGGAC TACAGGTATG TGCCACCACA CCCAGCTAAT  11460
TTTGTGTTTT CAGTAGAGAC AGGGTTTCAC CATGTTGGTC AGGCTGGTCT CAAACTCCTG  11520
ACCTCAAGCA ATCCACCCAC CTCAGCCTCC CAAAGTGCTG GGATTACAGG CATGAGCCAC  11580
TGCACACGGA CCAGATCCAT TGTTTATGTT GCTTCTAGAG TGAGTTTTTA AAACACAAAT  11640
TTGACCATAT CTTTCTCCAA TTTAAGTCAG TATTTTTTTT TTCAGGAAAA AACAGTTCAA  11700
ACTCTTTAGT CTGCTTACAC AAGGCCTTTG TAGTCTGACT CTTCTTTCCA AGCTTTCATC  11760
AAAGTATACT GCAAGTTACA TTTTATGTGA ATTGAATTAG GCAACGGTAT AAAAATTATA  11820
GTTTATATGG GCAAAATGGA AATAATGTTA ACTCTTCCAA ATAGTTTATC TAGAATGACA  11880
TAATTTCAAA GCTGTCAGGT CAAATGAGTT ATAAACTGTT AACACTATTG CCACATGCAA  11940
GTGTCTCTTA TACTTGGTAG AATTATCTGC TTCCATGTCA TTATTATGTA AATTAGACTT  12000
TAAATAACTC AGAAGTTCTT CAGACATACA GGTTATTATT GTGCTTTTTA AACATAATTT  12060
TAAATAATTT TATATATGAT AATGTTATCC AAGTGCTAAG GGATGTATTG TTACTGCTGT  12120
GCAAAAAAAA AAAAAAAAAA AACTCCAAAT AAATATGTTG AAACCAAGTT TATATGCAAG  12180
AAAACAATAT TAAAAAGGCC AAAGTACCAC CATAATAGGC TGTGTGGAGA CGGCAGGCTA  12240
CAAAACACTA GTAATAATGC TGAGAAAGTT GAAAAAAGAA AGAAAGCAAC AATATGCTTT  12300
GGTTGTTGTA GGTTTATGTA CTCCAAGAAT ATCTCCTCTC AAACTTTTAC GTTTTTTCCA  12360
AAGAAAAGTT AACTTTGGCT GGGCGCAGTG GCTCTTGCCT GTAGTCCCAG CCTTTGGGAG  12420
GCCAAGGCGG GCAGATCACC TGAGGTCAGG AGTTTGAGAC CAGCCTGACC AAAAATGGAG  12480
AAACCCGCCC CCCTCACTAC TAAAAGAATA CAAAATTAGG CCGGGCACAG TGGCTTACCC  12540
CTGTGATCCC AGCACTTTGG GAGGCCGAAG CAGGAAGATC ACCTGAGGTC AGGAGTTCGA  12600
GACCAGCCAT GGAGAAACCC GTCTCTACTA AAAATACAAA ATTAGCCGGG CGTGGTGGTG  12660
CATGACTGTA ATCCCAGCTA CTCAGGAGGC TAAGGCAGAG AATCACTTGA ACCCAGGCAG  12720
TGGAGGTTGC AGTGAGCCGA GATCGTGCCA TTGCACTCCA GCCTGGGCAA CAAGAGCGAA  12780
ACTCTGTATC CAAAAAACAA AAGAAAAGAA AAGGTAACCT TGAACTATGT GAGATCTTTA  12840
GAAATGCATT CTTTCTGTAA AATGTGACTA CATTTGCCTT ATTTATGGTA AAAATGTTGA  12900
GGCCTCAAAC AACCCATATT TTCTCGGTCT CCCCGCTGCC TAGCCTTTGT TCACATTGCT  12960
TCTTCTTGGT GGAAGCTCTT CCTCTGGCCT TGAAAATGCC TGCTTCTCTT TCAAGGTAGC  13020
```

-continued

```
ACAGTCATCA CTTTCTGTGG TAACCTTCTC CAGCACCATC AAACAGAAAG AATGAATCTC  13080
TTGTAAATTC AGCTCTTACG TCATTCATTA CATTATTTTG TAACTCTTTA TAGATTCTTC  13140
TCTCCCACTA GACTCTGAGT CACTGGAGAG TAGGAGCCAA CTCTCATTCA TGTGTGGTTT  13200
GGTCAGCTAC TGGCCACATT CCTGATGCAT AGTTAATGCT CAAACCTTAA CTGGTGAATC  13260
AGCTCAAATA TTGTCCTTCT CTAAATCCAT TCACTCATTG ACTAACTATG TACTCAAAAT  13320
AGTAAACACC AGTAATTTAA TCCAATTCCT GCCCATACTG CTTGGTACAT TTCAGGTGAA  13380
TTAGTTTGAT AAATATGTGT GTATTACATA ATATTAAAGT ATGTACAGAA GATCATGCTA  13440
ATCATAATTC ACAACTGATA ACTAATCAAA CATAAATGCT CTCAGGTTAA CAAATGTCTG  13500
CCTTCTCAGT TAATGCAGTC ATTAACAAAC ACCTTCTGAT GCTGATAATA GGGCCTTGTT  13560
CAGCAATGAA GCCATAAAGG TGAATAAAGA ACATGCCCTC GTGGAGCTCA CAGCCTAGTC  13620
ATTATTGTTC TGATTTTTAA TATTAATGTT GGTTTGGGTT TTGGTGAAAA ATGTTTAGAC  13680
TTATCTTAGT GATCTTTTCA TCCTTTGCTA TATTATTTTT CTCTAAGAGT CTTCCTTATC  13740
CCCTCCTTTA AAAAACTAGG TGATAATTCT AAATTGTAAA TTTAAATATT ATAAATAGCT  13800
TATAAAATTT AATATTTATA ATATTTAAAT GTTTGATAAA TATTTAAATT TTATAATATT  13860
TAAATGTTTA TTTAAATTCA TTTGTACATC AGTTTTTATT TTATTTAAAT GTGTTGGCCA  13920
GGCATGGTGG CTGACACCTA TAATCCCAGA ACTTTGAGAG GCCAAGTCAG GCAAACCATT  13980
TGAGCTCAGG AGTTTGAGAC CACCCTGGGC AACGTGGTGA AACCCTGTCT CTACCAAACA  14040
TATGAAAACT TATCTGGGTG TGGTGGCACG CATCTGTGGT CCCAGATGGG AGTCCCAGGC  14100
TAAGATGGGA GAATCGCTTG AACCCAGGTG AGAGGGGTGG GGTGGATGTT GCAGTGAGCT  14160
GAGATCGTGC CACTGCACTC CAACCTGGGT GACAGAGTGA GACTCCATCT CAAAAAAAAA  14220
AAATGTTATC TAAATAAGAT AAATTTAATA ACTGTTCGCA CTTAGATGAG CATAAGGAAC  14280
TAAACCTAGA TAAAACTATC AAATAAGGCC TGGGTACAGT GACTCATGCC TGTAATCTCA  14340
AGCACTTTGG GAGGCCAAAA TTATACAAAG TTAGTTGTAT AACACCAACT AACAACTATT  14400
TTGGGGTTAG CTTAATTCAG ATTAATTTTT TTTAAACTGA GTTTTAAATT CCTGCTTACT  14460
CTACCATACA TGCTAGGCCT CATATTATGC TAGAAAAATT TTGAGCACAG ATTTATGAAT  14520
ACTCTCCTGC ATACCATTTA ATTTTTAAAC AAATTTTAAT GCAGTATATA TGTGCCTTTT  14580
TACCAACACA TTAAATAATA AGATCTACTG TGAGGACTAA ATTTCTGTAA TTTCAAAGTA  14640
GTAATGAGTT TAAACCATGT CTCAAGATCT CTGCAATAAC TGTAGCACAA CAGAAAATAG  14700
GTATTTCTAT TAATGACAGA GTCACAAGTA CTACTAATAA TACTGTGGTT TGTTTCCTGC  14760
AACTAATCAT GGGAGGAATG CTAAATTTCA GAGGTTGGTG AAAATACATG TGTATTTTTT  14820
TCCCCATCCA AGTTCACAGA TTTCTCACAC TGAGAACTCC TATTCCATAA CAAAATTCTG  14880
GAAGCCTGCA CACCGTATTG GAAGAAGGGC AGAAAGGAAA AGCAAATGGA AGGATTTAAA  14940
TTTTTTTCAA ATCCTGTATC CCTTGATTTT ACAGCAAGAT TGTATTTATG TATTACTTGT  15000
GTTAAAAATA TAGTATAATC GAGACTCCAG ATCAAAAATC ACCGCAGCTC AGGGAGAAAG  15060
AGGGCCACCA AATGCCAGAG CCCTTCAGCC TTCTCCCACC CTGCCTGTAC CCTCAGATGG  15120
AAGCACTTTT TTATCATTGT TTCACCTTTA GCATTTTGAC AATGAAGTCA CAAACCTTCA  15180
GCCTCTCACC CATAGGAACC CACTGGTTGT AAGAGAAGGA TGAAGCCAGT CCTTCCTAAA  15240
GGGCACGATT AGATGTGTTT ATGGCATCCT CAGGTGAAAC TATATTTATA TTGACAATAT  15300
ATTTATATTT CTCAAGGAAT ACTAGAATAA TGATTCAGTT CAGTACTAGG CCATTTATCT  15360
```

-continued

```
ACCCTTTATA ATATTGTTTA ATGAGAAAAT GCTTTCTATC TTCCAAATAT CTGATGATTT  15420

GTAAGAGAAC ACTTAAACAT GGGTATTCAT AAGCTGAAAC TTCTGGCATT TATTGAATGT  15480

CAAGATTGTT CATCAGTATA CTAGGTGATT AACTGACCAC TGAACTTGAA GGTAGTATAA  15540

AGTAGTAGTA AAAGGTACAA TCATTGTCTC TTAACAGATG GCTCTTTGCT TTCATTAGGA  15600

ATAAAG ATG GCT GCT GAA CCA GTA GAA GAC AAT TGC ATC AAC TTT GTG GCA 15651
       Met Ala Ala Glu Pro Val Glu Asp Asn Cys Ile Asn Phe Val Ala
           -35                 -30                 -25

ATG AAA TTT ATT GAC AAT ACG CTT TAC TTT ATA G   GTAAGGC TAATGCCATA 15702
Met Lys Phe Ile Asp Asn Thr Leu Tyr Phe Ile Ala
    -20                 -15                 -10

GAACAAATAC CAGGTTCAGA TAAATCTATT CAATTAGAAA AGATGTTGTG AGGTGAACTA  15762

TTAAGTGACT CTTTGTGTCA CCAAATTTCA CTGTAATATT AATGGCTCTT AAAAAAATAG  15822

TGGACCTCTA GAAATTAACC ACAACATGTC CAAGGTCTCA GCACCTTGTC ACACCACGTG  15882

TCCTGGCACT TTAATCAGCA GTAGCTCACT CTCCAGTTGG CAGTAAGTGC ACATCATGAA  15942

AATCCCAGTT TTCATGGGAA AATCCCAGTT TTCATTGGAT TTCCATGGGA AAAATCCCAG  16002

TACAAAACTG GGTGCATTCA GGAAATACAA TTTCCCAAAG CAAATTGGCA AATTATGTAA  16062

GAGATTCTCT AAATTTAGAG TTCCGTGAAT TACACCATTT TATGTAAATA TGTTTGACAA  16122

GTAAAAATTG ATTCTTTTTT TTTTTTTCTG TTGCCCAGGC TGGAGTGCAG TGGCACAATC  16182

TCTGCTCACT GCAACCTCCA CCTCCTGGGT TCAAGCAATT CTCCTGCCTC AGCCTTCTGA  16242

GTAGCTGGGA CTACAGGTGC ATCCCGCCAT GCCTGGCTAA TTTTTGGGTA TTTTTACTAG  16302

AGACAGGGTT TGGCATGTT GTCCAGGCTG GTCTTGGACT CCTGATCTCA GATGATCCTC  16362

CTGGCTCGGG CTCCCAAAGT GCTGGGATTA CAGGCATGAA CCACCACACA TGGCCTAAAA  16422

ATTGATTCTT ATGATTAATC TCCTGTGAAC AATTTGGCTT CATTTGAAAG TTTGCCTTCA  16482

TTTGAAACCT TCATTTAAAA GCCTGAGCAA CAAAGTGAGA CCCCATCTCT ACAAAAAACT  16542

GCAAAATATC CTGTGGACAC CTCCTACCTT CTGTGGAGGC TGAAGCAGGA GGATCACTTG  16602

AGCCTAGGAA TTTGAGCCTG CAGTGAGCTA TGATCCCACC CCTACACTCC AGCCTGCATG  16662

ACAGTAGACC CTGACACACA CACACAAAAA AAAACCTTCA TAAAAAATTA TTAGTTGACT  16722

TTTCTTAGGT GACTTTCCGT TTAAGCAATA AATTTAAAAG TAAAATCTCT AATTTTAGAA  16782

AATTTATTTT TAGTTACATA TTGAAATTTT TAAACCCTAG GTTTAAGTTT TATGTCTAAA  16842

TTACCTGAGA ACACACTAAG TCTGATAAGC TTCATTTTAT GGGCCTTTTG GATGATTATA  16902

TAATATTCTG ATGAAAGCCA AGACAGACCC TTAAACCATA AAAATAGGAG TTCGAGAAAG  16962

AGGAGTAGCA AAAGTAAAAG CTAGAATGAG ATTGAATTCT GAGTCGAAAT ACAAAATTTT  17022

ACATATTCTG TTTCTCTCTT TTTCCCCCTC TTAG  CT GAA GAT GAT G   GTAAAGT  17075
                                     Ala Glu Asp Asp Glu
                                     -10

AGAAATGAAT TTATTTTTCT TTGCAAACTA AGTATCTGCT TGAGACACAT CTATCTCACC  17135

ATTGTCAGCT GAGGAAAAAA AAAAATGGTT CTCATGCTAC CAATCTGCCT TCAAAGAAAT  17195

GTGGACTCAG TAGCACAGCT TTGGAATGAA GATGATCATA AGAGATACAA AGAAGAACCT  17255

CTAGCAAAAG ATGCTTCTCT ATGCCTTAAA AAATTCTCCA GCTCTTAGAA TCTACAAAAT  17315

AGACTTTGCC TGTTTCATTG GTCCTAAGAT TAGCATGAAG CCATGGATTC TGTTGTAGGG  17375

GGAGCGTTGC ATAGGAAAAA GGGATTGAAG CATTAGAATT GTCCAAAATC AGTAACACCT  17435

CCTCTCAGAA ATGCTTTGGG AAGAAGCCTG GAAGGTTCCG GGTTGGTGGT GGGGTGGGGC  17495
```

-continued

```
AGAAAATTCT GGAAGTAGAG GAGATAGGAA TGGGTGGGGC AAGAAGACCA CATTCAGAGG  17555
CCAAAAGCTG AAAGAAACCA TGGCATTTAT GATGAATTCA GGGTAATTCA GAATGGAAGT  17615
AGAGTAGGAG TAGGAGACTG GTGAGAGGAG CTAGAGTGAT AAACAGGGTG TAGAGCAAGA  17675
CGTTCTCTCA CCCCAAGATG TGAAATTTGG ACTTTATCTT GGAGATAATA GGGTTAATTA  17735
AGCACAATAT GTATTAGCTA GGGTAAAGAT TAGTTTGTTG TAACAAAGAC ATCCAAAGAT  17795
ACAGTAGCTG AATAAGATAG AGAATTTTTC TCTCAAAGAA AGTCTAAGTA GGCAGCTCAG  17855
AAGTAGTATG GCTGGAAGCA ACCTGATGAT ATTGGGACCC CCAACCTTCT TCAGTCTTGT  17915
ACCCATCATC CCCTAGTTGT TGATCTCACT CACATAGTTG AAAATCATCA TACTTCCTGG  17975
GTTCATATCC CAGTTATCAA GAAAGGGTCA AGAGAAGTCA GGCTCATTCC TTTCAAAGAC  18035
TCTAATTGGA AGTTAAACAC ATCAATCCCC CTCATATTCC ATTGACTAGA ATTTAATCAC  18095
ATGGCCACAC CAAGTGCAAG GAAATCTGGA AAATATAATC TTTATTCCAG GTAGCCATAT  18155
GACTCTTTAA AATTCAGAAA TAATATATTT TTAAAATATC ATTCTGGCTT TGGTATAAAG  18215
AATTGATGGT GTGGGGTGAG GAGGCCAAAA TTAAGGGTTG AGAGCCTATT ATTTTAGTTA  18275
TTACAAGAAA TGATGGTGTC ATGAATTAAG GTAGACATAG GGGAGTGCTG ATGAGGAGCT  18335
GTGAATGGAT TTTAGAAACA CTTGAGAGAA TCAATAGGAC ATGATTTAGG GTTGGATTTG  18395
GAAAGGAGAA GAAAGTAGAA AAGATGATGC CTACATTTTT CACTTAGGCA ATTTGTACCA  18455
TTCAGTGAAA TAGGGAACAC AGGAGGAAGA GCAGGTTTTG GTGTATACAA AGAGGAGGAT  18515
GGATGACGCA TTTCGTTTTG GATCTGAGAT GTCTGTGGAA CGTCCTAGTG GAGATGTCCA  18575
CAAACTCTTC TACATGTGGT TCTGAGTTCA GGACACAGAT TTGGGCTGGA GATAGAGATA  18635
TTGTAGGCTT ATACATAGAA ATGGCATTTG AATCTATAGA GATAAAAAGA CACATCAGAG  18695
GAAATGTGTA AAGTGAGAGA GGAAAAGCCA AGTACTGTGC TGGGGGGAAT ACCTACATTT  18755
AAAGGATGCA GTAGAAAGAA GCTAATAAAC AACAGAGAGC AGACTAACCA AAAGGGGAGA  18815
AGAAAAACCA AGAGAATTCC ACCGACTCCC AGGAGAGCAT TTCAAGATTG AGGGGATAGG  18875
TGTTGTGTTG AATTTTGCAG CCTTGAGAAT CAAGGGCCAG AACACAGCTT TTAGATTTAG  18935
CAACAAGGAG TTTGGTGATC TCAGTGAAAG CAGCTTGATG GTGAAATGGA GGCAGAGGCA  18995
GATTGCAATG AGTGAAACAG TGAATGGGAA GTGAAGAAAT GATACAGATA ATTCTTGCTA  19055
AAAGCTTGGC TGTTAAAAGG AGGAGAGAAA CAAGACTAGC TGCAAAGTGA GATTGGGTTG  19115
ATGGAGCAGT TTTAAATCTC AAAATAAAGA GCTTTGTGCT TTTTTGATTA TGAAAATAAT  19175
GTGTTAATTG TAACTAATTG AGGCAATGAA AAAAGATAAT AATATGAAAG ATAAAAATAT  19235
AAAAACCACC CAGAAATAAT GATAGCTACC ATTTTGATAC AATATTTCTA CACTCCTTTC  19295
TATGTATATA TACAGACACA GAAATGCTTA TATTTTTATT AAAAGGGATT GTACTATACC  19355
TAAGCTGCTT TTTCTAGTTA GTGATATATA TGGACATCTC TCCATGGCAA CGAGTAATTG  19415
CAGTTATATT AAGTTCATGA TATTTCACAA TAAGGGCATA TCTTTGCCCT TTTTATTTAA  19475
TCAATTCTTA ATTGGTGAAT GTTTGTTTCC AGTTTGTTGT TGTTATTAAC AATGTTCCCA  19535
TAAGCATTCC TGTACACCAA TGTTCACACA TTTGTCTGAT TTTTTCTTCA GGATAAAACC  19595
CAGGAGGTAG AATTGCTGGG TTGATAGAAG AGAAAGGATG ATTGCCAAAT TAAAGCTTCA  19655
GTAGAGGGTA CATGCCGAGC ACAAATGGGA TCAGCCCTAG ATACCAGAAA TGGCACTTTC  19715
TCATTTCCCC TTGGGACAAA AGGGAGAGAG GCAATAACTG TGCTGCCAGA GTTAAATTTG  19775
TACGTGGAGT AGCAGGAAAT CATTTGCTGA AAATGAAAAC AGAGATGATG TTGTAGAGGT  19835
```

-continued

```
CCTGAAGAGA GCAAAGAAAA TTTGAAATTG CGGCTATCAG CTATGGAAGA GAGTGCTGAA  19895

CTGGAAAACA AAAGAAGTAT TGACAATTGG TATGCTTGTA ATGGCACCGA TTTGAACGCT  19955

TGTGCCATTG TTCACCAGCA GCACTCAGCA GCCAAGTTTG GAGTTTTGTA GCAGAAAGAC  20015

AAATAAGTTA GGGATTTAAT ATCCTGGCCA AATGGTAGAC AAAATGAACT CTGAGATCCA  20075

GCTGCACAGG GAAGGAAGGG AAGACGGGAA GAGGTTAGAT AGGAAATACA AGAGTCAGGA  20135

GACTGGAAGA TGTTGTGATA TTTAAGAACA CATAGAGTTG GAGTAAAAGT GTAAGAAAAC  20195

TAGAAGGGTA AGAGACCGGT CAGAAAGTAG GCTATTTGAA GTTAACACTT CAGAGGCAGA  20255

GTAGTTCTGA ATGGTAACAA GAAATTGAGT GTGCCTTTGA GAGTAGGTTA AAAAACAATA  20315

GGCAACTTTA TTGTAGCTAC TTCTGGAACA GAAGATTGTC ATTAATAGTT TTAGAAAACT  20375

AAAATATATA GCATACTTAT TTGTCAATTA ACAAAGAAAC TATGTATTTT TAAATGAGAT  20435

TTAATGTTTA TTGTAG  AA AAC CTG GAA TCA GAT TAC TTT GGC AAG CTT GAA  20486
                  Glu Asn Leu Glu Ser Asp Tyr Phe Gly Lys Leu Glu
                      -5                  1               5

TCT AAA TTA TCA GTC ATA AGA AAT TTG AAT GAC CAA GTT CTC TTC ATT    20534
Ser Lys Leu Ser Val Ile Arg Asn Leu Asn Asp Gln Val Leu Phe Ile
            10                  15                  20

GAC CAA GGA AAT CGG CCT CTA TTT GAA GAT ATG ACT GAT TCT GAC TGT    20582
Asp Gln Gly Asn Arg Pro Leu Phe Glu Asp Met Thr Asp Ser Asp Cys
        25                  30                  35

AGA G   GT ATTTTTTTTA ATTCGCAAAC ATAGAAATGA CTAGCTACTT CTTCCCATTC  20638
Arg Asp
    40

TGTTTTACTG CTTACATTGT TCCGTGCTAG TCCCAATCCT CAGATGAAAA GTCACAGGAG  20698

TGACAATAAT TTCACTTACA GGAAACTTTA TAAGGCATCC ACGTTTTTTA GTTGGGGTAA  20758

AAAATTGGAT ACAATAAGAC ATTGCTAGGG GTCATGCCTC TCTGAGCCTG CCTTTGAATC  20818

ACCAATCCCT TTATTGTGAT TGCATTAACT GTTTAAAACC TCTATAGTTG GATGCTTAAT  20878

CCCTGCTTGT TACAGCTGAA AATGCTGATA GTTTACCAGG TGTGGTGGCA TCTATCTGTA  20938

ATCCTAGCTA CTTGGGAGGC TCAAGCAGGA GGATTGCTTG AGGCCAGGAC TTTGAGGCTG  20998

TAGTACACTG TGATCGTACC TGTGAATAGC CACTGCACTC CAGCCTGGGT GATATACAGA  21058

CCTTGTCTCT AAAATTAAAA AAAAAAAAAA AAAAAACCTT AGGAAAGGAA ATTGATCAAG  21118

TCTACTGTGC CTTCCAAAAC ATGAATTCCA AATATCAAAG TTAGGCTGAG TTGAAGCAGT  21178

GAATGTGCAT TCTTTAAAAA TACTGAATAC TTACCTTAAC ATATATTTTA AATATTTTAT  21238

TTAGCATTTA AAAGTTAAAA ACAATCTTTT AGAATTCATA TCTTTAAAAT ACTCAAAAAA  21298

GTTGCAGCGT GTGTGTTGTA ATACACATTA AACTGTGGGG TTGTTTGTTT GTTTGAGATG  21358

CAGTTTCACT CTGTCACCCA GGCTGAAGTG CAGTGCAGTG CAGTGGTGTG ATCTCGGCTC  21418

ACTACAACCT CCACCTCCCA CGTTCAAGCG ATTCTCATGC CTCAGTCTCC CGAGTAGGTG  21478

GGATTACAGG CATGCACCAC TTACACCCGG CTAATTTTTG TATTTTTAGT AGAGCTGGGG  21538

TTTCACCATG TTGGCCAGGC TGGTCTCAAA CCCCTAACCT CAAGTGATCT GCCTGCCTCA  21598

GCCTCCCAAA CAAACAAACA ACCCCACAGT TTAATATGTG TTACAACACA CATGCTGCAA  21658

CTTTTATGAG TATTTTAATG ATATAGATTA TAAAAGGTTG TTTTTAACTT TTAAATGCTG  21718

GGATTACAGG CATGAGCCAC TGTGCCAGGC CTGAACTGTG TTTTTAAAAA TGTCTGACCA  21778

GCTGTACATA GTCTCCTGCA GACTGGCCAA GTCTCAAAGT GGGAACAGGT GTATTAAGGA  21838

CTATCCTTTG GTTAAATTTC CGCAAATGTT CCTGTGCAAG AATTCTTCTA ACTAGAGTTC  21898
```

-continued

```
TCATTTATTA TATTTATTTC AG  AT AAT GCA CCC CGG ACC ATA TTT ATT ATA   21949
                           Asp Asn Ala Pro Arg Thr Ile Phe Ile Ile
                           40                  45

AGT ATG TAT AAA GAT AGC CAG CCT AGA GGT ATG GCT GTA ACT ATC TCT    21997
Ser Met Tyr Lys Asp Ser Gln Pro Arg Gly Met Ala Val Thr Ile Ser
50                  55                  60                  65

GTG AAG TGT GAG AAA ATT TCA ACT CTC TCC TGT GAG AAC AAA ATT ATT    22045
Val Lys Cys Glu Lys Ile Ser Thr Leu Ser Cys Glu Asn Lys Ile Ile
                70                  75                  80

TCC TTT AAG GTAAGACTG AGCCTTACTT TGTTTTCAAT CATGTTAATA TAATCAATAT  22103
Ser Phe Lys

AATTAGAAAT ATAACATTAT TTCTAATGTT AATATAAGTA ATGTAATTAG AAAACTCAAA  22163

TATCCTCAGA CCAACCTTTT GTCTAGAACA GAAATAACAA GAAGCAGAGA ACCATTAAAG  22223

TGAATACTTA CTAAAAATTA TCAAACTCTT TACCTATTGT GATAATGATG GTTTTTCTGA  22283

GCCTGTCACA GGGGAAGAGG AGATACAACA CTTGTTTTAT GACCTGCATC TCCTGAACAA  22343

TCAGTCTTTA TACAAATAAT AATGTAGAAT ACATATGTGA GTTATACATT TAAGAATAAC  22403

ATGTGACTTT CCAGAATGAG TTCTGCTATG AAGAATGAAG CTAATTATCC TTCTATATTT  22463

CTACACCTTT GTAAATTATG ATAATATTTT AATCCCTAGT TGTTTTGTTG CTGATCCTTA  22523

GCCTAAGTCT TAGACACAAG CTTCAGCTTC CAGTTGATGT ATGTTATTTT TAATGTTAAT  22583

CTAATTGAAT AAAAGTTATG AGATCAGCTG TAAAAGTAAT GCTATAATTA TCTTCAAGCC  22643

AGGTATAAAG TATTTCTGGC CTCTACTTTT TCTCTATTAT TCTCCATTAT TATTCTCTAT  22703

TATTTTTCTC TATTTCCTCC ATTATTGTTA GATAAACCAC AATTAACTAT AGCTACAGAC  22763

TGAGCCAGTA AGAGTAGCCA GGGATGCTTA CAAATTGGCA ATGCTTCAGA GGAGAATTCC  22823

ATGTCATGAA GACTCTTTTT GAGTGGAGAT TTGCCAATAA ATATCCGCTT TCATGCCCAC  22883

CCAGTCCCCA CTGAAAGACA GTTAGGATAT GACCTTAGTG AAGGTACCAA GGGGCAACTT  22943

GGTAGGGAGA AAAAAGCCAC TCTAAAATAT AATCCAAGTA AGAACAGTGC ATATGCAACA  23003

GATACAGCCC CCAGACAAAT CCCTCAGCTA TCTCCCTCCA ACCAGAGTGC CACCCCTTCA  23063

GGTGACAATT TGGAGTCCCC ATTCTAGACC TGACAGGCAG CTTAGTTATC AAAATAGCAT  23123

AAGAGGCCTG GGATGGAAGG GTAGGGTGGA AAGGGTTAAG CATGCTGTTA CTGAACAACA  23183

TAATTAGAAG GGAAGGAGAT GGCCAAGCTC AAGCTATGTG GGATAGAGGA AAACTCAGCT  23243

GCAGAGGCAG ATTCAGAAAC TGGGATAAGT CCGAACCTAC AGGTGGATTC TTGTTGAGGG  23303

AGACTGGTGA AAATGTTAAG AAGATGGAAA TAATGCTTGG CACTTAGTAG GAACTGGGCA  23363

AATCCATATT TGGGGGAGCC TGAAGTTTAT TCAATTTTGA TGGCCCTTTT AAATAAAAAG  23423

AATGTGGCTG GGCGTGGTGG CTCACACCTG TAATCCCAGC ACTTTGGGAG GCCGAGGGGG  23483

GCGGATCACC TGAAGTCAGG AGTTCAAGAC CAGCCTGACC AACATGGAGA AACCCCATCT  23543

CTACTAAAAA TACAAAATTA GCTGGGCGTG GTGGCATATG CCTGTAATCC CAGCTACTCG  23603

GGAGGCTGAG GCAGGAGAAT CTTTTGAACC CGGGAGGCAG AGGTTGCGAT GAGCCTAGAT  23663

CGTGCCATTG CACTCCAGCC TGGGCAACAA GAGCAAAACT CGGTCTCAAA AAAAAAAAAA  23723

AAAAAGTGAA ATTAACCAAA GGCATTAGCT TAATAATTTA ATACTGTTTT TAAGTAGGGC  23783

GGGGGGTGGC TGGAAGAGAT CTGTGTAAAT GAGGGAATCT GACATTTAAG CTTCATCAGC  23843

ATCATAGCAA ATCTGCTTCT GGAAGGAACT CAATAAATAT TAGTTGGAGG GGGGGAGAGA  23903

GTGAGGGGTG GACTAGGACC AGTTTTAGCC CTTGTCTTTA ATCCCTTTTC CTGCCACTAA  23963

TAAGGATCTT AGCAGTGGTT ATAAAAGTGG CCTAGGTTCT AGATAATAAG ATACAACAGG  24023
```

-continued

CCAGGCACAG TGGCTCATGC CTATAATCCC AGCACTTTGG GAGGGCAAGG CGAGTGTCTC 24083

ACTTGAGATC AGGAGTTCAA GACCAGCCTG GCCAGCATGG CGATACTCTG TCTCTACTAA 24143

AAAAAATACA AAAATTAGCC AGGCATGGTG GCATGCACCT GTAATCCCAG CTACTCGTGA 24203

GCCTGAGGCA GAAGAATCGC TTGAAACCAG GAGGTGTAGG CTGCAGTGAG CTGAGATCGC 24263

ACCACTGCAC TCCAGCCTGG GCGACAGAAT GAGACTTTGT CTCAAAAAAA GAAAAAGATA 24323

CAACAGGCTA CCCTTATGTG CTCACCTTTC ACTGTTGATT ACTAGCTATA AAGTCCTATA 24383

AAGTTCTTTG GTCAAGAACC TTGACAACAC TAAGAGGGAT TTGCTTTGAG AGGTTACTGT 24443

CAGAGTCTGT TTCATATATA TACATATACA TGTATATATG TATCTATATC CAGGCTTGGC 24503

CAGGGTTCCC TCAGACTTTC CAGTGCACTT GGGAGATGTT AGGTCAATAT CAACTTTCCC 24563

TGGATTCAGA TTCAACCCCT TCTGATGTAA AAAAAAAAAA AAAAAAGAAA GAAATCCCTT 24623

TCCCCTTGGA GCACTCAAGT TTCACCAGGT GGGGCTTTCC AAGTTGGGGG TTCTCCAAGG 24683

TCATTGGGAT TGCTTTCACA TCCATTTGCT ATGTACCTTC CCTATGATGG CTGGGAGTGG 24743

TCAACATCAA AACTAGGAAA GCTACTGCCC AAGGATGTCC TTACCTCTAT TCTGAAATGT 24803

GCAATAAGTG TGATTAAAGA GATTGCCTGT TCTACCTATC CACACTCTCG CTTTCAACTG 24863

TAACTTTCTT TTTTTCTTTT TTTCTTTTTT TCTTTTTTTT TGAAACGGAG TCTCGCTCTG 24923

TCGCCCAGGC TAGAGTGCAG TGGCACGATC TCAGCTCACT GCAAGCTCTG CCTCCCGGGT 24983

TCACGCCATT CTCCTGCCTC ACCCTCCCAA GCAGCTGGGA CTACAGGCGC CTGCCACCAT 25043

GCCCAGCTAA TTTTTTGTAT TTTTAGTAGA GACGGGGTTT CACCGTGTTA GCCAGGATGG 25103

TCTCGATCTC CTGAACTTGT GATCCGCCCG CCTCAGCCTC CCAAAGTGCT GGGATTACAG 25163

GCGTGAGCCA TCGCACCCGG CTCAACTGTA ACTTTCTATA CTGGTTCATC TTCCCCTGTA 25223

ATGTTACTAG AGCTTTTGAA GTTTTGGCTA TGGATTATTT CTCATTTATA CATTAGATTT 25283

CAGATTAGTT CCAAATTGAT GCCCACAGCT TAGGGTCTCT TCCTAAATTG TATATTGTAG 25343

ACAGCTGCAG AAGTGGGTGC CAATAGGGGA ACTAGTTTAT ACTTTCATCA ACTTAGGACC 25403

CACACTTGTT GATAAAGAAC AAAGGTCAAG AGTTATGACT ACTGATTCCA CAACTGATTG 25463

AGAAGTTGGA GATAACCCCG TGACCTCTGC CATCCAGAGT CTTTCAGGCA TCTTTGAAGG 25523

ATGAAGAAAT GCTATTTTAA TTTTGGAGGT TTCTCTATCA GTGCTTAGGA TCATGGGAAT 25583

CTGTGCTGCC ATGAGGCCAA AATTAAGTCC AAAACATCTA CTGGTTCCAG GATTAACATG 25643

GAAGAACCTT AGGTGGTGCC CACATGTTCT GATCCATCCT GCAAAATAGA CATGCTGCAC 25703

TAACAGGAAA AGTGCAGGCA GCACTACCAG TTGGATAACC TGCAAGATTA TAGTTTCAAG 25763

TAATCTAACC ATTTCTCACA AGGCCCTATT CTGTGACTGA AACATACAAG AATCTGCATT 25823

TGGCCTTCTA AGGCAGGGCC CAGCCAAGGA GACCATATTC AGGACAGAAA TTCAAGACTA 25883

CTATGGAACT GGAGTGCTTG GCAGGGAAGA CAGAGTCAAG GACTGCCAAC TGAGCCAATA 25943

CAGCAGGCTT ACACAGGAAC CCAGGGCCTA GCCCTACAAC AATTATTGGG TCTATTCACT 26003

GTAAGTTTTA ATTTCAGGCT CCACTGAAAG AGTAAGCTAA GATTCCTGGC ACTTTCTGTC 26063

TCTCTCACAG TTGGCTCAGA AATGAGAACT GGTCAGGCCA GGCATGGTGG CTTACACCTG 26123

GAATCCCAGC ACTTTGGGAG GCCGAAGTGG GAGGGTCACT TGAGGCCAGG AGTTCAGGAC 26183

CAGCTTAGGC AACAAAGTGA GATACCCCCT GACCCCTTCT CTACAAAAAT AAATTTTAAA 26243

AATTAGCCAA ATGTGGTGGT GTATACTTAC AGTCCCAGCT ACTCAGGAGG CTGAGGCAGG 26303

GGGATTGCTT GAGCCCAGGA ATTCAAGGCT GCAGTGAGCT ATGATTTCAC CACTGCACTT 26363

-continued

```
CTGGCTGGGC AACAGAGCGA GACCCTGTCT CAAAGCAAAA AGAAAAAGAA ACTAGAACTA  26423

GCCTAAGTTT GTGGGAGGAG GTCATCATCG TCTTTAGCCG TGAATGGTTA TTATAGAGGA  26483

CAGAAATTGA CATTAGCCCA AAAAGCTTGT GGTCTTTGCT GGAACTCTAC TTAATCTTGA  26543

GCAAATGTGG ACACCACTCA ATGGGAGAGG AGAGAAGTAA GCTGTTTGAT GTATAGGGGA  26603

AAACTAGAGG CCTGGAACTG AATATGCATC CCATGACAGG GAGAATAGGA GATTCGGAGT  26663

TAAGAAGGAG AGGAGGTCAG TACTGCTGTT CAGAGATTTT TTTTATGTAA CTCTTGAGAA  26723

GCAAAACTAC TTTTGTTCTG TTTGGTAATA TACTTCAAAA CAAACTTCAT ATATTCAAAT  26783

TGTTCATGTC CTGAAATAAT TAGGTAATGT TTTTTTCTCT ATAG GAA ATG AAT CCT   26839
                                                 Glu Met Asn Pro
                                                 85

CCT GAT AAC ATC AAG GAT ACA AAA AGT GAC ATC ATA TTC TTT CAG AGA    26887
Pro Asp Asn Ile Lys Asp Thr Lys Ser Asp Ile Ile Phe Phe Gln Arg
    90                  95                  100

AGT GTC CCA GGA CAT GAT AAT AAG ATG CAA TTT GAA TCT TCA TCA TAC    26935
Ser Val Pro Gly His Asp Asn Lys Met Gln Phe Glu Ser Ser Ser Tyr
105                 110                 115                 120

GAA GGA TAC TTT CTA GCT TGT GAA AAA GAG AGA GAC CTT TTT AAA CTC    26983
Glu Gly Tyr Phe Leu Ala Cys Glu Lys Glu Arg Asp Leu Phe Lys Leu
                125                 130                 135

ATT TTG AAA AAA GAG GAT GAA TTG GGG GAT AGA TCT ATA ATG TTC ACT    27031
Ile Leu Lys Lys Glu Asp Glu Leu Gly Asp Arg Ser Ile Met Phe Thr
            140                 145                 150

GTT CAA AAC GAA GAC T AGCTATTAAA ATTTCATGCC GGGCGCAGTG GCTCACGCCT  27087
Val Gln Asn Glu Asp
        155

GTAATCCCAG CCCTTTGGGA GGCTGAGGCG GGCAGATCAC CAGAGGTCAG GTGTTCAAGA  27147

CCAGCCTGAC CAACATGGTG AAACCTCATC TCTACTAAAA ATACAAAAAA TTAGCTGAGT  27207

GTAGTGACCC ATGCCCTCAA TCCCAGCTAC TCAAGAGGCT GAGGCAGGAG AATCACTTGC  27267

ACTCCGGAGG TGGAGGTTGT GGTGAGCCGA GATTGCACCA TTGCGCTCTA GCCTGGGCAA  27327

CAACAGCAAA ACTCCATCTC AAAAAATAAA ATAAATAAAT AAACAAATAA AAAATTCATA  27387

ATGTGAACTG TCTGAATTTT TATGTTTAGA AAGATTATGA GATTATTAGT CTATAATTGT  27447

AATGGTGAAA TAAAATAAAT ACCAGTCTTG AAAAACATCA TTAAGAAATG AATGAACTTT  27507

CACAAAAGCA AACAAACAGA CTTTCCCTTA TTTAAGTGAA TAAAATAAAA TAAAATAAAA  27567

TAATGTTTAA AAAATTCATA GTTTGAAAAC ATTCTACATT GTTAATTGGC ATATTAATTA  27627

TACTTAATAT AATTATTTTT AAATCTTTTG GGTTATTAGT CCTAATGACA AAAGATATTG  27687

ATATTTGAAC TTTCTAATTT TTAAGAATAT CGTTAAACCA TCAATATTTT TATAAGGAGG  27747

CCACTTCACT TGACAAATTT CTGAATTTCC TCCAAAGTCA GTATATTTTT AAAATTCAGT  27807

TTGATCCTGA ATCCAGCAAT ATATAAAAGG GATTATATAC TCTGGCCAAC TGACATTCAT  27867

CCTAGGAATG CAAAGATGGT TTAATATCCT AAAATCAATT AACATAACAT ACTATATTAA  27927

TAAAGTATCA AAACAGTATT CTCATCTTTT TTTCTTTTTT CACAATTCCT TGGTTACACT  27987

ATCATCTCAA TAGATGCAGA AAAAGCATTT GACAAAATCC AATTCATAAT AAAAATTCTC  28047

AAACTTGAAA GAGAACATCA TAAAGGCATC TATGAAAAAC CTACAGCTAA TATCATACTT  28107

AACGATGAAA AACTGAATTA TTTTACCCTA AGATCAAGAA TAATGCAAGC ATGTCAGCTC  28167

TTGCAACTTC TATTCAACAT TGTACTGGAG GTTCTAGCCA GAGCAACCAT ACAATAAATA  28227

AAAATAAAAG GCACCCAGAT TAGAAAGGAA GTCTTTATTT GCAGACAACA TGGTTCTTTA  28287
```

-continued

```
TGCAGAAAAC CGTCAGGAAT ACACACACAT GTTAGAACTA ATAAGTTCAG CAAGGTTGCA  28347

GGTTGCAATA TCAATATGCA AAAATACATT GAAGGCTGGG CTCAGTGGAG ATGGCATGTA  28407

CCTTTCGTCC CAGCTACTTG GGAGGCTGAG GTAGGAGGAT CACTTGAGGT GAGGAGTTTG  28467

AGGCTATAGT GCAATGTGAT CTTGCCTGTG AATAGCCACT GCACTCGAGC CTAGGCAACA  28527

AAGTGAGACC CCGTCTCCAA AAAAAAAAAT GGTATATTGG TATTTCTGTA TATGAACAAT  28587

GAATGATCTG AAAACAAGAA AATTCCATTC ACGATGGTAT TAAAAAAATA AAATACAAAT  28647

AAATTTAGCA AAATAATTAT AAAACTTGTA CATCGAAAAT TTCAAAGCAC TCTGAGGGAA  28707

ATTAAAGATG ATCTAAATAA TTGGAGAGAC ACTCTATGAT CACTGATTGG AAAATTCATT  28767

CAATATTGTT AAGATAACAA TTGTCCCCAA ATTGATGCAT GCATTCAATT TAGTCTTCAT  28827

CAAAATTCCA GCAGGGTTTT TGCAGAAATT GACAAGCTGT ACCCAAAATG TATATGGAAA  28887

TGAAAAGACC CAGAAGAGCA AATAATTTTT TAAAAACAAA GTTGGAAAAC TTTTACTTCC  28947

TAATTTTAAA ACTTACTATA AACCTAAAGT TATCAAGACC ATTTAGT                28994
```

(2) INFORMATION FOR SEQ ID NO: 15:

(i) SEQUENCE CHARACTERISTICS:
(A) LENGTH: 10 amino acids
(B) TYPE: amino acid
(D) TOPOLOGY: linear (ii) MOLECULE TYPE: peptide (v) FRAGMENT TYPE: N-terminal fragment (xi) SEQUENCE DESCRIPTION: SEQ ID NO: 15:

```
Tyr Phe Gly Lys Leu Glu Ser Lys Leu Ser
1               5                   10
```

(2) INFORMATION FOR SEQ ID NO:16:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

```
CCATCCTAAT ACGACTCACT ATAGGGC                                         27
```

(2) INFORMATION FOR SEQ ID NO:17:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

```
TTCCTCTTCC CGAAGCTGTG TAGACTGC                                        28
```

(2) INFORMATION FOR SEQ ID NO:18:

(i) SEQUENCE CHARACTERISTICS:
(A) LENGTH: 18 base pairs
(B) TYPE: nucleic acid

-continued (C) STRANDEDNESS: single
(D) TOPOLOGY: linear (ii) MOLECULE TYPE: cDNA (xi) SEQUENCE DESCRIPTION: SEQ ID NO:18:

CTATAGGGCA CGCGTGGT 18

(2) INFORMATION FOR SEQ ID NO:19:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

TTCCTCTTCC CGAAGCTGTG TAGACTGC 28

(2) INFORMATION FOR SEQ ID NO:20:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:20:

GTAAGTTTTC ACCTTCCAAC TGTAGAGTCC 30

(2) INFORMATION FOR SEQ ID NO:21:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:21:

GGGATCAAGT CGTGATCAGA AGCAGCACAC 30

(2) INFORMATION FOR SEQ ID NO:22:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:22:

CCTGGCTGCC AACTCTGGCT GCTAAAGCGG 30

(2) INFORMATION FOR SEQ ID NO:23:

(i) SEQUENCE CHARACTERISTICS:
(A) LENGTH: 33 base pairs
(B) TYPE: nucleic acid
(C) STRANDEDNESS: single
(D) TOPOLOGY: linear -continued (ii) MOLECULE TYPE: cDNA (xi) SEQUENCE DESCRIPTION: SEQ ID NO:23:

GTATTGTCAA TAAATTTCAT TGCCACAAAG TTG 33

(2) INFORMATION FOR SEQ ID NO:24:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:24:

AAGATGGCTG CTGAACCAGT AGAAGACAAT TGC 33

(2) INFORMATION FOR SEQ ID NO:25:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:25:

TCCTTGGTCA ATGAAGAGAA CTTGGTC 27

(2) INFORMATION FOR SEQ ID NO:26:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:26:

CCTGGAATCA GATTACTTTG GCAAGCTTGA ATC 33

(2) INFORMATION FOR SEQ ID NO:27:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:27:

GGAAATAATT TTGTTCTCAC AGGAGAGAGT TG 32

(2) INFORMATION FOR SEQ ID NO:28:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: cDNA -continued (xi) SEQUENCE DESCRIPTION: SEQ ID NO:28:

GCCAGCCTAG AGGTATGGCT GTAACTATCT C 31

(2) INFORMATION FOR SEQ ID NO:29:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:29:

GGCATGAAAT TTTAATAGCT AGTCTTCGTT TTG 33

(2) INFORMATION FOR SEQ ID NO:30:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:30:

GTGACATCAT ATTCTTTCAG AGAAGTGTCC 30

(2) INFORMATION FOR SEQ ID NO:31:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:31:

GCAATTTGAA TCTTCATCAT ACGAAGGATA C 31

(2) INFORMATION FOR SEQ ID NO:32:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:32:

TCCGAAGCTT AAGATGGCTG CTGAACCAGT A 31

(2) INFORMATION FOR SEQ ID NO:33:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: cDNA -continued

```
    (xi) SEQUENCE DESCRIPTION: SEQ ID NO:33:

GGAAATAATT TTGTTCTCAC AGGAGAGAGT TG                                  32


(2) INFORMATION FOR SEQ ID NO:34:

     (i) SEQUENCE CHARACTERISTICS:
          (A) LENGTH: 37 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:34:

ATGTAGCGGC CGCGGCATGA AATTTTAATA GCTAGTC                             37


(2) INFORMATION FOR SEQ ID NO:35:

     (i) SEQUENCE CHARACTERISTICS:
          (A) LENGTH: 33 base pairs
          (B) TYPE: nucleic acid
          (C) STRANDEDNESS: single
          (D) TOPOLOGY: linear

    (ii) MOLECULE TYPE: cDNA

    (xi) SEQUENCE DESCRIPTION: SEQ ID NO:35:

CCTGGAATCA GATTACTTTG GCAAGCTTGA ATC                                 33
```